US011896654B2

(12) United States Patent
Weiner et al.

(10) Patent No.: US 11,896,654 B2
(45) Date of Patent: Feb. 13, 2024

(54) DNA MONOCLONAL ANTIBODIES TARGETING CHECKPOINT MOLECULES

(71) Applicants: The Trustees of the University of Pennsylvania, Philadelphia, PA (US); THE WISTAR INSTITUTE OF ANATOMY AND BIOLOGY, Philadelphia, PA (US); Inovio Pharmaceuticals, Inc., Plymouth Meeting, PA (US)

(72) Inventors: David B. Weiner, Merion, PA (US); Kar Muthumani, Cherry Hill, NJ (US); Niranjan Sardesai, Blue Bell, PA (US)

(73) Assignees: The Trustees of the University of Pennsylvania, Philadelphia, PA (US); The Wistar Institute of Anatomy and Biology, Philadelphia, PA (US); Inovio Pharmaceuticals, Plymouth Meeting, PA (US)

(*) Notice: Subject to any disclaimer, the term of this patent is extended or adjusted under 35 U.S.C. 154(b) by 617 days.

(21) Appl. No.: 16/098,925

(22) PCT Filed: May 5, 2017

(86) PCT No.: PCT/US2017/031440
§ 371 (c)(1),
(2) Date: Nov. 5, 2018

(87) PCT Pub. No.: WO2017/193094
PCT Pub. Date: Nov. 9, 2017

(65) Prior Publication Data
US 2019/0142920 A1    May 16, 2019

Related U.S. Application Data

(60) Provisional application No. 62/332,386, filed on May 5, 2016.

(51) Int. Cl.
| | | |
|---|---|---|
| *A61K 39/00* | (2006.01) | |
| *C12N 15/85* | (2006.01) | |
| *C07K 16/28* | (2006.01) | |
| *A61K 31/7088* | (2006.01) | |
| *A61P 35/00* | (2006.01) | |
| *A61K 39/395* | (2006.01) | |

(52) U.S. Cl.
CPC .. *A61K 39/001129* (2018.08); *A61K 31/7088* (2013.01); *A61K 39/395* (2013.01); *A61P 35/00* (2018.01); *C07K 16/2803* (2013.01); *C07K 16/2818* (2013.01); *C07K 16/2878* (2013.01); *C12N 15/85* (2013.01); *A61K 2039/505* (2013.01); *A61K 2039/53* (2013.01)

(58) Field of Classification Search
CPC ........ A61K 39/001129; A61K 31/7088; A61K 39/395; A61K 2039/505; A61K 2039/53; A61K 39/0011; A61K 48/00; A61P 35/00; A61P 37/00; C07K 16/2803; C07K 16/2818; C07K 16/2878; C07K 14/4748; C07K 2319/50; C12N 15/85
See application file for complete search history.

(56) References Cited

U.S. PATENT DOCUMENTS

| | | | | |
|---|---|---|---|---|
| 2009/0217401 A1* | 8/2009 | Korman | ................ | A61K 51/10 800/18 |
| 2009/0221682 A1* | 9/2009 | Maithal | .......... | A61K 39/001102 514/44 R |
| 2011/0271358 A1 | 11/2011 | Freeman | | |
| 2015/0284448 A1* | 10/2015 | Weiner | ................... | A61K 39/12 424/208.1 |

OTHER PUBLICATIONS

Mariuzza (Annu. Rev. Biophys. Biophys. Chem., 16: 139-159, 1987).*
McCarthy et al. (J. Immunol. Methods, 251(1-2): 137-149, 2001).*
Lin et al. (African Journal of Biotechnology, 10(79):18294-18302, 2011).*

* cited by examiner

*Primary Examiner* — Nelson B Moseley, II
(74) *Attorney, Agent, or Firm* — Riverside Law LLP

(57) ABSTRACT

Disclosed herein is a composition including a recombinant nucleic acid sequence that encodes an antibody or fragment thereof that targets an immune checkpoint molecule. The disclosure also provides a method of preventing and/or treating disease in a subject using said composition and method of generation.

16 Claims, 23 Drawing Sheets
Specification includes a Sequence Listing.

DNA MONOCLONAL ANTIBODIES TARGETING CHECKPOINT MOLECULES

CROSS-REFERENCE TO RELATED APPLICATIONS

This application is the U.S. national stage application filed under 35 U.S.C. § 371 claiming benefit to International Patent Application No. PCT/US17/31440, filed May 5, 2017, which claims priority to U.S. Provisional Application No. 62/332,386, filed May 5, 2016, each of which is incorporated by reference herein in its entirety.

CROSS REFERENCE TO RELATED APPLICATION

This application claims priority to and the benefit of U.S. provisional application No. 62/332,386, filed May 5, 2016, the content of which is incorporated herein in its entirety.

TECHNICAL FIELD

The present invention relates to a composition comprising a recombinant nucleic acid sequence for generating one or more synthetic antibodies, including antibodies targeting the immune checkpoint molecules (e.g., PD-1, PD-L1, LAG-3, GITR, CD40, OX40, CTLA-4, TIM-3, 4-1BB, and combinations and functional fragments thereof), in vivo, and a method of preventing and/or treating cancer, infectious diseases and other conditions in a subject by administering said composition.

BACKGROUND

Vaccines are used to stimulate an immune response in an individual to provide protection against and/or treatment for a particular disease. Some vaccines include an antigen to induce the immune response. Some antigens elicit a strong immune response while other antigens elicit a weak immune response. A weak immune response to an antigen can be strengthened by including an adjuvant in the vaccine. Adjuvants come in many different forms, for example, aluminum salts, oil emulsions, sterile constituents of bacteria or other pathogens, cytokines, and so forth.

Programmed cell death protein 1 also known as PD-1 is a 288 amino acid cell surface protein molecule that in humans is encoded by the PDCD1 gene. This protein is expressed in pro-B cells and is thought to play a role in their differentiation. PD1 is a type I membrane protein of 268 amino acids and a member of the extended CD28/CTLA-4 family of T cell regulators. The protein's structure includes an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals.

PD-1 has two ligands, PD-L1 and PD-L2, which are members of the B7 family. PD-L1 protein is upregulated on macrophages and dendritic cells (DC) in response to LPS and GM-CSF treatment, and on T cells and B cells upon TCR and B cell receptor signaling, whereas in resting mice, PD-L1 mRNA can be detected in the heart, lung, thymus, spleen, and kidney. PD-L1 is expressed on almost all murine tumor cell lines, including PA1 myeloma, P815 mastocytoma, and B16 melanoma upon treatment with IFN-γ. PD-L2 expression is more restricted and is expressed mainly by DCs and a few tumor lines.

There are studies suggesting that PD-1 and its ligands negatively regulate immune responses. PD-1 knockout mice have been shown to develop lupus-like glomerulonephritis and dilated cardiomyopathy on the C57BL/6 and BALB/c backgrounds, respectively. In vitro, treatment of anti-CD3 stimulated T cells with PD-L1-Ig results in reduced T cell proliferation and IFN-γ secretion. It appears that upregulation of PD-L1 may allow cancers to evade the host immune system. PD-L1 expression has been shown to correlate inversely with intraepithelial CD8+T-lymphocyte count, suggesting that PD-L1 on tumor cells may suppress antitumor CD8+ T cells.

LAG3 and TIM3 are some of the many receptor molecules on the surface of T lymphocytes that exert inhibitory functions.

T cell immunoglobulin domain and mucin domain 3 (TIM-3; also known as HAVCR2), is a human protein that is encoded by the HAVCR2 gene. TIM-3 is a protein surface receptor expressed by activated T cells of the IFNgamma-producing CD4 Thi and CD8 cytotoxic T cells. Its ligand is galectin-9 which is abundantly expressed in the tumor microenvironment and induces cell death and T cell exhaustion of CD4 and CD8 T cells. Evidence of Tim-3 as a key immune checkpoint in either tumor or viral-induced immune suppression comes from demonstration that Tim-3 expressing CD8 T cells are the most suppressed or dysfunctional population of CD8 T cell in preclinical models.

Lymphocyte activation gene 3 (Lag-3 also known as CD223) is a member of the Ig superfamily that is expressed only on activated and tolerized T cells that binds MHC-II molecules and which is known to transduce inhibitory signals. LAG-3 is markedly upregulated on exhausted T cells compared to effector or memory T cells. LAG-3 negatively regulates T cell expansion by inhibiting T cell receptor induced calcium fluxes, thus controlling the size of the T cell memory pool. Studies have shown that in the context of cancer, LAG3 is upregulated on TILs and blockade of LAG-3 can enhance antitumor T cell immune responses. Blockage of LAG-3 in a viral chronic model that evokes CD8 T cells exhaustion, can invigorate the CD8 T cell responses.

Collectively, these aforementioned proteins, along with other inhibitory receptors, such as CTLA-4, are important players in the CD8 T cell exhaustion that takes place in chronic immune conditions such as chronic viral infection and cancer in both experimental models and humans. These known features and function of PD1-1, CTLA-4, TIM-3 and LAG-3 make them an appealing target for immune modulation in vaccine settings.

Thus, there is a need in the art for improved compositions and methods that target immune checkpoint molecules for the treatment of cancer, infectious diseases, and other conditions.

SUMMARY OF THE PREFERRED EMBODIMENTS

In one aspect, the invention provides a composition for generating a synthetic antibody in a subject comprising one or more nucleic acid molecules encoding one or more synthetic antibodies or fragments thereof, wherein the one or more antibodies or fragments target at least one immune checkpoint molecule.

In one embodiment, the at least one immune checkpoint molecule is selected from the group consisting of PD-1, LAG-3, PD-L1, GITR, CD40, OX40, CTLA-4, TIM-3, 4-1BB, and a combination thereof.

In one embodiment, the composition comprises a nucleotide sequence encoding a cleavage domain.

In one embodiment, the composition comprises a nucleotide sequence encoding a variable heavy chain region and a variable light chain region of the antibody.

In one embodiment, the composition comprises a nucleotide sequence encoding a constant heavy chain region of human IgG1 and a constant kappa light chain region.

In one embodiment, the composition comprises a nucleotide sequence encoding a polypeptide comprising a variable heavy chain region of the antibody; a constant heavy chain region of human IgG1; a cleavage domain; a variable light chain region of the antibody; and a constant kappa light chain region.

In one embodiment, the composition comprises a nucleotide sequence that encodes a leader sequence.

In one embodiment, the composition comprises a nucleotide sequence encoding at least one amino acid sequence of SEQ ID NOs: 2, 4, 6, 8, 10, 12, 14, 16, 18, 20, 22, 24, 26, and 28.

In one embodiment, the composition comprises at least one nucleic acid sequence of SEQ ID NOs: 1, 3, 5, 7, 9, 11, 13, 15, 17, 19, 21, 23, 25, and 27.

In one embodiment, the one or more nucleic acid molecules are engineered to be in an expression vector.

In one embodiment, the composition further comprises a nucleotide sequence encoding an antigen.

In one embodiment, the composition further comprises a pharmaceutically acceptable excipient.

In another aspect, the invention provides a method of treating a disease in a subject, the method comprising administering to the subject at least one composition of the invention.

In one embodiment, the disease is cancer. In another embodiment, the disease is an infectious disease.

In another aspect, the invention provides a method for increasing an immune response in a subject in need thereof, the method comprising administering a composition of the invention to the subject.

In one embodiment, administering the composition comprises an electroporating step.

In another aspect, the invention provides a method of increasing an immune response in a subject in need thereof by administering a combination of a synthetic antigen and an immune checkpoint inhibitor, wherein the immune checkpoint inhibitor is a synthetic antibody, wherein the administering step comprises: administering to the subject a prime vaccination and a boost vaccination of synthetic antigen, and subsequent to the boost vaccination, administering to the subject an immune checkpoint inhibitor.

In one embodiment, the method further comprises a step of administering to the subject a subsequent boost vaccination of the synthetic antigen. In one embodiment, any of the administering steps include delivering electroporation to the site of administration.

BRIEF DESCRIPTION OF THE DRAWINGS

FIG. 3 provides a series of images demonstrating the construction of PD-1 and LAG-3 dMAb plasmids and confirmation of in vitro and in vivo IgG production.

FIG. 4 provides a series of images showing in vivo produced IgG following PD-1 or LAG-3 dMAb plasmid administration bind specifically to their targets.

FIG. 5 provides a series of images showing that LAG-3 dMAb impedes tumor growth, improves survival, and promotes a less inhibitory tumor microenvironment.

FIG. 12 provides a series of images showing GITR dMAb expression in nude mice.

FIG. 15 provides a series of images showing 4-1BB dMAb production in nude mice, and ELISA assay showing specific binding.

Figure 1:
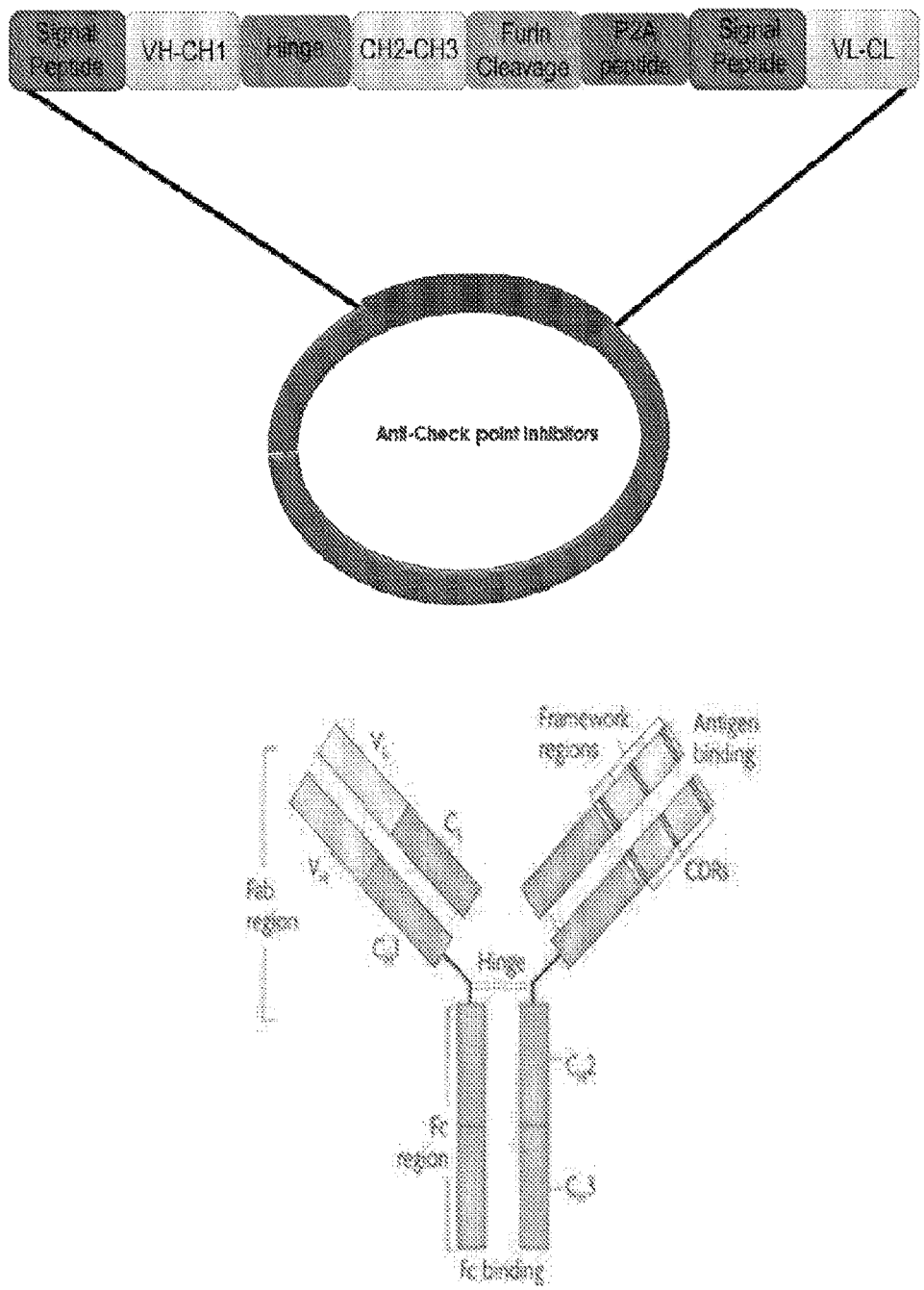
FIG. 1 provides an image depicting the design of DNA based monoclonal antibodies (dMAb).
Figure 2A:
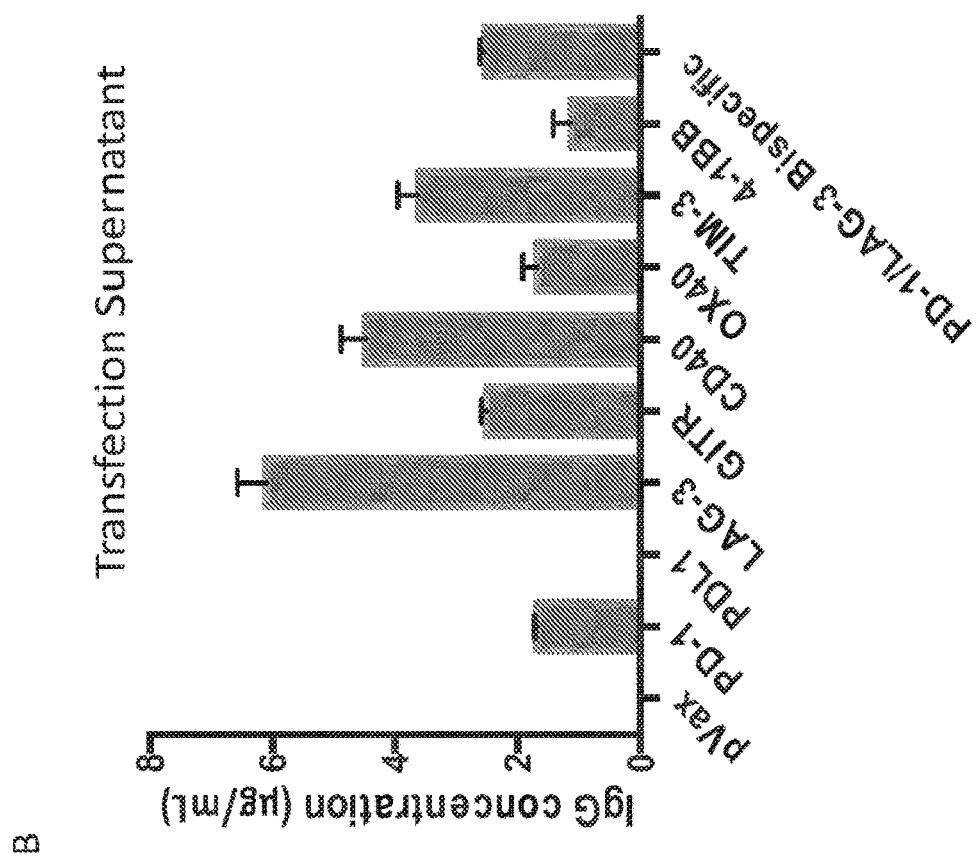
FIG. 2 provides a series of images showing (FIG. 2A) a non-limiting list of targets using dMAb technology, and (FIG. 2B) transfection supernatant IgG concentration (g/mL).
Figure 2B:
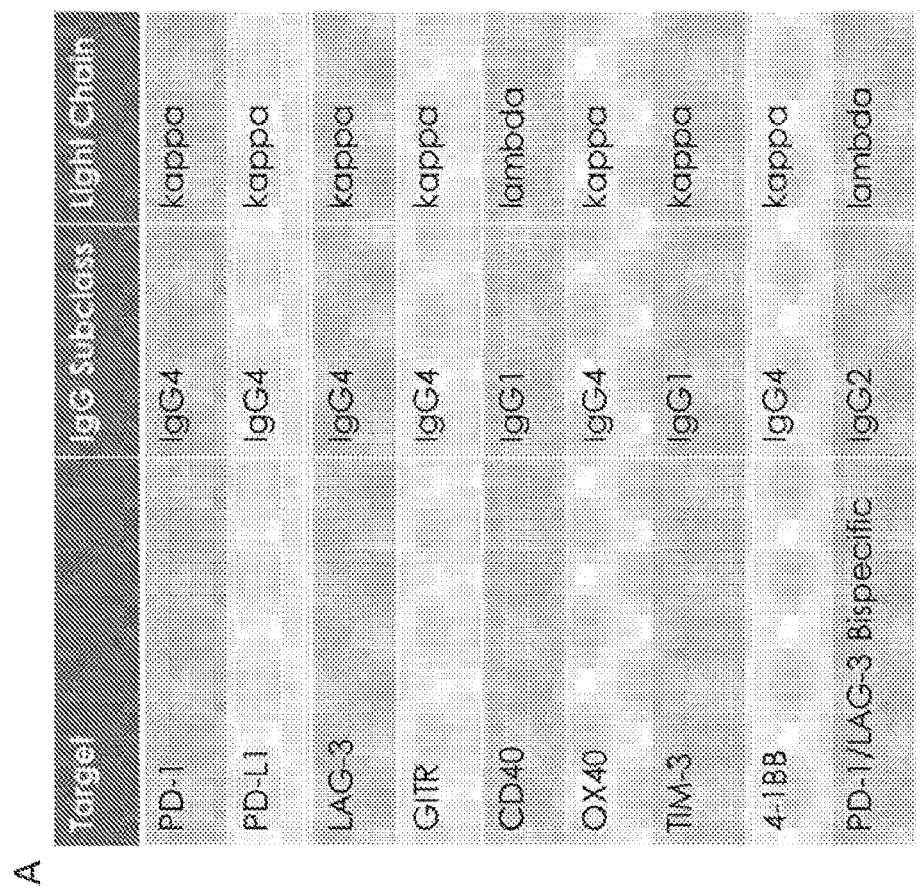
Figures 3A, 3B, 3C:
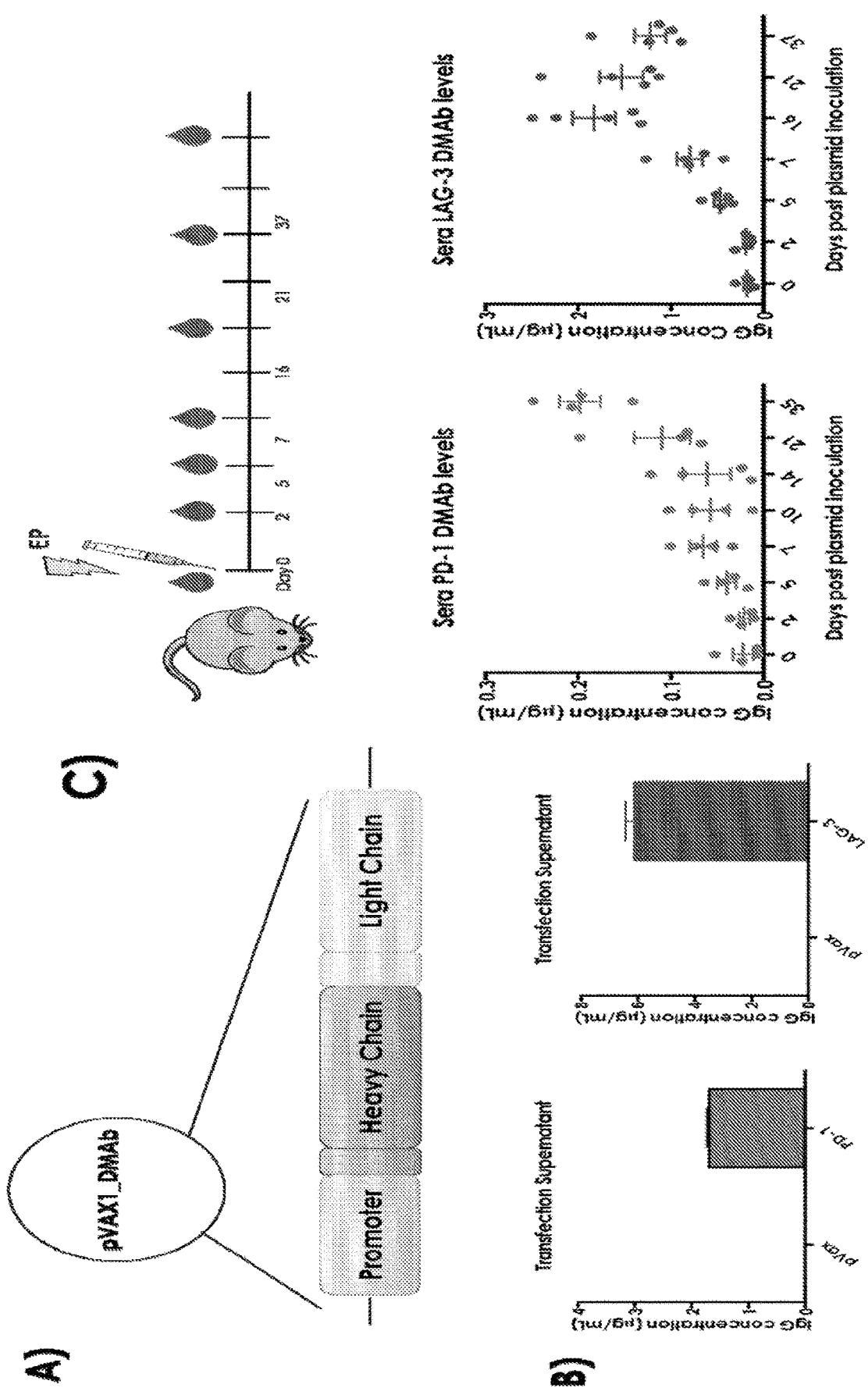
(FIG. 3A) construction of dMAb plasmids.
(FIG. 3B) confirmation of in vitro IgG production.
(FIG. 3C) confirmation of in vivo IgG production.
Figure 4A:
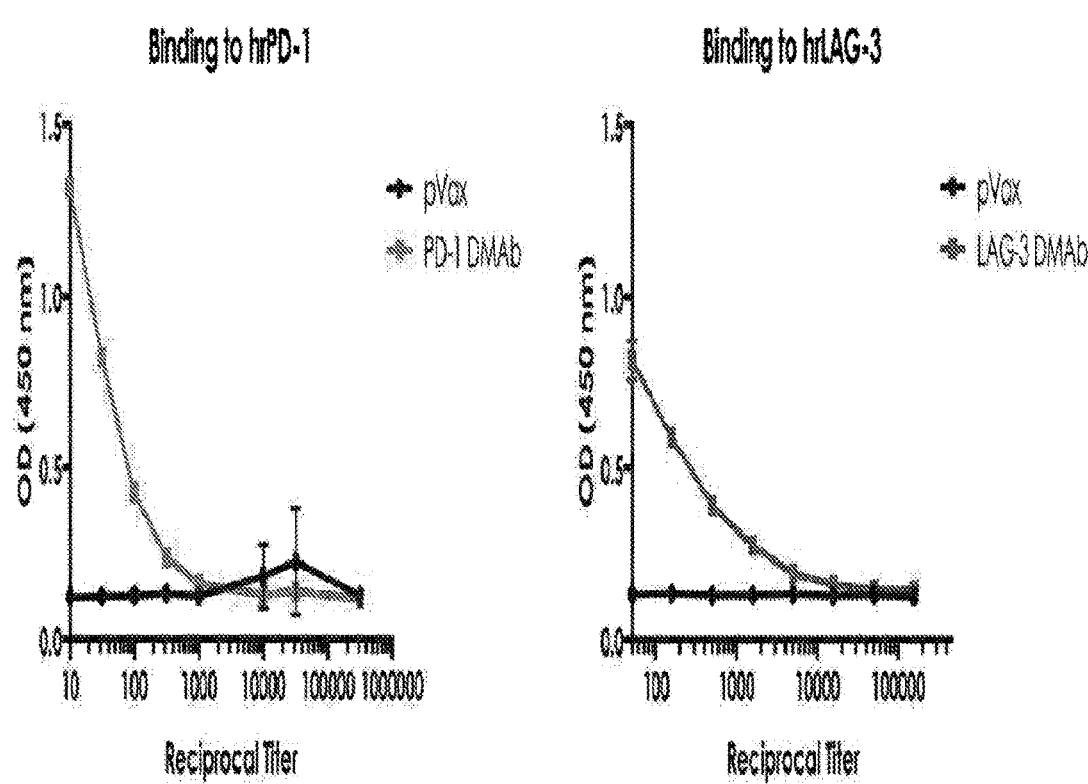
(FIG. 4A) binding to hrPD-1 or hrLAG-3.
Figure 4B:
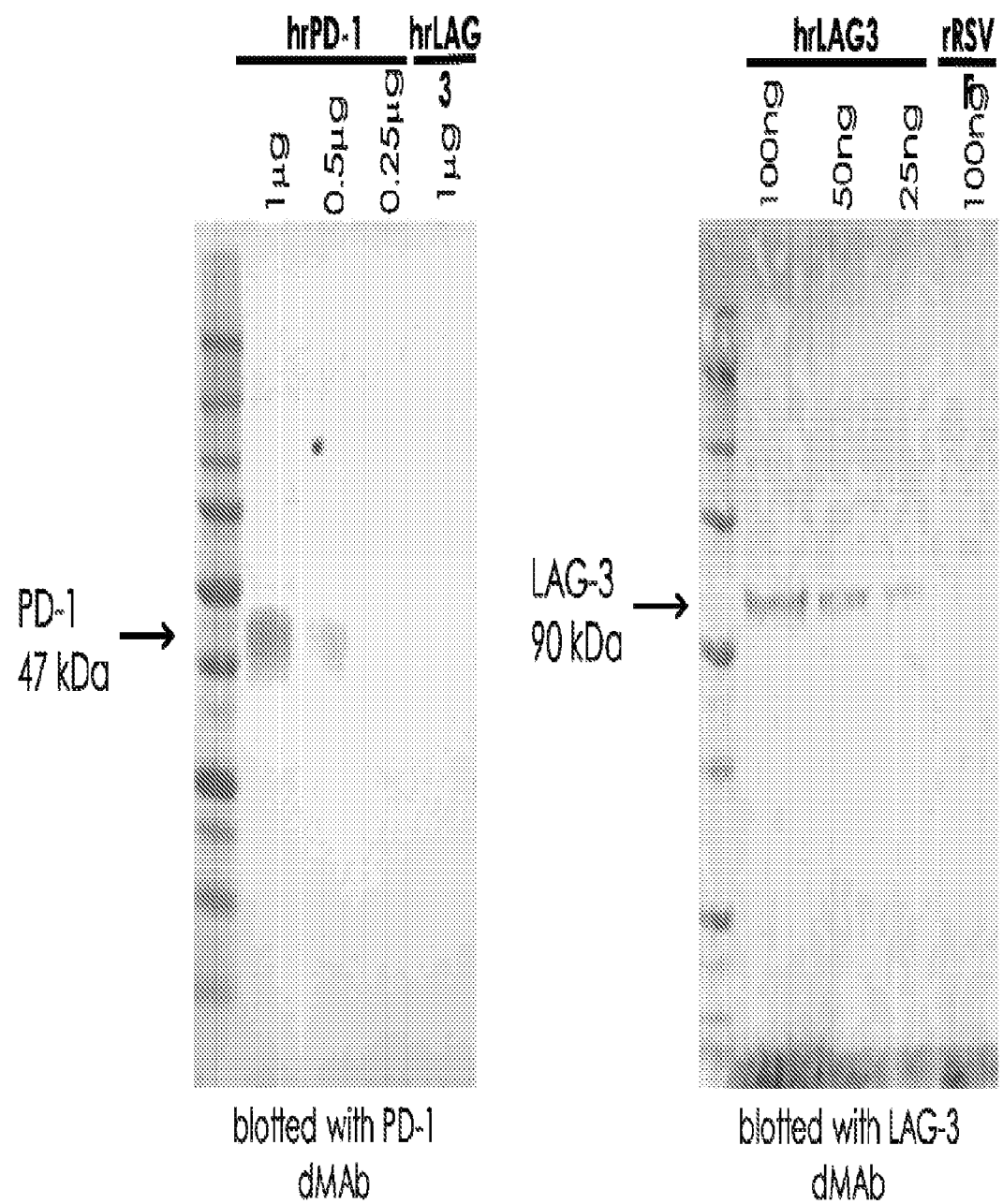
(FIG. 4B) western blots against PD-1 or LAG-3 using corresponding dMAb produced in vivo.
Figure 4C:
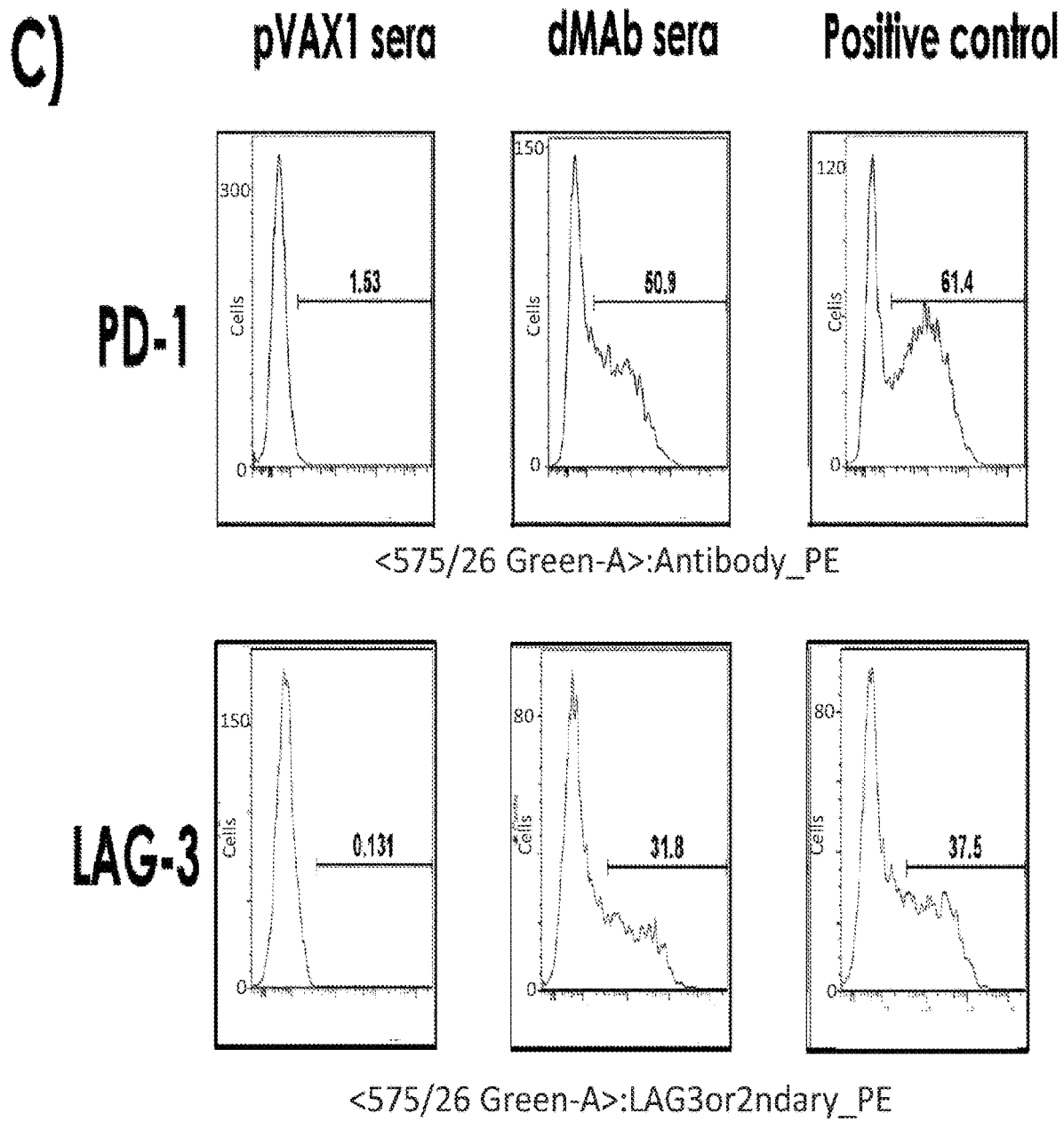
(FIG. 4C) FACS showing binding to PD-1 or LAG-3 using pVAX1 sera, dMAb sera, or positive control.
Figures 5A, 5B:
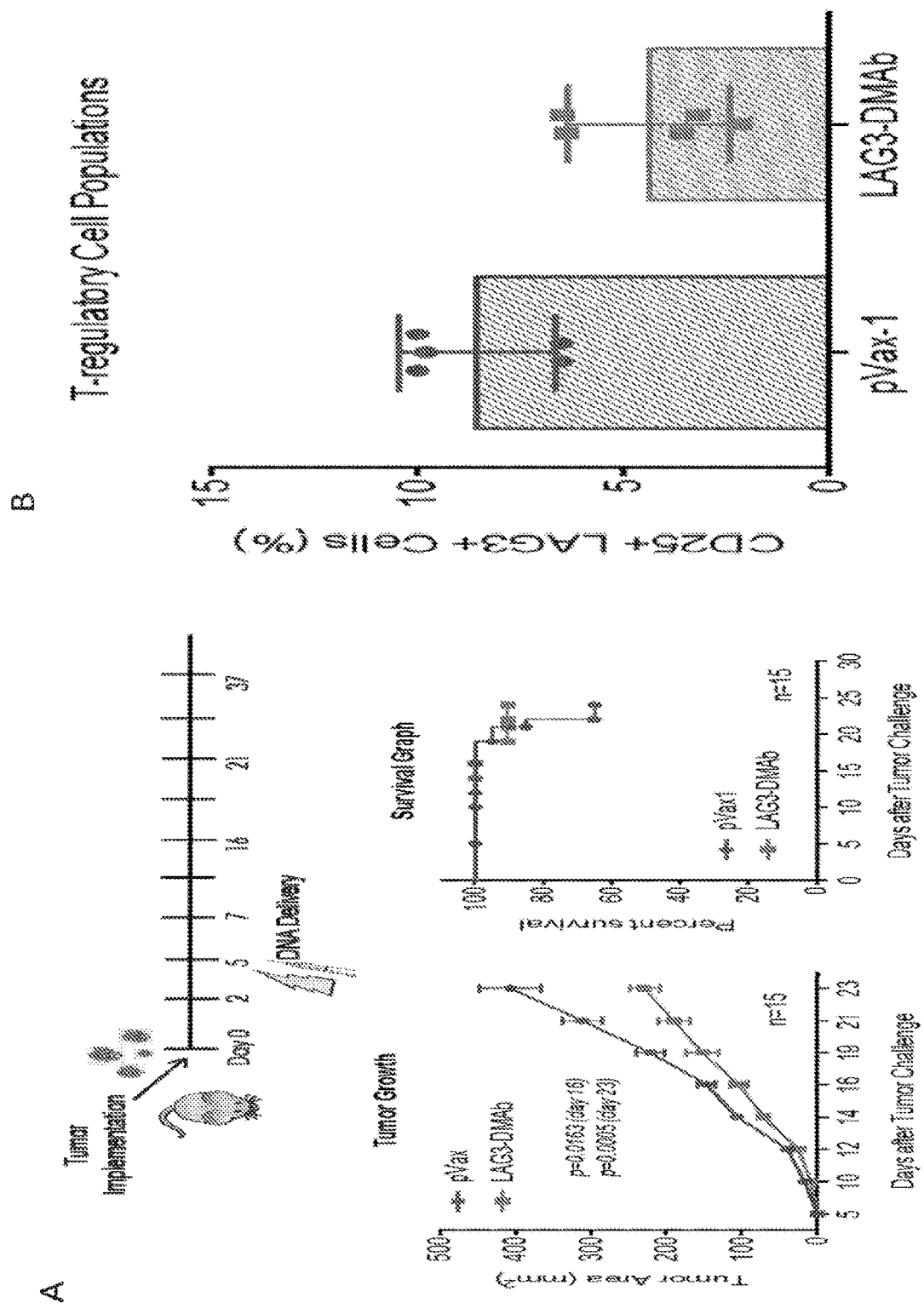
(FIG. 5A) tumor challenge experiment showing improved survival and decreased tumor size following administration of LAG-3 dMAb.
(FIG. 5B) graph showing the percentage of CD25+ LAG3+ cells after treatment with pVax-1 (control) or LAG3 dMAb.
Figure 6A:
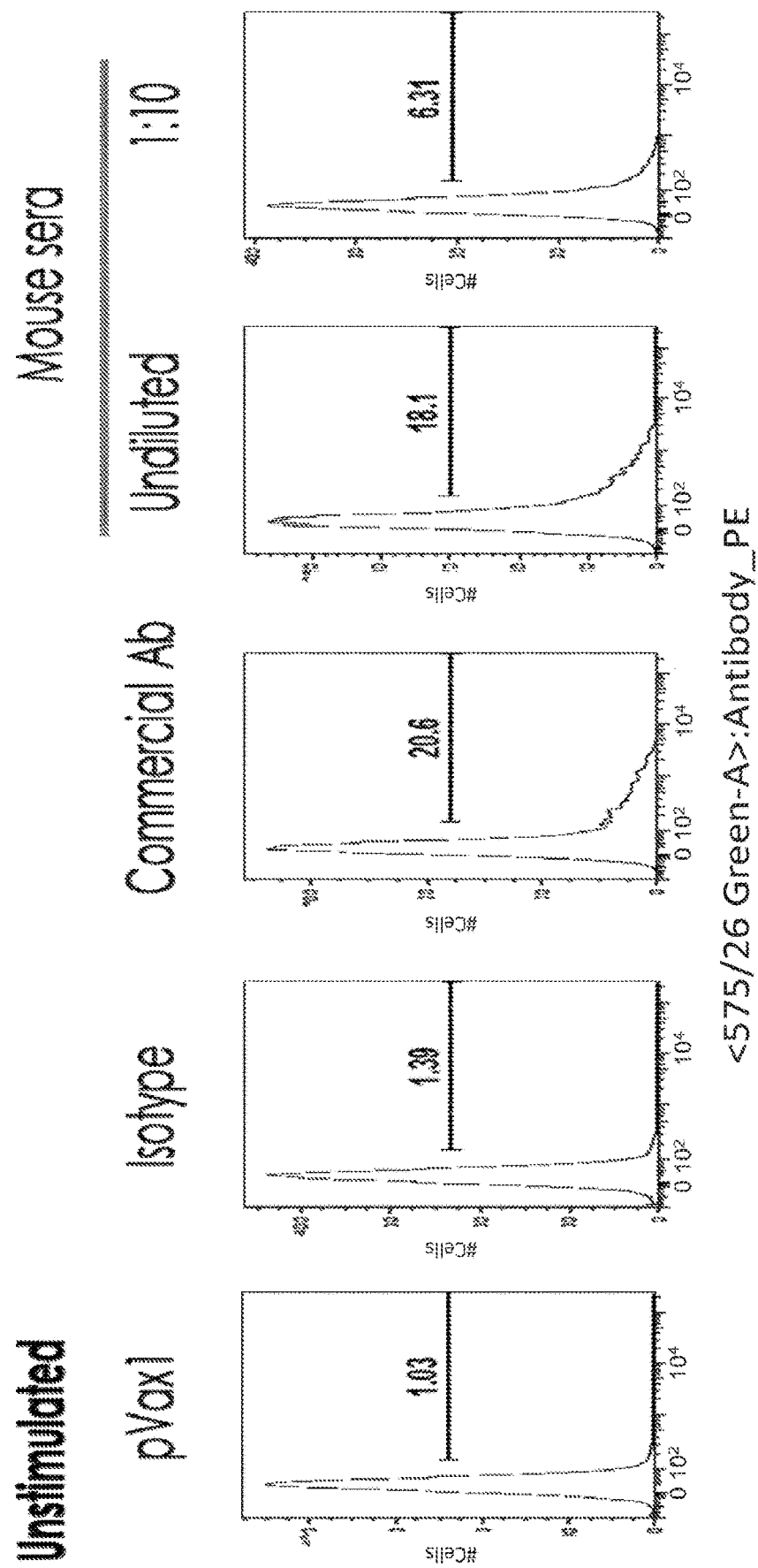
FIG. 6 provides a series of images showing dMAb antibodies bind to activated T cells. FACS analysis of PD-1+ T-cells (FIG. 6A) unstimulated and (FIG. 6B) PHA stimulated, for the various conditions depicted.
Figure 6B:
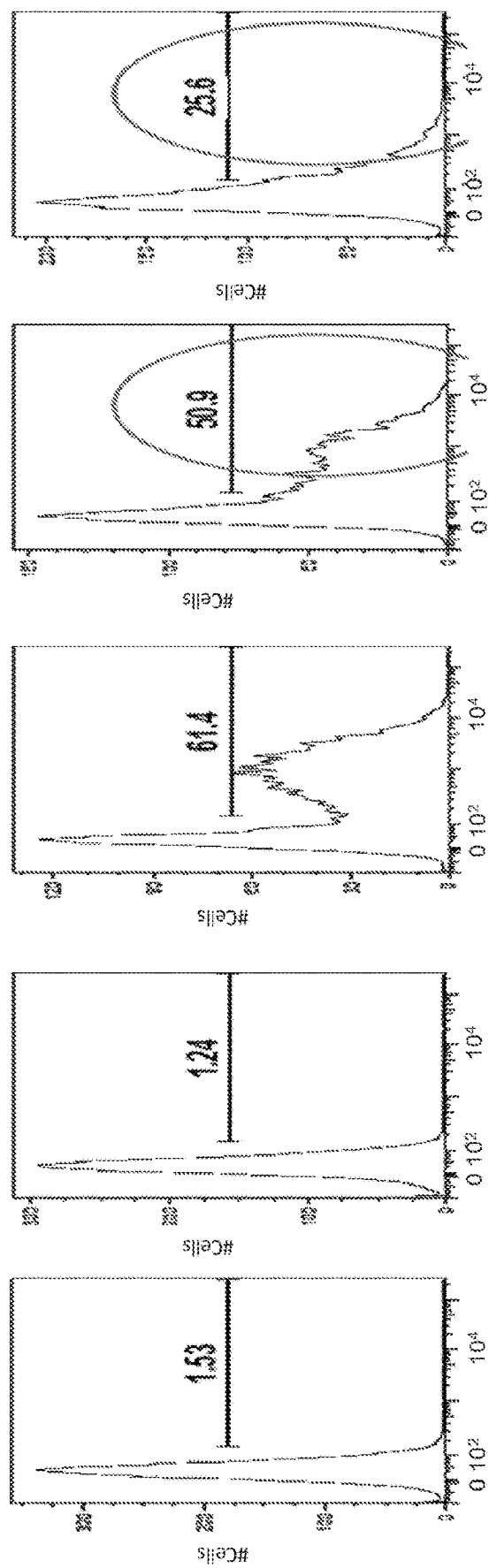
Figure 7:
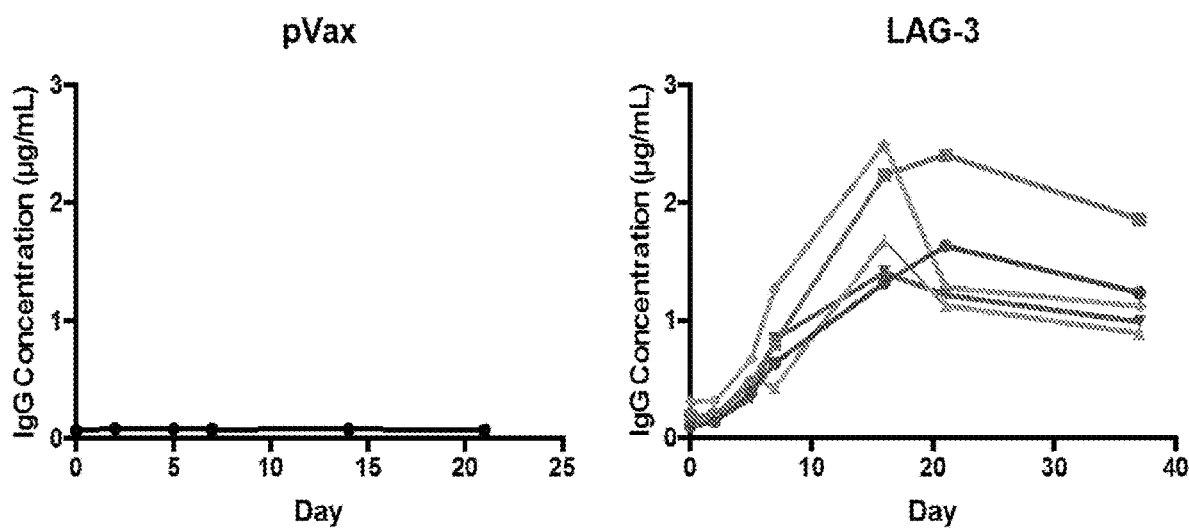
FIG. 7 provides an image showing LAG-3 dMAb IgG concentration in nude mice.
Figure 8:
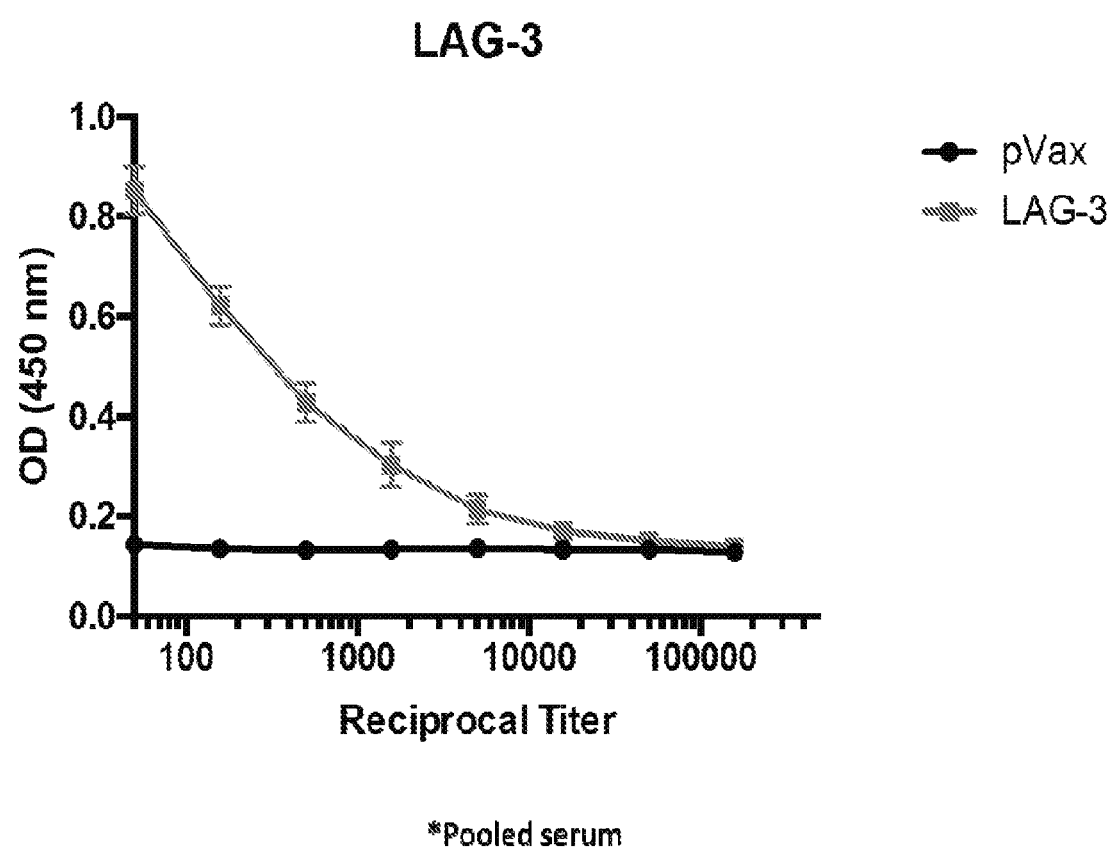
FIG. 8 provides an image showing LAG-3 dMAb binds to LAG-3 in an ELISA assay.
Figure 9:
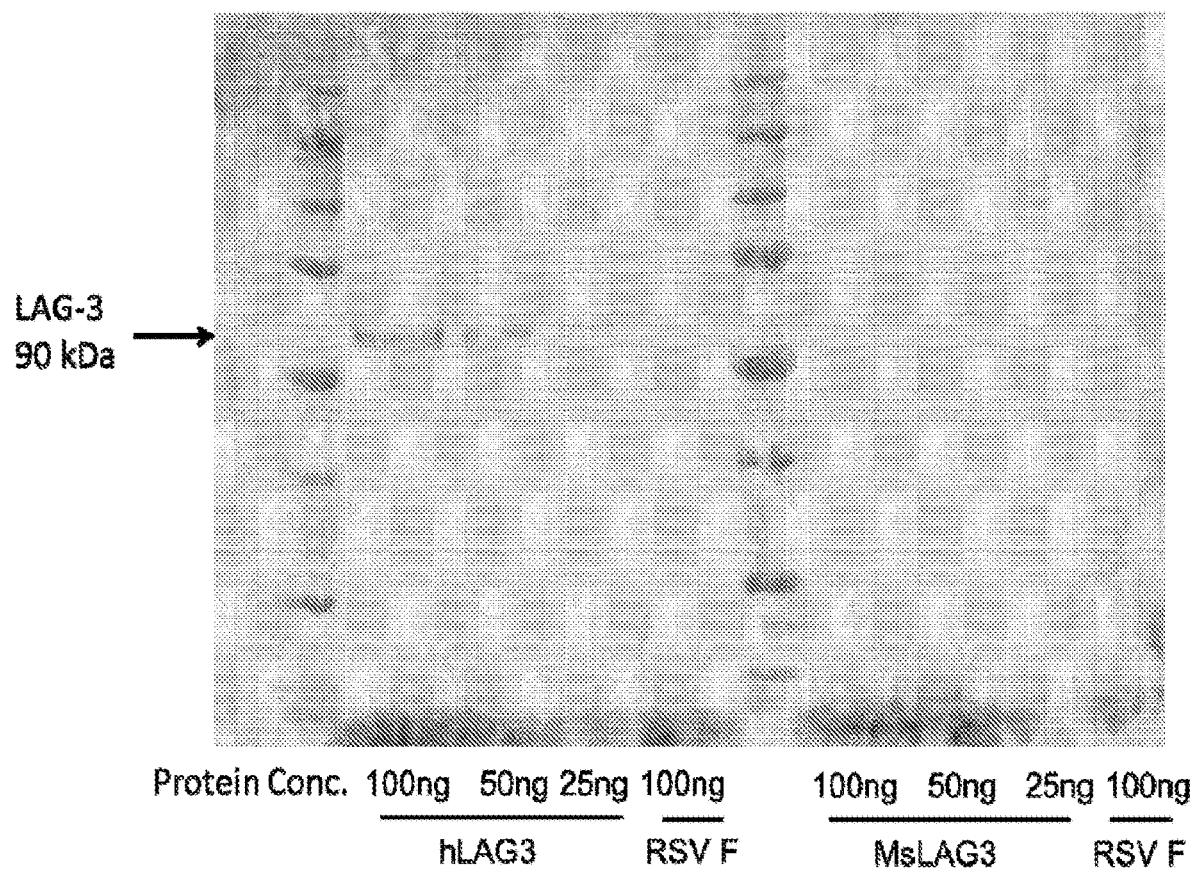
FIG. 9 provides an image showing a western blot for LAG-3, demonstrating the specificity of LAG-3 dMAb for human LAG-3.
Figure 10A:
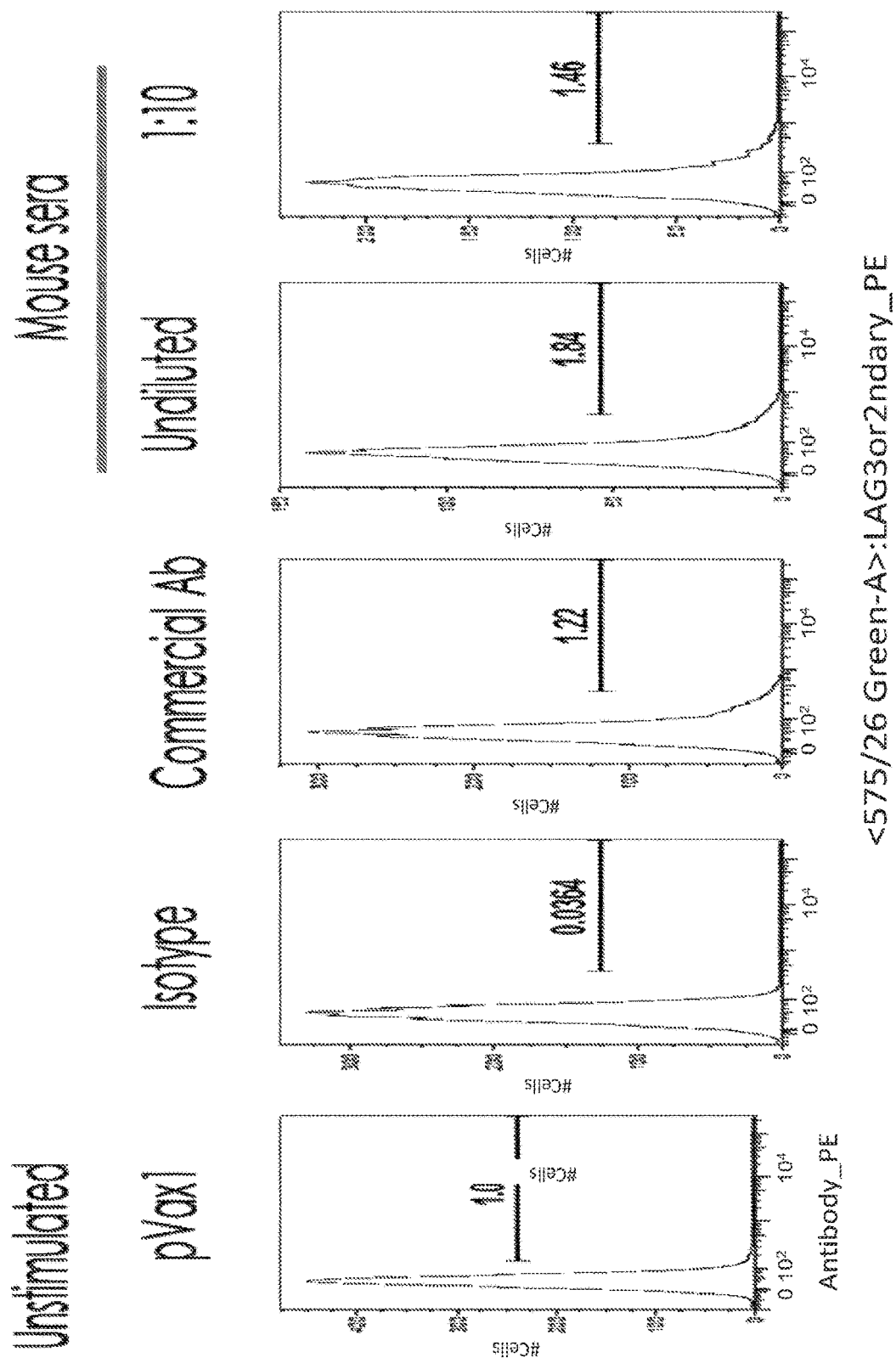
FIG. 10 provides a series of images showing dMAb antibodies bind to activated T cells. FACS analysis of LAG-3+ T-cells (FIG. 10A) unstimulated and (FIG. 10B) PHA stimulated, for the various conditions depicted.
Figure 10B:
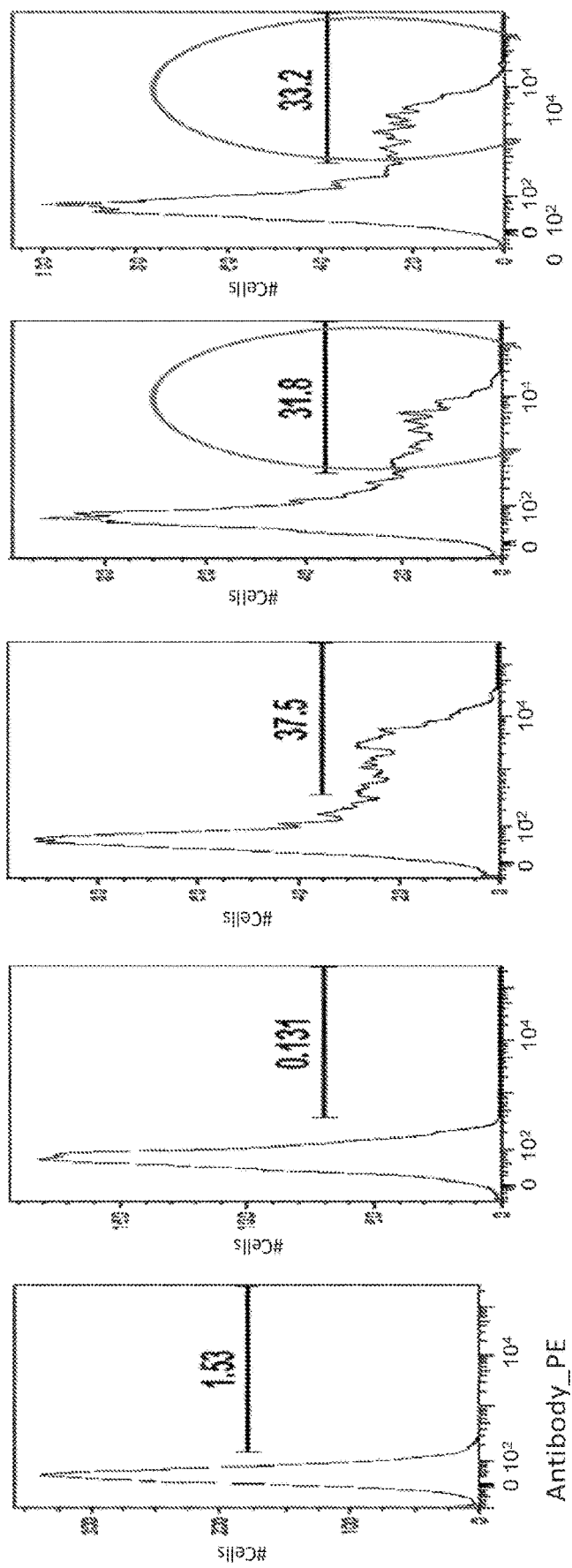
Figure 11:
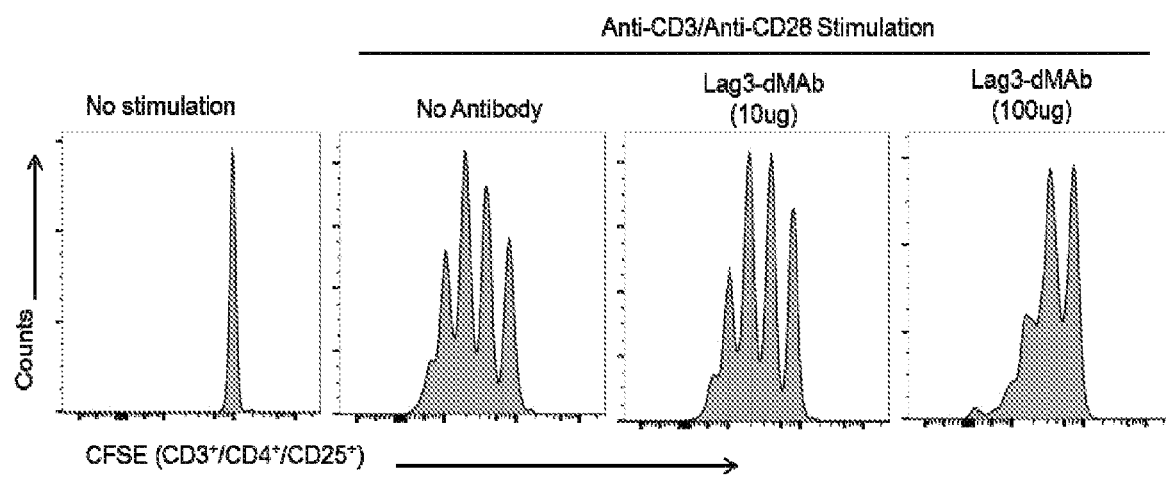
FIG. 11 provides a series of images showing dMAb antibodies block activated Treg cells.
Figures 12A, 12B, 12C:
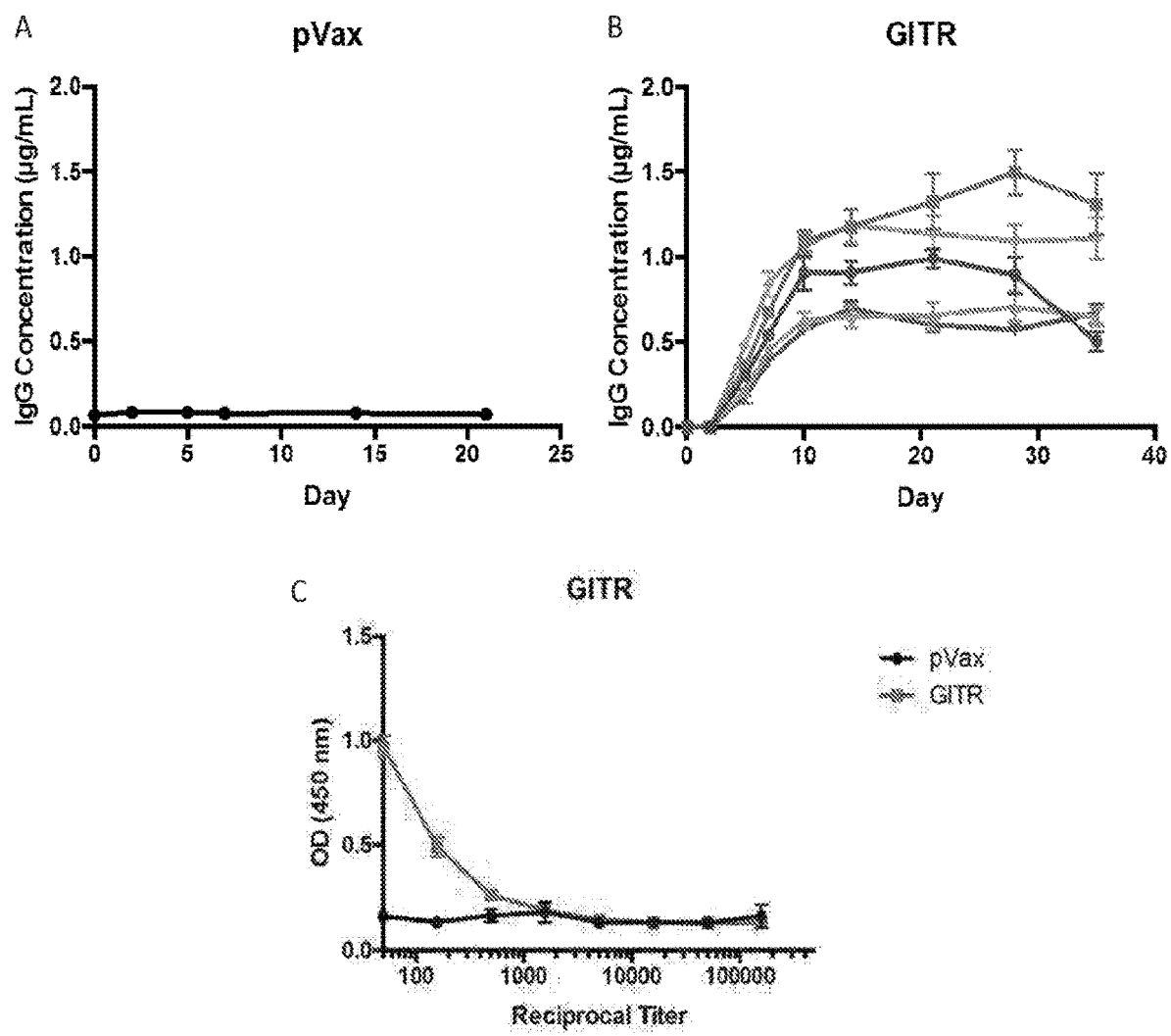
(FIG. 12A) pVax control treatment.
(FIG. 12B) GITR dMAb treatment.
(FIG. 12C) ELISA showing binding of GITR dMAb to GITR.
Figure 13A:
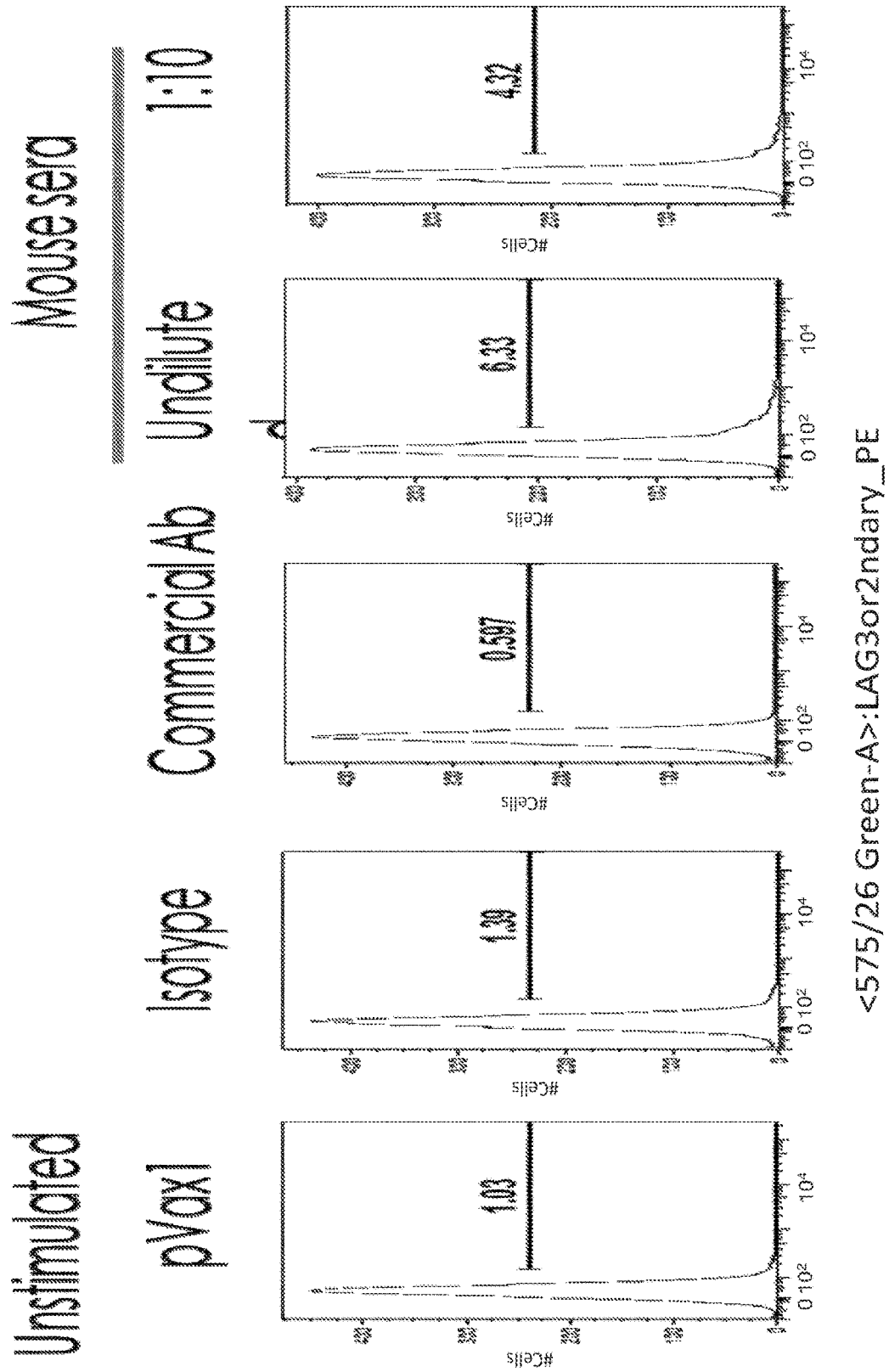
(FIG. 13A) unstimulated versus (FIG. 13B) PHA stimulated cells, for the various conditions depicted.
Figure 13B:
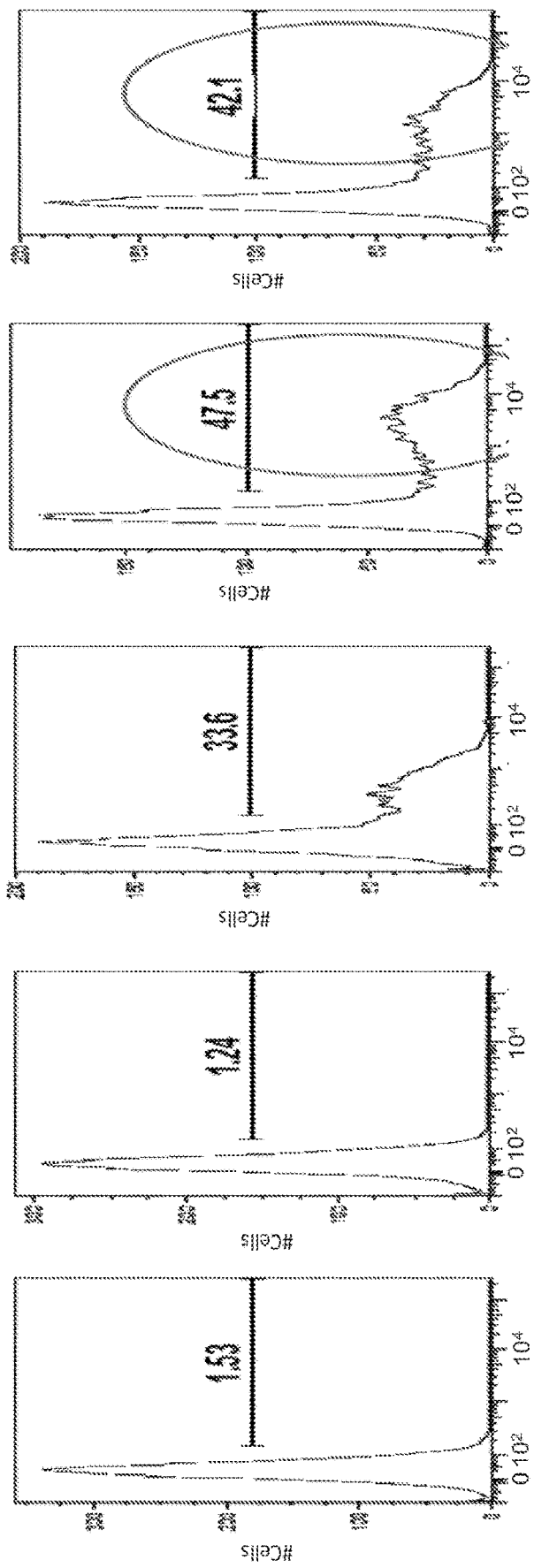
FIG. 13 provides a series of images showing FACS analysis of GITR+ T-cells.
Figure 14:
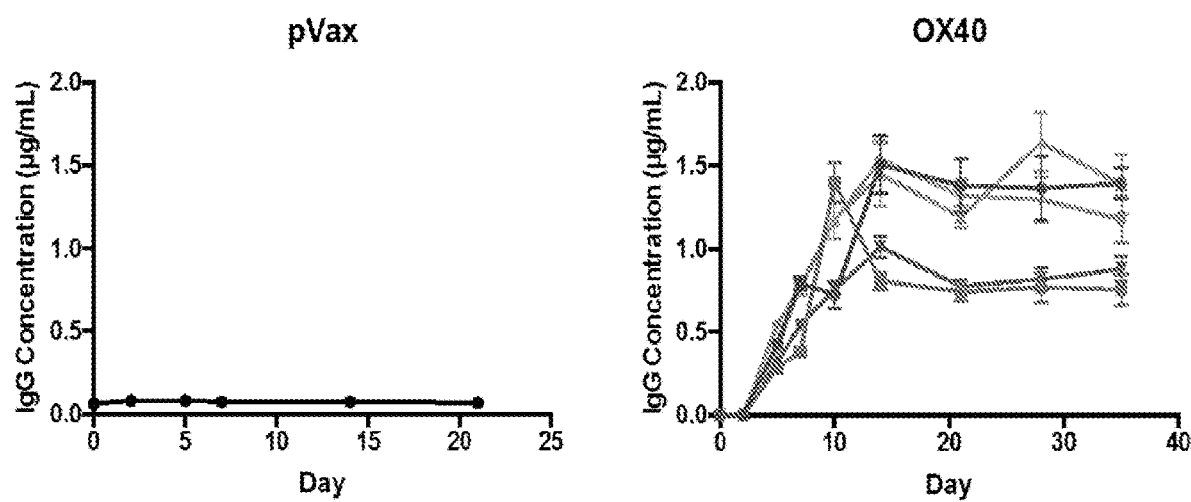
FIG. 14 provides a series of images showing OX40 dMAb production in nude mice.
Figures 15A, 15B, 15C:
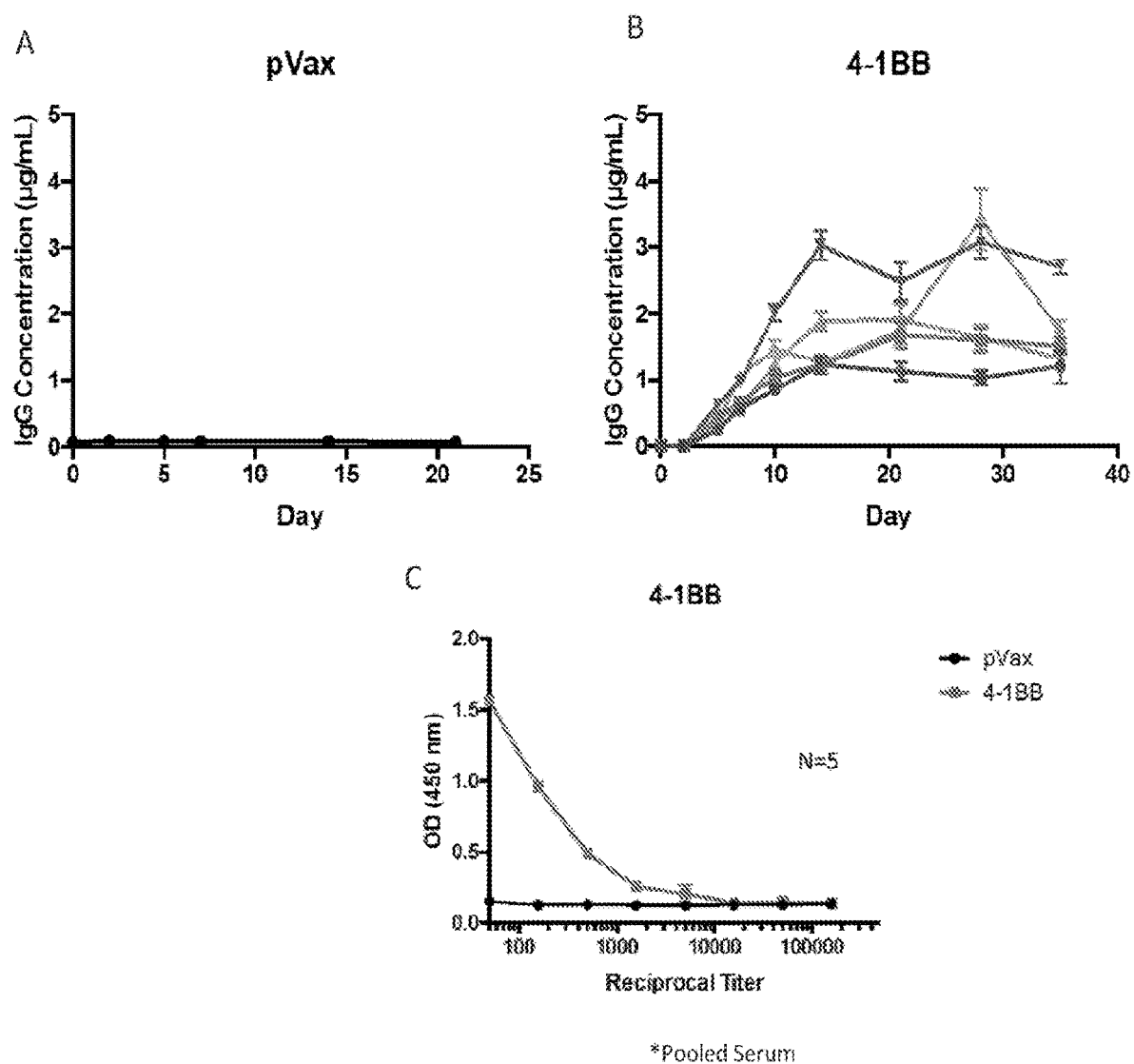
(FIG. 15A) pVax control treatment.
(FIG. 15B) 4-1BB dMAb treatment.
(FIG. 15C) ELISA showing binding of 4-1BB dMAb to 4-1BB.
Figure 16:
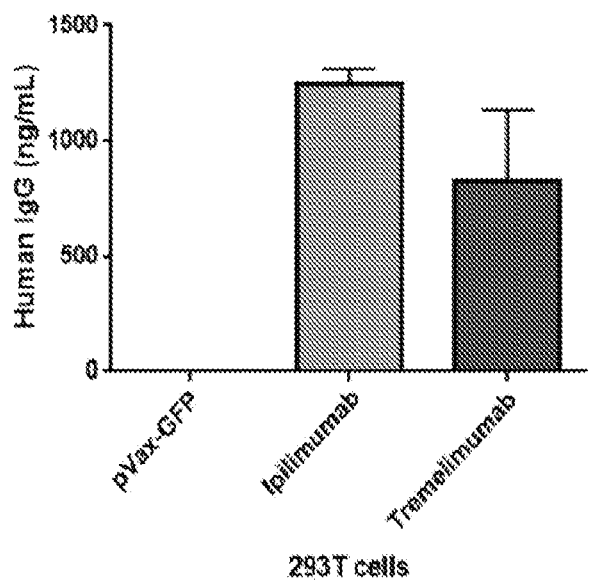
FIG. 16 provides a graph showing anti-CTLA-4 antibodies ipilimumab and tremelimumab expression in 293T cells in vitro.
Figure 17:
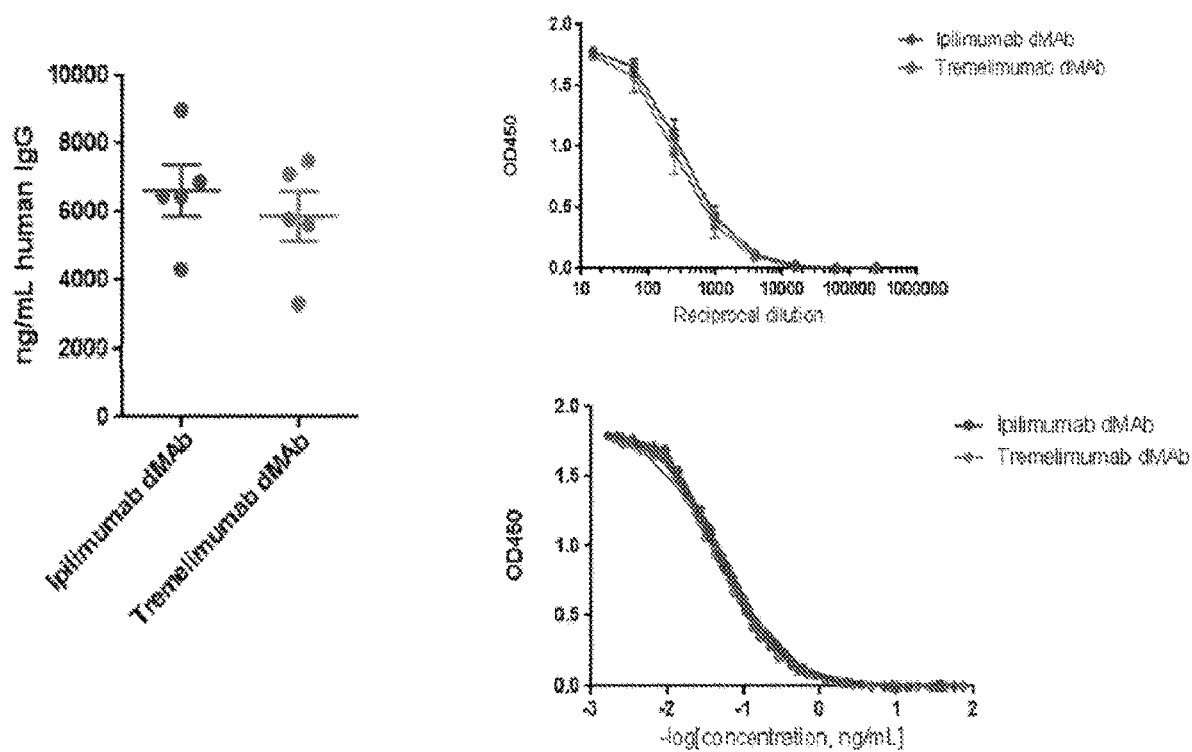
FIG. 17 provides a series of images showing in vivo expression and binding of anti-CTLA-4 antibodies ipilimumab and tremelimumab in Balb/c mice.
Figure 18:
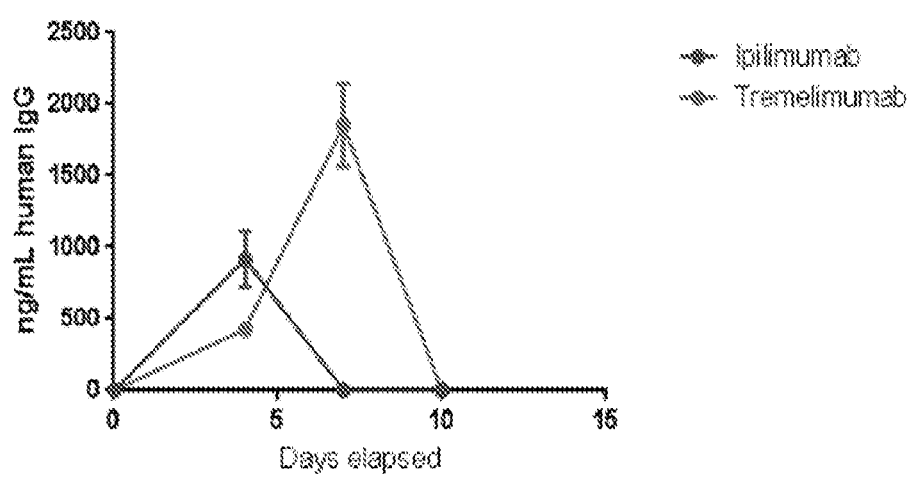
FIG. 18 provides a graph showing in vivo expression of ipilimumab and tremelimumab in Balb/c mice. Delivery was one shot of dMAb (100 µg of DNA at one site).

The graph shows mouse anti-human antibody immune response and clearance.

DETAILED DESCRIPTION OF PREFERRED EMBODIMENTS

The present invention relates to a composition that can be used to increase or enhance an immune response, i.e., create a more effective immune response, by combining a vaccine, in many cases a synthetic antigen, with a checkpoint inhibitor, in particular, PD-1, PD-L1, LAG-3, GITR, CD40, OX40, CTLA-4, TIM-3, and 4-1BB antibodies (e.g., engineered MAb in the form of synthetic DNA plasmids).

Accordingly, with respect to engineered MAb in the form of synthetic DNA plasmids, the present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody. In one embodiment the nucleotide sequence comprises nucleotide sequence described herein. For example, in one embodiment, the nucleotide sequence comprises a sequence of SEQ ID NOs: 1, 3, 5, 7, 9, 11, 13, 15, 17, 19, 21, 23, 25, 27, or a variant thereof or a fragment thereof. In another embodiment, the nucleotide sequence comprises sequence encoding the polypeptide sequence of SEQ ID NOs: 2, 4, 6, 8, 10, 12, 14, 16, 18, 20, 22, 24, 26, 28, or a variant thereof or a fragment thereof. In one embodiment the nucleotide sequence comprises an RNA sequence transcribed from a DNA sequence described herein. For example, in one embodiment, the nucleotide sequence comprises an RNA sequence transcribed by the DNA sequence of SEQ ID NOs: 1, 3, 5, 7, 9, 11, 13, 15, 17, 19, 21, 23, 25, 27, or a variant thereof or a fragment thereof. In another embodiment, the nucleotide sequence comprises an RNA sequence transcribed by a DNA sequence encoding the polypeptide sequence of SEQ ID NOs: 2, 4, 6, 8, 10, 12, 14, 16, 18, 20, 22, 24, 26, 28, or a variant thereof or a fragment thereof.

In one embodiment the nucleotide sequence encodes an amino acid sequence having at least about 80%, at least about 85%, at least about 90%, or at least about 95% identity over the entire length of the amino acid sequence to an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, and SEQ ID NO:28. In one embodiment the nucleotide sequence encodes a fragment of an amino acid sequence having at least about 80%, at least about 85%, at least about 90%, or at least about 95% identity over the entire length of the amino acid sequence to an amino acid sequence selected from the group consisting of SEQ ID NO:2, SEQ ID NO:4, SEQ ID NO:6, SEQ ID NO:8, SEQ ID NO:10, SEQ ID NO: 12, SEQ ID NO: 14, SEQ ID NO: 16, SEQ ID NO: 18, SEQ ID NO:20, SEQ ID NO:22, SEQ ID NO:24, SEQ ID NO:26, and SEQ ID NO:28.

In one embodiment the nucleotide sequence has at least about 80%, at least about 85%, at least about 90%, or at least about 95% identity over the entire length of the nucleotide sequence to a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO: 15, SEQ ID NO: 17, SEQ ID NO: 19, SEQ ID NO:21, SEQ ID NO:23, SEQ ID NO:25, and SEQ ID NO:27. In one embodiment the nucleotide sequence is a fragment of a nucleotide sequence that has at least about 80%, at least about 85%, at least about 90%, or at least about 95% identity over the entire length of the nucleotide sequence to a nucleotide sequence selected from the group consisting of SEQ ID NO:1, SEQ ID NO:3, SEQ ID NO:5, SEQ ID NO:7, SEQ ID NO:9, SEQ ID NO: 11, SEQ ID NO:13, SEQ ID NO:15, SEQ ID NO: 17, SEQ ID NO:19, SEQ ID NO:21, SEQ ID NO:23, SEQ ID NO:25, and SEQ ID NO:27.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the desired target (e.g., immune checkpoint molecule; PD-1, PD-L1, LAG-3, GITR, CD40, OX40, CTLA-4, TIM-3, 4-1BB, and the likes), being more immunogenic as compared to an antibody not assembled as described herein, and being capable of eliciting or inducing an immune response against the desired target.

Additionally, these synthetic antibodies are generated more rapidly in the subject than antibodies that are produced in response to antigen induced immune response. The synthetic antibodies are able to effectively bind and neutralize a range of targets. The synthetic antibodies are also able to effectively protect against and/or promote survival of disease.

In some instances, the antibodies of the invention can be administered in combination with the desired antigen; whereas, in other instances, the antibodies, can be administered separately from the antigen of the vaccine. In some instances the antibodies of the invention comprise a DNA sequence that encodes such antibody, which includes at least the variable regions of the immunoglobulin.

The composition of the present invention can increase the immune response to the antigen in the subject by increasing the $CD8^+$ T cell response as compared to the vaccine not including checkpoint inhibitors. This increased $CD8^+$ T cell response has cytolytic activity and secretes the anti-viral cytokine interferon-gamma (IFN-γ).

Aspects of the present invention include compositions for enhancing an immune response against an antigen in a subject in need thereof, comprising synthetic antibody in combination with a synthetic antigen capable of generating an immune response in the subject, or a biologically functional fragment or variant thereof.

The synthetic antigen can be an isolated DNA that encodes for the antigen. In one embodiment, the antigen is a tumor associated surface antigen. Illustrative examples of a tumor associated surface antigen are CD10, CD19, CD20, CD22, CD33, Fms-like tyrosine kinase 3 (FLT-3, CD135), chondroitin sulfate proteoglycan 4 (CSPG4, melanoma-associated chondroitin sulfate proteoglycan), Epidermal growth factor receptor (EGFR), Her2neu, Her3, IGFR, CD133, IL3R, fibroblast activating protein (FAP), CDCP1, Derlin1, Tenascin, frizzled 1-10, the vascular antigens VEGFR2 (KDR/FLKi), VEGFR3 (FLT4, CD309), PDGFR-.alpha. (CD140a), PDGFR-.beta. (CD140b) Endoglin, CLEC14, Tem1-8, and Tie2. Further examples may include A33, CAMPATH-1 (CDw52), Carcinoembryonic antigen (CEA), Carboanhydrase IX (MN/CA IX), CD21, CD25, CD30, CD34, CD37, CD44v6, CD45, CD133, de2-7 EGFR, EGFRvIII, EpCAM, Ep-CAM, Folate-binding protein, G250, Fms-like tyrosine kinase 3 (FLT-3, CD135), c-Kit (CD117), CSF1R (CD115), HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), and TAG-72. Examples of antigens expressed on the extracellular matrix of tumors are tenascin and the fibroblast activating protein (FAP).

In one embodiment, the synthetic antigen can be selected from the group consisting of: hTERT, PSA, PSMA, STEAP, PSCA, and PAP, WT1, tyrosinase, NYES01, PRAME, MAGE, CMV, herpes, HIV, HPV, HCV, HBV, influenza, RSV, *Plasmodium falciparum*, and *C. difficile*.

The compositions provided herein can also include a pharmaceutically acceptable excipient.

Aspects of the invention also include methods for increasing an immune response in a subject in need thereof by administering any of the compositions provided herein to the subject. The methods of increasing an immune response can also include an electroporating step.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Adjuvant" as used herein means any molecule added to the vaccine described herein to enhance the immunogenicity of the antigens, and in particular refers to checkpoint inhibitor antibodies.

"Checkpoint inhibitor" as used herein means inhibitors or molecules that block immune checkpoints as commonly understood in the field of cancer immunotherapy. More commonly the checkpoint inhibitors are antibodies that block these immune checkpoints.

"Coding sequence" or "encoding nucleic acid" as used herein means the nucleic acid (RNA or DNA molecule) that comprise a nucleotide sequence which encodes a protein, such as an antibody, as set forth herein. The coding sequence may also comprise a DNA sequence which encodes an RNA sequence. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Fragment" as used herein means a nucleic acid sequence or a portion thereof that encodes a polypeptide capable of eliciting an immune response in a mammal. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences set forth below.

Fragment as used herein also means a polypeptide sequence or a portion thereof that is capable of eliciting an immune response in a mammal. The fragments can be polypeptide fragments selected from at least one of the various amino acid sequence set forth below. Fragments can comprise at least 10%, at least 20%, at least 30%, at least 40%, at least 50%, at least 60%, at least 70%, at least 80%, at least 90%, or at least 95% of one or more of the proteins set forth below. In some embodiments, fragments can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of at least one of the proteins set forth below.

"Genetic construct" as used herein refers to the DNA or RNA molecules that comprise a nucleotide sequence which encodes a protein, such as an antibody. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a synthetic antigen, including some of the examples cited herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccine. The mammal can be a human, chimpanzee, dog, cat, horse, cow, pig, chicken mouse, or rat.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%,or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Synthetic antibody" as used herein refers to an antibody that is encoded by the recombinant nucleic acid sequence.

"Treatment" or "treating," as used herein can mean protecting of an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof, or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of +2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof "Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compositions

Provided herein are compositions comprising an antigen and checkpoint inhibitors, preferably checkpoint inhibitor antibodies. The antibodies preferably are synthetic antibodies. The synthetic antibodies preferably are PD-1 antibody, PD-L1 antibody, LAG-3 antibody, GITR antibody, CD40 antibody, OX40 antibody, CTLA-4 antibody, TIM-3 antibody, and/or 4-1BB antibody. The invention also includes novel sequences for use for producing antibodies in mammalian cells or for delivery in DNA or RNA vectors including bacterial, yeast, as well as viral vectors.

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., PD-1, PD-L1, LAG-3, GITR, CD40, OX40, CTLA-4, TIM-3, and/or 4-1BB) present in the subject. Such binding can neutralize the target, block recognition of the target by another molecule, for example, a protein or nucleic acid, and elicit or induce an immune response to the target.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding anti-PD-1 antibody, anti-PD-L1 antibody, anti-LAG-3 antibody, anti-GITR antibody, anti-CD40 antibody, anti-OX40 antibody, anti-CTLA-4, anti-TIM-3 antibody, and/or anti-4-1BB antibody. In one embodiment, the nucleotide sequence encoding the antibody comprises codon optimized nucleic acid sequences encoding the variable VH and VL regions of the antibody. In one embodiment, the nucleotide sequence encoding the antibody comprises codon optimized nucleic acid sequences encoding CH and CL regions of human IgG1κ.

In one embodiment, the first nucleotide sequence encoding a first synthetic antibody comprises a first domain encoding the heavy chain region and a second domain encoding the light chain region of the first synthetic antibody. In one embodiment, the second nucleotide sequence encoding a second synthetic antibody comprises a first domain encoding the heavy chain region and a second domain encoding the light chain region of the second synthetic antibody. In one embodiment, the nucleic acid molecule comprises at least one nucleotide sequence encoding a first domain encoding the heavy chain region and a second domain encoding the light chain region of an antibody selected from the group anti-PD-1 antibody, anti-PD-L1 antibody, anti-LAG-3 antibody, anti-GITR antibody, anti-CD40 antibody, anti-OX40 antibody, anti-CTLA-4 antibody, anti-TIM-3 antibody, and anti-4-1BB antibody.

In one embodiment, the combination can be a single formulation or can be separate and administered in sequence (either antigen first and then checkpoint inhibitor, or checkpoint inhibitor first and then antigen). The composition can increase antigen presentation and the overall immune response to the antigen in a subject. The combination of antigen and checkpoint inhibitor induces the immune system more efficiently than a composition comprising the antigen alone. This more efficient immune response provides increased efficacy in the treatment and/or prevention of any disease, in particular cancer, pathogen, or virus.

The antigen and checkpoint inhibitors, preferably are anti-PD-1 antibody, anti-PD-L1 antibody, anti-LAG-3 antibody, anti-GITR antibody, anti-CD40 antibody, anti-OX40 antibody, anti-CTLA-4 antibody, anti-TIM-3 antibody, and/or anti-4-1BB antibody, of the composition can be administered together or separately to the subject in need thereof. In some instances, the checkpoint inhibitors can be administered separately from the antigen of the composition.

In some embodiments, the checkpoint inhibitors can be administered at least 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, or 96 hours before or after administration of the antigen to the subject. In other embodiments, the PD1 antibody or PDL1 antibody can be administered at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or 90 days before or after administration of the antigen to the subject.

In still other embodiments, the checkpoint inhibitors can be administered at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks before or after administration of the antigen to the subject. In other embodiments, the antibody or antibodies can be administered about 12 hours to about 15 weeks, about 12 hours to about 10 weeks, about 12 hours to about 5 weeks, about 12 hours to about 1 week, about 12 hours to about 60 hours, about 12 hours to about 48 hours, about 24 hours to about 15 weeks, about 60 hours to about 15 weeks, about 96 hours to about 15 weeks, about 1 day to about 15 weeks, about 5 days to about 15 weeks, about 10 days to about 15 weeks, about 15 days to about 15 weeks, about 20 days to about 15 weeks, about 25 days to about 15 weeks, about 30 days to about 15 weeks, about 1 week to about 15 weeks, about 5 weeks to about 15 weeks, or about 10 weeks to about 15 weeks before or after administration of the antigen to the subject.

The composition of the present invention can have features required of effective compositions such as being safe so the composition itself does not cause illness or death; being protective against illness resulting from exposure to live pathogens such as viruses or bacteria; inducing neutralizing antibody to prevent infection of cells; inducing protective T cell against intracellular pathogens; and providing ease of administration, few side effects, biological stability, and low cost per dose. The composition can accomplish some or all of these features by combining the antigen with the checkpoint inhibitors, preferably the anti-PD-1 antibody, anti-PD-L1 antibody, anti-LAG-3 antibody, anti-GITR antibody, anti-CD40 antibody, anti-OX40 antibody, anti-CTLA-4 antibody, anti-TIM-3 antibody, and/or anti-4-1BB antibody as discussed below.

The composition can further modify epitope presentation within the antigen to induce greater immune response to the antigen that a composition comprising the antigen alone. The composition can further induce an immune response when administered to different tissues such as the muscle or the skin.

a. Checkpoint Inhibitors

Checkpoint inhibitors can be any antagonist to the various immune checkpoints, and are preferably antibodies that block immune checkpoints. The antibodies can be a protein including a Fab, monoclonal or polyclonal. The antibodies can also be a DNA expression construct that encodes for and can express functional antibodies. The vaccine can further comprise a PD-1 antibody, PD-L1 antibody, LAG-3 antibody, GITR antibody, CD40 antibody, OX40 antibody, CTLA-4 antibody, TIM-3 antibody, and/or a 4-1BB antibody. The antibody can be a synthetic antibody comprised of DNA sequence encoding at least the variable regions of an immunoglobulin. Such antibody can be generated by identifying or screening for the antibody described above, which is reactive to or binds the antigen described above. The method of identifying or screening for the antibody can use the antigen in methodologies known to those skilled in art to identify or screen for the antibody. Such methodologies can include, but are not limited to, selection of the antibody from a library (e.g., phage display) and immunization of an animal followed by isolation and/or purification of the antibody. See for example methods available in Rajan, S., and Sidhu, S., *Methods in Enzymology*, vol 502, Chapter One "Simplified Synthetic Antibody Libraries (2012), which is incorporated herein in its entirety.

Any antibodies of the invention can also be combined with other checkpoint inhibitor antibodies, including anti-CTLA-4, and others. The checkpoint inhibitors can be a known product such as, for example, ipilimumab, tremelimumab, nivolumab, pembrolizumab, pidilizumab, BMS-936559 (See ClinicalTrials.gov Identifier NCT02028403), MPDL3280A (Roche, see ClinicalTrials.gov Identifier NCT02008227), MDX1105-01 (Bristol Myers Squibb, see ClinicalTrials.gov Identifier NCT00729664), MEDI4736 (MedImmune, See ClinicalTrials.gov Identifier NCT01693562), and MK-3475 (Merck, see ClinicalTrials.gov Identifier NCT02129556).

b. Recombinant Nucleic Acid Sequence Construct

The recombinant nucleic acid sequence can include one or more recombinant nucleic acid sequence constructs. The recombinant nucleic acid sequence construct can include one or more components, which are described in more detail below.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include the heterologous nucleic acid sequence encoding the protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothionein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described above or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human 3-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

c. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described below.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail below.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail below.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A fourth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

d. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

e. Vectors

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA Vectors

In one embodiment, the nucleic acid is an RNA molecule. In one embodiment, the RNA molecule is transcribed from a DNA sequence described herein. For example, in some embodiments, the RNA molecule is encoded by one of SEQ ID NOs:1, 3, 5, 7, 9, 11, 13, 15, 17, 19, 21, 23, 25, 27, or a variant thereof or a fragment thereof. In another embodiment, the nucleotide sequence comprises an RNA sequence transcribed by a DNA sequence encoding the polypeptide sequence of SEQ ID NOs:2, 4, 6, 8, 10, 12, 14, 16, 18, 20, 22, 24, 26, 28, or a variant thereof or a fragment thereof. Accordingly, in one embodiment, the invention provides an RNA molecule encoding one or more of the checkpoint inhibitors disclosed herein. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded.

(4) Circular and Linear Vector

The one or more vectors may be one or more circular plasmids, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The DNA may encode one or more antibodies. The LEC may comprise a promoter, an intron, a stop codon, a polyadenylation signal. The LEC may not contain any antibiotic resistance genes and/or a phosphate backbone. The LEC may not contain other nucleic acid sequences unrelated to the desired gene expression. The LEC is capable of being efficiently delivered to a subject via electroporation and expressing one or more desired antibodies. The LEC may be derived from any plasmid capable of being linearized. These can also be made synthetically without bacterial growth and not from linearized sequences. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be pcrM2. The LEC can be pcrNP. pcrNP and pcrMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector comprises an origin of replication functional in at least one organism, a promoter sequence, convenient restriction endonuclease sites, and one or more selectable markers. (See, e.g., WO 01/96584; WO 01/29058; and U.S. Pat. No. 6,326,193. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described below in more detail.

The one or more vectors can be formulated or manufactured using a combination of known devices and techniques, but preferably they are manufactured using a plasmid manufacturing technique that is described in a licensed, co-pending U.S. provisional application U.S. Ser. No. 60/939, 792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

3. Antibody

As described above, the recombinant nucleic acid sequence can encode the antibody, a fragment thereof, a variant thereof, or a combination thereof. The antibody can bind or react with the antigen, which is described in more detail below.

The antibody can treat, prevent, and/or protect against disease in the subject administered a composition of the invention. The antibody by binding the antigen can treat, prevent, and/or protect against disease in the subject administered the composition. The antibody can promote survival of the disease in the subject administered the composition. In one embodiment, the antibody can provide increased survival of the disease in the subject over the expected survival of a subject having the disease who has not been administered the antibody. In various embodiments, the antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition. In one embodiment, the antibody can provide increased protection against the disease in the subject over the expected protection of a subject who has not been administered the antibody. In various embodiments, the antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment, which comprises both antigen-binding sites. Accordingly, the antibody can be the Fab or F(ab')$_2$. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described below in more detail. The antibody can be a bifunctional antibody as also described below in more detail.

As described above, the antibody can be generated in the subject upon administration of the composition to the subject. The antibody may have a half-life within the subject. In some embodiments, the antibody may be modified to extend or shorten its half-life within the subject. Such modifications are described below in more detail.

The antibody can be defucosylated as described in more detail below.

The antibody may be modified to reduce or prevent antibody-dependent enhancement (ADE) of disease associated with the antigen as described in more detail below.

a. Bispecific Antibody

The recombinant nucleic acid sequence can encode a bispecific antibody, a fragment thereof, a variant thereof, or a combination thereof. The bispecific antibody can bind or react with two antigens, for example, two of the antigens described below in more detail. The bispecific antibody can be comprised of fragments of two of the antibodies described herein, thereby allowing the bispecific antibody to bind or react with two desired target molecules, which may include the antigen, which is described below in more detail, a ligand, including a ligand for a receptor, a receptor, including a ligand-binding site on the receptor, a ligand-receptor complex, and a marker, including a cancer marker.

b. Bifunctional Antibody

The recombinant nucleic acid sequence can encode a bifunctional antibody, a fragment thereof, a variant thereof, or a combination thereof. The bifunctional antibody can bind or react with the antigen described below. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

d. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, O-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

e. Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcγR1a, and thus, the modified antibody does not enhance or cause ADE of disease associated with the antigen, but still neutralizes the antigen.

4. Method of Generating the Synthetic Antibody

The present invention also relates a method of generating the synthetic antibody. The method can include administering the composition to the subject in need thereof by using the method of delivery described in more detail below. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

5. Cancer Antigen

The compositions and methods of the invention can be used in combination with a vaccine comprising an antigen, or fragment or variant thereof.

Markers are known proteins that are present or upregulated vis-à-vis certain cancer cells. By methodology of generating antigens that represent such markers in a way to break tolerance to self, a cancer vaccine can be generated. Such cancer vaccines can include the checkpoint inhibitors to enhance the immune response. The following are some cancer antigens:

a. hTERT hTERT is a human telomerase reverse transcriptase that synthesizes a TTAGGG tag on the end of telomeres to prevent cell death due to chromosomal shortening. Hyperproliferative cells with abnormally high expression of hTERT may be targeted by immunotherapy. Recent studies demonstrate that hTERT expression in dendritic cells transfected with hTERT genes can induce CD8+ cytotoxic T cells and elicit a CD4+ T cells in an antigen-specific fashion.

hTERT can be administered in vectors described herein, and combined with checkpoint inhibitors in various vaccination schedules, including that in the Example, below.

b. Prostate Antigens

The following are antigens capable of eliciting an immune response in a mammal against a prostate antigen. The consensus antigen can comprise epitopes that make them particularly effective as immunogens against prostate cancer cells can be induced. The consensus prostate antigen can comprise the full length translation product, a variant thereof, a fragment thereof or a combination thereof.

The prostate antigens can include one or more of the following: PSA antigen, PSMA antigen, STEAP antigen, PSCA antigen, Prostatic acid phosphatase (PAP) antigen, and other known prostate cancer markers. Proteins may comprise sequences homologous to the prostate antigens, fragments of the prostate antigens and proteins with sequences homologous to fragments of the prostate antigens.

The prostate antigens can be administered in vectors described herein, and combined with checkpoint inhibitors in various vaccination schedules, including that in the Example, below.

c. WT1

The antigen can be Wilm's tumor suppressor gene 1 (WT1), a fragment thereof, a variant thereof, or a combination thereof. WT1 is a transcription factor containing at the N-terminus, a proline/glutamine-rich DNA-binding domain and at the C-terminus, four zinc finger motifs. WT1 plays a role in the normal development of the urogenital system and interacts with numerous factors, for example, p53, a known tumor suppressor and the serine protease HtrA2, which cleaves WT1 at multiple sites after treatment with a cytotoxic drug.

Mutation of WT1 can lead to tumor or cancer formation, for example, Wilm's tumor or tumors expressing WT1. Wilm's tumor often forms in one or both kidneys before metastasizing to other tissues, for example, but not limited to, liver tissue, urinary tract system tissue, lymph tissue, and lung tissue. Accordingly, Wilm's tumor can be considered a metastatic tumor. Wilm's tumor usually occurs in younger children (e.g., less than 5 years old) and in both sporadic and hereditary forms. Accordingly, the vaccine can be used for treating subjects suffering from Wilm's tumor. The vaccine can also be used for treating subjects with cancers or tumors that express WT1 for preventing development of such tumors in subjects. The WT1 antigen can differ from the native, "normal" WT1 gene, and thus, provide therapy or prophylaxis against an WT1 antigen-expressing tumor. Proteins may comprise sequences homologous to the WT1 antigens, fragments of the WT1 antigens and proteins with sequences homologous to fragments of the WT1 antigens.

The WT1 antigens can be administered in vectors described herein, and combined with checkpoint inhibitors in various vaccination schedules, including that in the Example, below.

d. Tyrosinase Antigen

The antigen tyrosinase (Tyr) antigen is an important target for immune mediated clearance by inducing (1) humoral immunity via B cell responses to generate antibodies that block monocyte chemoattractant protein-1 (MCP-1) production, thereby retarding myeloid derived suppressor cells (MDSCs) and suppressing tumor growth; (2) increase cytotoxic T lymphocyte such as $CD8^+$ (CTL) to attack and kill tumor cells; (3) increase T helper cell responses; (4) and increase inflammatory responses via IFN-$\gamma$ and TFN-$\alpha$ or preferably all of the aforementioned.

Tyrosinase is a copper-containing enzyme that can be found in plant and animal tissues. Tyrosinase catalyzes the production of melanin and other pigments by the oxidation of phenols such as tyrosine. In melanoma, tyrosinase can become unregulated, resulting in increased melanin synthesis. Tyrosinase is also a target of cytotoxic T cell recognition in subjects suffering from melanoma. Accordingly, tyrosinase can be an antigen associated with melanoma.

The antigen can comprise protein epitopes that make them particularly effective as immunogens against which anti-Tyr immune responses can be induced. The Tyr antigen can comprise the full length translation product, a variant thereof, a fragment thereof or a combination thereof.

The Tyr antigen can comprise a consensus protein. The Tyr antigen induces antigen-specific T-cell and high titer antibody responses both systemically against all cancer and tumor related cells. As such, a protective immune response is provided against tumor formation by vaccines comprising the Tyr consensus antigen. Accordingly, any user can design a vaccine of the present invention to include a Tyr antigen to provide broad immunity against tumor formation, metastasis of tumors, and tumor growth. Proteins may comprise sequences homologous to the Tyr antigens, fragments of the Tyr antigens and proteins with sequences homologous to fragments of the Tyr antigens.

The Tyr antigens can be administered in vectors described herein, and combined with checkpoint inhibitors in various vaccination schedules, including that in the Example, below.

e. NYES01

NY-ESO-1 is a cancer-testis antigen expressed in various cancers where it can induce both cellular and humoral immunity. Gene expression studies have shown upregulation of the gene for NY-ESO-1, CTAG1B, in myxoid and round cell liposarcomas. Proteins may comprise sequences homologous to the NYES01 antigens, fragments of the NYES01 antigens and proteins with sequences homologous to fragments of the NYES01 antigens.

The NYES01 antigens can be administered in vectors described herein, and combined with checkpoint inhibitors in various vaccination schedules, including that in the Example, below.

f. PRAME

Melanoma antigen preferentially expressed in tumors (PRAME antigen) is a protein that in humans is encoded by the PRAME gene. This gene encodes an antigen that is predominantly expressed in human melanomas and that is recognized by cytolytic T lymphocytes. It is not expressed in normal tissues, except testis. The gene is also expressed in acute leukemias. Five alternatively spliced transcript variants encoding the same protein have been observed for this gene. Proteins may comprise sequences homologous to the PRAME antigens, fragments of the PRAME antigens and proteins with sequences homologous to fragments of the PRAME antigens.

The PRAME antigens can be administered in vectors described herein, and combined with checkpoint inhibitors in various vaccination schedules, including that in the Example, below.

g. MAGE

MAGE stands for Melanoma-associated Antigen, and in particular melanoma associated antigen 4 (MAGEA4). MAGE-A4 is expressed in male germ cells and tumor cells of various histological types such as gastrointestinal, esophageal and pulmonary carcinomas. MAGE-A4 binds the oncoprotein, Gankyrin. This MAGE-A4 specific binding is mediated by its C-terminus. Studies have shown that exogenous MAGE-A4 can partly inhibit the adhesion-independent growth of Gankyrin-overexpressing cells in vitro and suppress the formation of migrated tumors from these cells in nude mice. This inhibition is dependent upon binding between MAGE-A4 and Gankyrin, suggesting that interactions between Gankyrin and MAGE-A4 inhibit Gankyrin-mediated carcinogenesis. It is likely that MAGE expression in tumor tissue is not a cause, but a result of tumor genesis, and MAGE genes take part in the immune process by targeting early tumor cells for destruction.

Melanoma-associated antigen 4 protein (MAGEA4) can be involved in embryonic development and tumor transformation and/or progression. MAGEA4 is normally expressed in testes and placenta. MAGEA4, however, can be expressed in many different types of tumors, for example, melanoma, head and neck squamous cell carcinoma, lung carcinoma, and breast carcinoma. Accordingly, MAGEA4 can be antigen associated with a variety of tumors.

The MAGEA4 antigen can induce antigen-specific T cell and/or high titer antibody responses, thereby inducing or eliciting an immune response that is directed to or reactive against the cancer or tumor expressing the antigen. In some embodiments, the induced or elicited immune response can be a cellular, humoral, or both cellular and humoral immune responses. In some embodiments, the induced or elicited cellular immune response can include induction or secretion of interferon-gamma (IFN-γ) and/or tumor necrosis factor alpha (TNF-α). In other embodiments, the induced or elicited immune response can reduce or inhibit one or more immune suppression factors that promote growth of the tumor or cancer expressing the antigen, for example, but not limited to, factors that down regulate MHC presentation, factors that up regulate antigen-specific regulatory T cells (Tregs), PD-L1, FasL, cytokines such as IL-10 and TFG-3, tumor associated macrophages, tumor associated fibroblasts.

The MAGEA4 antigen can comprise protein epitopes that make them particularly effective as immunogens against which anti-MAGEA4 immune responses can be induced. The MAGEA4 antigen can comprise the full length translation product, a variant thereof, a fragment thereof or a combination thereof. The MAGEA4 antigen can comprise a consensus protein.

The nucleic acid sequence encoding the consensus MAGEA4 antigen can be optimized with regards to codon usage and corresponding RNA transcripts. The nucleic acid encoding the consensus MAGEA4 antigen can be codon and RNA optimized for expression. In some embodiments, the nucleic acid sequence encoding the consensus MAGEA4 antigen can include a Kozak sequence (e.g., GCC ACC) to increase the efficiency of translation. The nucleic acid encoding the consensus MAGEA4 antigen can include multiple stop codons (e.g., TGA TGA) to increase the efficiency of translation termination.

The MAGE antigens can be administered in vectors described herein, and combined with checkpoint inhibitors in various vaccination schedules, including that in the Example, below.

h. Tumor Antigen

In the context of the present invention, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), 3-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3CA 27.29BCAA, CA 195, CA 242, CA-50, CAM43, CD68P1, CO-029, FGF-5, G250, Ga733EpCAM, HTgp-175, M344, MA-50, MG7-Ag, MOV18, NB/70K, NY-CO-1, RCAS1, SDCCAG16, TA-90Mac-2 binding proteincyclophilin C-associated protein, TAAL6, TAG72, TLP, and TPS.

a. Excipients and Other Components of the Vaccine

The vaccine may further comprise a pharmaceutically acceptable excipient. The pharmaceutically acceptable excipient can be functional molecules such as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to the checkpoint inhibitor antibodies of the invention. The additional adjuvant can be other genes that are expressed in an alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, PD-1, IL-10, IL-12, IL-18, or a combination thereof.

Other genes that can be useful as adjuvants in addition to the antibodies of the invention include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

6. Method of Vaccination

The present invention is also directed to a method of increasing an immune response in a subject. Increasing the immune response can be used to treat and/or prevent disease in the subject. The method can include administering the herein disclosed vaccine to the subject. The subject administered the vaccine can have an increased or boosted immune response as compared to a subject administered the antigen alone. In some embodiments, the immune response can be increased by about 0.5-fold to about 15-fold, about 0.5-fold to about 10-fold, or about 0.5-fold to about 8-fold. Alternatively, the immune response in the subject administered the vaccine can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the vaccine can be increased about 50% to about 1500%, about 50% to about 1000%, or about 50% to about 800%. In other embodiments, the immune response in the subject administered the vaccine can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The vaccine dose can be between 1 µg to 10 mg active component/kg body weight/time, and can be 20 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

a. Administration

The composition of the invention can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The composition of the invention can be administered prophylactically or therapeutically. In prophylactic administration, the vaccines can be administered in an amount sufficient to induce an immune response. In therapeutic applications, the compositions of the invention are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The composition of the invention can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the composition of the invention can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The composition of the invention can be delivered via a variety of routes. Typical delivery routes include parenteral administration, e.g., intradermal, intramuscular or subcutaneous delivery. Other routes include oral administration, intranasal, and intravaginal routes. For the DNA of the composition of the invention in particular, the composition can be delivered to the interstitial spaces of tissues of an individual (Felgner et al., U.S. Pat. Nos. 5,580,859 and 5,703,055, the contents of all of which are incorporated herein by reference in their entirety). The composition can also be administered to muscle, or can be administered via intradermal or subcutaneous injections, or transdermally, such as by iontophoresis. Epidermal administration of the composition can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The composition of the invention can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The composition of the invention can be a liquid preparation such as a suspension, syrup or elixir. The composition of the invention can also be a preparation for parenteral, subcutaneous, intradermal, intramuscular or intravenous administration (e.g., injectable administration), such as a sterile suspension or emulsion.

The composition of the invention can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The composition of the invention can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired composition of the invention in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Plymouth Meeting, PA) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

7. Cancer Therapy

The invention provides methods of treating or preventing cancer, or of treating and preventing metastasis of tumors. Related aspects of the invention provide methods of preventing, aiding in the prevention, and/or reducing metastasis of hyperplastic or tumor cells in an individual.

One aspect of the invention provides a method of inhibiting metastasis in an individual in need thereof, the method comprising administering to the individual an effective amount of a composition of the invention. The invention further provides a method of inhibiting metastasis in an individual in need thereof, the method comprising administering to the individual an effective metastasis-inhibiting amount of any one of the compositions described herein.

In some embodiments of treating or preventing cancer, or of treating and preventing metastasis of tumors in an individual in need thereof, a second agent is administered to the individual, such as an antineoplastic agent. In some embodiments, the second agent comprises a second metastasis-inhibiting agent, such as a plasminogen antagonist, or an adenosine deaminase antagonist. In other embodiments, the second agent is an angiogenesis inhibiting agent.

The compositions of the invention can be used to prevent, abate, minimize, control, and/or lessen cancer in humans and animals. The compositions of the invention can also be used to slow the rate of primary tumor growth. The compositions of the invention when administered to a subject in need of treatment can be used to stop the spread of cancer cells. As such, the compositions of the invention can be administered as part of a combination therapy with one or more drugs or other pharmaceutical agents. When used as part of the combination therapy, the decrease in metastasis and reduction in primary tumor growth afforded by the compositions of the invention allows for a more effective and efficient use of any pharmaceutical or drug therapy being used to treat the patient. In addition, control of metastasis by the compositions of the invention affords the subject a greater ability to concentrate the disease in one location.

In one embodiment, the invention provides methods for preventing metastasis of malignant tumors or other cancerous cells as well as to reduce the rate of tumor growth. The methods comprise administering an effective amount of one or more of the compositions of the invention to a subject diagnosed with a malignant tumor or cancerous cells or to a subject having a tumor or cancerous cells.

The following are non-limiting examples of cancers that can be treated by the methods and compositions of the invention: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocvtoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

In one embodiment, the invention provides a method to treat cancer metastasis comprising treating the subject prior to, concurrently with, or subsequently to the treatment with a composition of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cisplatinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

The compounds of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the invention include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the compositions of the invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine;

carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

The present invention has multiple aspects, illustrated by the following non-limiting examples.

8. Examples

Example 1

In Vivo Expression of Plasmid Encoded IgG for PD-1 or LAG-3 by Synthetic DNA as a New Tool for Cancer Immunotherapy Cancers employ various strategies to escape immune surveillance including the exploitation of immune checkpoints. Immune checkpoints are receptors found on immune and stromal cells whose function can impact the duration or potency of an immune response. Tumor cells often upregulate ligands for these receptors to protect themselves from the host immune response. Monoclonal antibody (MAb) therapeutics which block immune checkpoint-ligand interactions restore T cell destruction of cancer cells in vivo. MAbs that target the inhibitory T cell signaling mediated by CTLA-4 and/or PD-1 have recently gained regulatory approval for the treatment of some cancers based on remarkable clinical outcomes.

The results presented herein focus on a new method to improve MAb delivery through direct engineering of MAb in the form of synthetic DNA plasmids. This technology can improve many aspects of such a therapy by lowering cost, increasing in vivo expression times and allowing for simple combination formulations in the absence of a host anti-vector immune response, extending use of these groundbreaking therapies to disadvantaged patient populations.

The results demonstrate that "enhanced and optimized" DNA plasmid technology can be used to direct in vivo production of immunoglobulin heavy and light chains of established monoclonal antibodies which can target the immune checkpoints LAG3 and PD-1 as determined in flow cytometry, ELISA and western blot assays. Both antibodies are produced at physiologically relevant levels in blood and other tissues of mice using electroporation-enhanced delivery of DNA plasmids encoding genes for each antibody. Serum antibodies from inoculated animals retain the ability to bind to their targets and are bioactive in vivo and exhibit immune stimulatory effects for host T cells. These studies have significant implications for prophylactic and therapeutic strategies for cancer and other important diseases.

Construction of PD-1, PD-L1, LAG-3, GITR, CD40, OX40, CTLA-4, TIM-3, and 4-1BB dMAb Plasmids and Confirmation of In Vitro and In Vivo IgG Production DNA monoclonal antibody (dMAb) plasmids were constructed by cloning the sequences for the heavy and light chains of human monoclonal antibodies into the pVAX1 plasmid.

TABLE 1

Sequences

| SEQ ID | Identifier |
| --- | --- |
| SEQ ID NO: 1 | Anti-hPD-1 optimized nucleic acid sequence (DNA) |
| SEQ ID NO: 2 | Anti-hPD-1 optimized amino acid sequence (protein) |
| SEQ ID NO: 3 | Anti-hLAG3 nucleic acid sequence (DNA) |
| SEQ ID NO: 4 | Anti-hLAG3 amino acid sequence (protein) |
| SEQ ID NO: 5 | DMab TIM-3 nucleic acid sequence (DNA) |
| SEQ ID NO: 6 | Human TIM-3 (protein) |
| SEQ ID NO: 7 | DMab Human PD-1 nucleic acid sequence (DNA) |
| SEQ ID NO: 8 | Human PD-1 (protein) |
| SEQ ID NO: 9 | Mouse LAG3-IgG1 (DNA) |
| SEQ ID NO: 10 | Mouse Lag3-IgG1 (protein) |
| SEQ ID NO: 11 | Human 4-1BB-IgG1 (DNA) |
| SEQ ID NO: 12 | Human 4-lBB-IgG1 amino acid (protein) |
| SEQ ID NO: 13 | Human OX40-IgG1-Agonist (Humanized from mouse anti-human OX-40) (DNA) |
| SEQ ID NO: 14 | Human OX-40-IgG1 (protein) |
| SEQ ID NO: 15 | Human GITR (Clone 36E5) (DNA) |
| SEQ ID NO: 16 | Human GITR (protein) |
| SEQ ID NO: 17 | Human CD40(Clone #G12) (DNA) |
| SEQ ID NO: 18 | Human CD40(Clone #G12) (protein) |
| SEQ ID NO: 19 | Human CD27 (Agonistic) (DNA) |
| SEQ ID NO: 20 | Human CD27 Amino Acid Sequence (protein) |
| SEQ ID NO: 21 | Tremelimumab (full-length) (DNA) |
| SEQ ID NO: 22 | Tremelimumab (full-length) Amino Acid Sequence (protein) |
| SEQ ID NO: 23 | Tremelimumab (frame) (DNA) |
| SEQ ID NO: 24 | Tremelimumab (frame) Amino Acid Sequence (protein) |
| SEQ ID NO: 25 | Ipilimumab (full-length) (DNA) |
| SEQ ID NO: 26 | Ipilimumab (full-length) Amino Acid Sequence (protein) |
| SEQ ID NO: 27 | Ipilimumab (frame) (DNA) |
| SEQ ID NO: 28 | Ipilimumab (frame) Amino Acid Sequence (protein) |

Supernatants from plasmid-transfected 293T cells were collected at 48 hours post transfection and levels of human IgG assayed using enzyme-linked immunosorbent assay (ELISA).

Nu/J mice (n=4, PD-1 or n=5, LAG-3) were injected with 100 μg plasmid followed by electroporation (EP). Sera was collected from mice for up to 35 days and ELISA used to quantitate human IgG levels.

In Vivo Produced IgG Following PD-1 or LAG-3 dMAB Plasmid Administration Bind Specifically to their Targets Dilutions of sera from mice injected with pVAX1, PD-1 dMAb, or LAG-3 dMAb plasmids were evaluated in a binding ELISA using recombinant PD-1 or LAG-3 protein. Specific binding of PD-1 dMAb and LAG-3 dMAb to recombinant PD-1 or recombinant LAG-3 protein was evaluated with Western analyses.

PHA-stimulated T lymphocytes were incubated with sera from pVAX1 or dMAb plasmid-injected mice followed by fluorophore-conjugated anti-human IgG secondary antibody. Stained cells were evaluated by flow cytometry with gating on live, CD3+ cells. Commercial anti-PD1 and anti-LAG-3 antibodies were used as positive controls.

LAG-3 dMAb Impedes Tumor Growth, Improves Survival, and Promote a Less Inhibitory Tumor Microenvironment.

Cohorts of female C57BL/6 mice were implanted subcutaneously in their right flank with 5×105 B16 F10 melanoma cells and subsequently injected 5 days later with empty pVAX1 or LAG-3 dMAb plasmid. Caliper measurement of tumors and mouse survival were evaluated up to one month post tumor implantation.

To elucidate the role of LAG-3 dMAb in regulatory T cell (Treg)-mediated immune suppression, flow cytometry was used to analyze the population of LAG3+FoxP3+CD25+ Treg cells in the tumor and in peritumoral tissues 23 days after inoculation of B16 melanoma cells into C57BL/6 mice.

Plasmids encoding the genetic sequence of antibodies targeting the immune checkpoint molecules were able to direct in vitro and in vivo antibody production.

Human anti-PD-1, anti-LAG-3, anti-GITR, and anti-4-1BB dMAbs produced in mice bound specifically to their targets.

Anti-LAG-3 dMAbs were able to impede tumor growth, improve survival, and promoted a less inhibitory tumor microenvironment in a B16 melanoma tumor challenge model.

DNA plasmids delivered intramuscularly with electroporation can drive robust in vivo antibody production and provides a serology-independent, cost-effective platform for delivering monoclonal antibody therapeutics targeting cancer, infectious diseases, and other conditions.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for generating a synthetic antibody in a subject comprising one or more nucleic acid molecules encoding one or more antibodies or fragments thereof, wherein the one or more antibodies or fragments target at least one immune checkpoint molecule selected from the group consisting of PD-1, LAG-3, PD-L1, GITR, CD40, OX40, CTLA-4, TIM-3, 4-1BB, and a combination thereof, wherein the one or more nucleic acid molecules comprises a nucleotide sequence encoding an amino acid sequence having at least about 80% identity over the entire length of an amino acid sequence selected from the group consisting of SEQ ID NOs: 2, 4, 6, 8, 10, 12, 14, 16, 18, 20, 22, 24, 26, and 28, wherein said amino acid sequence comprises heavy and light chain CDR amino acid sequences selected from the group consisting of SEQ ID Nos: 2, 4, 6, 8, 10, 12, 14, 16, 18, 20, 22, 24, 26, and 28.

2. The composition of claim 1, comprising a nucleotide sequence encoding a cleavage domain.

3. The composition of claim 1, comprising a nucleotide sequence encoding a variable heavy chain region and a variable light chain region of the antibody.

4. The composition of claim 1, comprising a nucleotide sequence encoding a constant heavy chain region of human IgG1 and a constant kappa light chain region.

5. The composition of claim 1, comprising a nucleotide sequence encoding a polypeptide comprising a variable heavy chain region of the antibody; a constant heavy chain region of human IgG; a cleavage domain; a variable light chain region of the antibody; and a constant kappa light chain region.

6. The composition of claim 1, wherein the nucleotide sequence encodes a leader sequence.

7. The composition of claim 1, comprising a nucleotide sequence having at least about 80% identity over the entire length of the nucleic acid sequence of at least one nucleic acid sequence selected from the group of SEQ ID NOs: 1, 3, 5, 7, 9, 11, 13, 15, 17, 19, 21, 23, 25, and 27.

8. The composition of claim 1, wherein the one or more nucleic acid molecules are engineered to be in an expression vector.

9. The composition of claim 1, further comprising a nucleotide sequence encoding an antigen.

10. The composition of claim 9, wherein the antigen is a cancer antigen.

11. The composition of claim 1, further comprising a pharmaceutically acceptable excipient.

12. A method of treating a disease in a subject, the method comprising administering to the subject the composition of claim 1.

13. The method of claim 12, wherein the disease is cancer.

14. A method for increasing an immune response in a subject in need thereof, the method comprising administering the composition of claim 1 to the subject.

15. The method of claim 14, wherein administering the composition comprises an electroporating step.

16. A composition for generating a synthetic antibody in a subject comprising one or more nucleic acid molecules encoding one or more antibodies or fragments thereof, wherein the one or more antibodies or fragments target at least one immune checkpoint molecule selected from the group consisting of PD-1, LAG-3, PD-L1, GITR, CD40, OX40, CTLA-4, TIM-3, 4-1BB, and a combination thereof, wherein the one or more nucleic acid molecules comprises a nucleotide sequence encoding an amino acid sequence having at least about 90% identity over the entire length of at least one amino acid sequence selected from the group consisting of SEQ ID NOs: 2, 4, 6, 8, 10, 12, 14, 16, 18, 20, 22, 24, 26, and 28, wherein said amino acid sequence comprises the heavy and light chain CDRs of an amino acid sequence selected from the group consisting of SEQ ID Nos: 2, 4, 6, 8, 10, 12, 14, 16, 18, 20, 22, 24, 26, and 28.

* * * * *

SEQUENCE LISTING

<160> NUMBER OF SEQ ID NOS: 28

<210> SEQ ID NO 1
<211> LENGTH: 2166
<212> TYPE: DNA
<213> ORGANISM: Artificial Sequence
<220> FEATURE:
<223> OTHER INFORMATION: Anti-hPD-1 optimized nucleic acid sequence

<400> SEQUENCE: 1

| | | | | | |
|---|---|---|---|---|---|
| atggactgga | cttggcgcat | tctgtttctg | gtcgccgctg | ctactggaac | tcacgctcag | 60 |
| gtgcagctgg | tcgaatcagg | aggggcgtg | gtccagccag | gccgaagcct | gaggctggac | 120 |
| tgcaaggcct | ccggaatcac | cttctcaaac | agcggaatgc | actgggtgcg | ccaggctcct | 180 |
| gggaaaggac | tggagtgggt | cgcagtgatc | tggtacgacg | gtcaaagcg | atactatgct | 240 |
| gatagcgtga | aaggcagatt | cactatttca | cgggacaaca | gcaagaatac | cctgtttctg | 300 |
| cagatgaaca | gcctgcgggc | tgaggatacc | gcagtgtact | attgtgcaac | aaatgacgat | 360 |
| tactggggac | aggggacccct | ggtcacagtg | agctccgcta | gtaccaaggg | gccctcagtg | 420 |
| tttcccctgg | caccttgctc | ccgctctact | agtgagtcaa | ccgccgctct | gggctgtctg | 480 |
| gtgaaagatt | atttccccga | acctgtcaca | gtgtcatgga | atagcggggc | actgaccagc | 540 |
| ggcgtccaca | catttcctgc | cgtgctgcag | tctagtgggc | tgtacagcct | gtcaagcgtg | 600 |
| gtcacagtcc | cttcctctag | tctgggcact | aagacctata | catgcaacgt | ggaccataaa | 660 |
| ccatccaata | ctaaggtcga | taaaagggtg | gagtctaagt | acggaccccc | ttgcccaccc | 720 |
| tgtccagcac | ccgaattcct | gggcggacca | agcgtgttcc | tgtttcctcc | aaagcccaaa | 780 |
| gacacccctga | tgatctccag | aacacctgag | gtcacttgcg | tggtcgtgga | cgtgtctcag | 840 |
| gaggaccccg | aagtccagtt | caactggtac | gtggatggcg | tcgaagtgca | caatgctaag | 900 |
| acaaaaccca | gggaggaaca | gtttaacagc | acatacaggg | tcgtgtccgt | cctgactgtg | 960 |
| ctgcatcagg | actggctgaa | cggaaaggag | tataagtgca | aagtgagcaa | taaggggctg | 1020 |
| ccatcaagca | tcgagaaaac | cattagcaag | gccaaaggcc | agccacggga | accccaggtg | 1080 |
| tacacactgc | cccctagcca | ggaggaaatg | actaagaacc | aggtcagcct | gacctgtctg | 1140 |
| gtgaaaggct | tctatccttc | tgacattgct | gtggagtggg | aaagtaatgg | acagccagag | 1200 |
| aacaattaca | agaccacacc | cccgtcctg | gactccgatg | gctctttctt | tctgtattcc | 1260 |
| aggctgaccg | tggataaatc | tagatggcag | gagggaaacg | tctttagctg | ctccgtgatg | 1320 |
| cacgaagccc | tgcacaatca | ttacacccag | aagtctctga | gtctgtcact | gggaaagcga | 1380 |
| ggacgaaaaa | ggagaagcgg | ctccggagcc | acaaacttct | ccctgctgaa | gcaggctggc | 1440 |
| gacgtggagg | aaaatcctgg | accaatggtc | ctgcagactc | aggtgtttat | ctctctgctg | 1500 |
| ctgtggatta | gtggcgccta | cggagagatc | gtgctgactc | agtcccccgc | taccctgtct | 1560 |
| ctgagtcctg | gcgaacgcgc | aaccctgtct | tgtcgagcct | cacagagcgt | gtcctcttac | 1620 |
| ctggcatggt | atcagcagaa | gcctggacag | gccccaaggc | tgctgatcta | tgatgcctct | 1680 |
| aaccgggcta | cagggattcc | cgcacgcttc | tccgggtctg | gcagtggaac | tgactttact | 1740 |
| ctgaccatta | gttcactgga | gccagaagat | ttcgccgtgt | actattgcca | gcagagctcc | 1800 |
| aattggccca | gaacatttgg | gcagggcact | aaggtggaga | tcaaacgac | tgtcgcagcc | 1860 |
| ccaagcgtgt | tcatctttcc | tccatcagac | gaacagctga | gtccggaac | cgcctctgtg | 1920 |
| gtgtgcctgc | tgaacaattt | ctaccccaga | gaggctaagg | tccagtggaa | agtggataac | 1980 |
| gcactgcaga | gtgggaattc | acaggagagc | gtgaccgaac | aggactccaa | ggattctaca | 2040 |

```
tatagtctgt ctagtacact gactctgtcc aaagccgact acgagaagca taaagtgtat    2100
gcttgcgaag tcactcacca ggggctgcga agtcccgtca ctaagtcttt caatagagga    2160
gaatgt                                                               2166
```

<210> SEQ ID NO 2
<211> LENGTH: 722
<212> TYPE: PRT
<213> ORGANISM: Artificial Sequence
<220> FEATURE:
<223> OTHER INFORMATION: Anti-hPD-1 optimized amino acid sequence

<400> SEQUENCE: 2

```
Met Asp Trp Thr Trp Arg Ile Leu Phe Leu Val Ala Ala Thr Gly
1               5                   10                  15

Thr His Ala Gln Val Gln Leu Val Glu Ser Gly Gly Gly Val Val Gln
            20                  25                  30

Pro Gly Arg Ser Leu Arg Leu Asp Cys Lys Ala Ser Gly Ile Thr Phe
        35                  40                  45

Ser Asn Ser Gly Met His Trp Val Arg Gln Ala Pro Gly Lys Gly Leu
    50                  55                  60

Glu Trp Val Ala Val Ile Trp Tyr Asp Gly Ser Lys Arg Tyr Tyr Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Thr Asn Asp Asp Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335
```

```
Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly Lys Arg Gly Arg Lys Arg
    450                 455                 460

Arg Ser Gly Ser Gly Ala Thr Asn Phe Ser Leu Leu Lys Gln Ala Gly
465                 470                 475                 480

Asp Val Glu Glu Asn Pro Gly Pro Met Val Leu Gln Thr Gln Val Phe
                485                 490                 495

Ile Ser Leu Leu Leu Trp Ile Ser Gly Ala Tyr Gly Glu Ile Val Leu
            500                 505                 510

Thr Gln Ser Pro Ala Thr Leu Ser Leu Ser Pro Gly Glu Arg Ala Thr
        515                 520                 525

Leu Ser Cys Arg Ala Ser Gln Ser Val Ser Ser Tyr Leu Ala Trp Tyr
    530                 535                 540

Gln Gln Lys Pro Gly Gln Ala Pro Arg Leu Leu Ile Tyr Asp Ala Ser
545                 550                 555                 560

Asn Arg Ala Thr Gly Ile Pro Ala Arg Phe Ser Gly Ser Gly Ser Gly
                565                 570                 575

Thr Asp Phe Thr Leu Thr Ile Ser Ser Leu Glu Pro Glu Asp Phe Ala
            580                 585                 590

Val Tyr Tyr Cys Gln Gln Ser Ser Asn Trp Pro Arg Thr Phe Gly Gln
        595                 600                 605

Gly Thr Lys Val Glu Ile Lys Arg Thr Val Ala Ala Pro Ser Val Phe
    610                 615                 620

Ile Phe Pro Pro Ser Asp Glu Gln Leu Lys Ser Gly Thr Ala Ser Val
625                 630                 635                 640

Val Cys Leu Leu Asn Asn Phe Tyr Pro Arg Glu Ala Lys Val Gln Trp
                645                 650                 655

Lys Val Asp Asn Ala Leu Gln Ser Gly Asn Ser Gln Glu Ser Val Thr
            660                 665                 670

Glu Gln Asp Ser Lys Asp Ser Thr Tyr Ser Leu Ser Ser Thr Leu Thr
        675                 680                 685

Leu Ser Lys Ala Asp Tyr Glu Lys His Lys Val Tyr Ala Cys Glu Val
    690                 695                 700

Thr His Gln Gly Leu Arg Ser Pro Val Thr Lys Ser Phe Asn Arg Gly
705                 710                 715                 720

Glu Cys

<210> SEQ ID NO 3
<211> LENGTH: 2187
<212> TYPE: DNA
```

<213> ORGANISM: Artificial Sequence
<220> FEATURE:
<223> OTHER INFORMATION: Anti-hLAG3 nucleic acid sequence

<400> SEQUENCE: 3

| | | | | | |
|---|---|---|---|---|---|
| atggattgga | cttggagaat | tctgtttctg | gtcgccgccg | ctaccgggac | acacgctcag | 60 |
| gtgcagctgc | agcagtgggg | ggcaggactg | ctgaagccaa | gtgagactct | gtcactgacc | 120 |
| tgcgccgtgt | acggcggatc | attcagcgac | tactattgga | actggatcag | gcagccccct | 180 |
| ggaaagggc | tggagtggat | cggcgaaatt | aataccggg | gatcaaccaa | cagcaatccc | 240 |
| tccctgaaat | ctcgcgtgac | actgagcctg | gacacttcca | gaaccagtt | ttcactgaaa | 300 |
| ctgcgaagcg | tcacagccgc | tgatactgca | gtgtactatt | gtgccttcgg | ctacagcgac | 360 |
| tacgagtata | attggtttga | tccctggggc | cagggaaccc | tggtcacagt | gagctccgct | 420 |
| tccaccaagg | gaccttctgt | gttcccactg | gcaccctgct | ccaggtctac | cagtgagtca | 480 |
| acagcagccc | tggggtgtct | ggtgaaagat | tatttcccag | aacccgtcac | agtgagttgg | 540 |
| aactcaggag | cactgaccag | cggggtccac | acatttcccg | ccgtgctgca | gtctagtgga | 600 |
| ctgtacagcc | tgtcaagcgt | ggtcactgtc | ccatcctcta | gtctggggac | taagacctat | 660 |
| acatgcaacg | tggaccataa | acccagtaat | accaaggtcg | ataaaagagt | ggagtctaag | 720 |
| tacggaccac | catgccctcc | atgtcctgca | ccagaattcc | tgggggcc | tagcgtgttc | 780 |
| ctgtttcccc | ctaagccaaa | agacaccctg | atgatctccc | ggactccaga | ggtcacctgt | 840 |
| gtggtcgtgg | acgtgtctca | ggaggacccc | gaagtccagt | tcaactggta | cgtggatggc | 900 |
| gtcgaagtgc | acaatgccaa | gacaaaaccc | agggaggaac | agtttaatag | tacttacaga | 960 |
| gtcgtgtcag | tcctgaccgt | gctgcatcag | gactggctga | acggaaagga | gtataagtgc | 1020 |
| aaagtgagca | taaggggct | gccttcaagc | atcgagaaaa | caattagcaa | ggccaaaggc | 1080 |
| cagcctcggg | aaccacaggt | gtacactctg | ccacccagcc | aggaggaaat | gactaagaac | 1140 |
| caggtcagcc | tgcatgtgtct | ggtgaaaggg | ttctatccct | ccgacattgc | tgtggagtgg | 1200 |
| gaatctaatg | ccagcctga | gaacaattac | aagaccacac | ctccagtgct | ggacagcgat | 1260 |
| gggtccttct | ttctgtattc | tagactgacc | gtggataaaa | gtcggtggca | ggagggcaac | 1320 |
| gtctttagct | gctccgtgat | gcatgaagcc | ctgcacaatc | attacacaca | gaagtctctg | 1380 |
| agtctgtcac | tggcaagcg | gggacgcaaa | aggagaagcg | ggtccggcgc | cactaacttc | 1440 |
| tccctgctga | agcaggctgg | ggacgtggag | gaaaatcccg | ccctatggt | cctgcagaca | 1500 |
| caggtgttta | tcagcctgct | gctgtggatt | tccggggcct | acggcgagat | cgtgctgact | 1560 |
| cagtccccag | ctaccctgtc | tctgagtccc | ggcgaacgag | ctaccctgtc | ttgtagggca | 1620 |
| tcacagagca | tttcctctta | cctggcatgg | tatcagcaga | agccaggaca | ggcacctcga | 1680 |
| ctgctgatct | atgatgccag | caaccgcgct | actggaattc | ctgcacgatt | ctccggatct | 1740 |
| gggagtggca | ccgactttac | tctgaccatc | agttcactgg | agcctgaaga | tttcgctgtg | 1800 |
| tactattgcc | agcagcgatc | caactggcca | ctgacatttg | gacagggggac | taatctggag | 1860 |
| atcaagagga | ccgtcgctgc | accttcagtg | ttcatttttc | cccctagcga | cgaacagctg | 1920 |
| aaatctggca | cagccagtgt | cgtgtgtctg | ctgaacaatt | tctacccaag | ggaggctaag | 1980 |
| gtccagtgga | agtggataa | cgcactgcag | tctggaaata | gtcaggagtc | agtgacagaa | 2040 |
| caggacagca | aggattccac | ttattctctg | agctccacac | tgactctgtc | caaagccgac | 2100 |
| tacgagaagc | acaaagtcta | tgcttgcgaa | gtgacccatc | agggcctgtc | tagtccagtg | 2160 |
| acaaagtctt | ttaacagagg | agagtgt | | | | 2187 |

<210> SEQ ID NO 4
<211> LENGTH: 729
<212> TYPE: PRT
<213> ORGANISM: Artificial Sequence
<220> FEATURE:
<223> OTHER INFORMATION: Anti-hLAG3 amino acid sequence

<400> SEQUENCE: 4

```
Met Asp Trp Thr Trp Arg Ile Leu Phe Leu Val Ala Ala Ala Thr Gly
1               5                   10                  15

Thr His Ala Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Asp Tyr Tyr Trp Asn Trp Ile Arg Gln Pro Pro Gly Lys Gly Leu
    50                  55                  60

Glu Trp Ile Gly Glu Ile Asn His Arg Gly Ser Thr Asn Ser Asn Pro
65                  70                  75                  80

Ser Leu Lys Ser Arg Val Thr Leu Ser Leu Asp Thr Ser Lys Asn Gln
                85                  90                  95

Phe Ser Leu Lys Leu Arg Ser Val Thr Ala Ala Asp Thr Ala Val Tyr
            100                 105                 110

Tyr Cys Ala Phe Gly Tyr Ser Asp Tyr Glu Tyr Asn Trp Phe Asp Pro
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Lys Thr Tyr Thr Cys Asn Val
    210                 215                 220

Asp His Lys Pro Ser Asn Thr Lys Val Asp Lys Arg Val Glu Ser Lys
225                 230                 235                 240

Tyr Gly Pro Pro Cys Pro Pro Cys Pro Ala Pro Glu Phe Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser Gln Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Gly Leu Pro Ser Ser Ile Glu
            340                 345                 350

Lys Thr Ile Ser Lys Ala Lys Gly Gln Pro Arg Glu Pro Gln Val Tyr
        355                 360                 365
```

Thr Leu Pro Pro Ser Gln Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Arg Leu Thr Val Asp
            420                 425                 430

Lys Ser Arg Trp Gln Glu Gly Asn Val Phe Ser Cys Ser Val Met His
        435                 440                 445

Glu Ala Leu His Asn His Tyr Thr Gln Lys Ser Leu Ser Leu Ser Leu
    450                 455                 460

Gly Lys Arg Gly Arg Lys Arg Arg Ser Gly Ser Gly Ala Thr Asn Phe
465                 470                 475                 480

Ser Leu Leu Lys Gln Ala Gly Asp Val Glu Glu Asn Pro Gly Pro Met
                485                 490                 495

Val Leu Gln Thr Gln Val Phe Ile Ser Leu Leu Leu Trp Ile Ser Gly
            500                 505                 510

Ala Tyr Gly Glu Ile Val Leu Thr Gln Ser Pro Ala Thr Leu Ser Leu
        515                 520                 525

Ser Pro Gly Glu Arg Ala Thr Leu Ser Cys Arg Ala Ser Gln Ser Ile
530                 535                 540

Ser Ser Tyr Leu Ala Trp Tyr Gln Gln Lys Pro Gly Gln Ala Pro Arg
545                 550                 555                 560

Leu Leu Ile Tyr Asp Ala Ser Asn Arg Ala Thr Gly Ile Pro Ala Arg
                565                 570                 575

Phe Ser Gly Ser Gly Ser Gly Thr Asp Phe Thr Leu Thr Ile Ser Ser
            580                 585                 590

Leu Glu Pro Glu Asp Phe Ala Val Tyr Tyr Cys Gln Gln Arg Ser Asn
        595                 600                 605

Trp Pro Leu Thr Phe Gly Gln Gly Thr Asn Leu Glu Ile Lys Arg Thr
    610                 615                 620

Val Ala Ala Pro Ser Val Phe Ile Phe Pro Pro Ser Asp Glu Gln Leu
625                 630                 635                 640

Lys Ser Gly Thr Ala Ser Val Val Cys Leu Leu Asn Asn Phe Tyr Pro
                645                 650                 655

Arg Glu Ala Lys Val Gln Trp Lys Val Asp Asn Ala Leu Gln Ser Gly
            660                 665                 670

Asn Ser Gln Glu Ser Val Thr Glu Gln Asp Ser Lys Asp Ser Thr Tyr
        675                 680                 685

Ser Leu Ser Ser Thr Leu Thr Leu Ser Lys Ala Asp Tyr Glu Lys His
    690                 695                 700

Lys Val Tyr Ala Cys Glu Val Thr His Gln Gly Leu Ser Ser Pro Val
705                 710                 715                 720

Thr Lys Ser Phe Asn Arg Gly Glu Cys
                725

<210> SEQ ID NO 5
<211> LENGTH: 2187
<212> TYPE: DNA
<213> ORGANISM: Artificial Sequence
<220> FEATURE:
<223> OTHER INFORMATION: DMab TIM-3 nucleic acid sequence

<400> SEQUENCE: 5

-continued

```
atggattgga cttggaggat tctgtttctg gtcgccgccg ctacaggaac tcacgctcag    60
gtgcagctgg tgcagtctgg ggccgaagtg aagaaacccg gcgcttcagt caaagtgagc   120
tgcaaggcat ccggatacac tttcacctcc tattggatgc actgggtgcg gcaggcacct   180
ggacagggac tggagtggat gggggaaatt aacccatcta atggcagaac aaactacaac   240
gagaagttta aaactcgggt gacaatcact gcagacacct ccacatctac tgcctatatg   300
gagctgagct ccctgcgctc cgaagacact gccgtgtact attgcgccag ggctactat    360
ctgtacttcg attattgggg ccagctggga actctggtca ccgtgtctag tgcttcaaca   420
aaagggccta gcgtgtttcc cctggcacct tcaagcaaga gtacatcagg cggaactgcc   480
gctctgggct gtctggtgaa ggattacttc cctgagccag tcaccgtgtc ttggaacagt   540
ggcgcactga cttccggagt ccatacccttt cccgccgtgc tgcagtcctc tggactgtac   600
tctctgagtt cagtggtcac agtccctagc tcctctctgg ggacccagac atatatttgc   660
aacgtgaatc acaaaccaag taacactaag gtcgacaaga agtggaacc caaaagctgt    720
gataagactc atacctgccc tccctgtcca gcacctgagc tgctgggcgg cccaagcgtg   780
ttcctgtttc cacccaagcc taagacaccc tgatgatct cccggacccc agaagtcaca    840
tgcgtggtcg tggacgtgtc tcacgaggac cccgaagtca agttcaactg gtacgtggat   900
ggcgtcgagg tgcataatgc taagacaaaa ccacgagagg aacagtacaa ctccaccta   960
agggtcgtgt ctgtcctgac agtgctgcac caggactggc tgaacggaaa ggagtataag  1020
tgcaaagtga gcaacaaggc cctgccagca cccattgaga gacaatcag caaggcaaaa   1080
gggcagccaa gggaacccca ggtgtacact ctgcctccat ccagagacga gctgactaaa   1140
aaccaggtct ctctgacctg tctggtgaag gggttctatc cctctgatat cgccgtggag   1200
tgggaaagta atggccagcc tgaaaacaat tacaagacca caccccctgt gctggactca   1260
gatggcagct ctttctgta tagcaaactg accgtggaca gtcccgctg cagcaggga    1320
aacgtctta gctgctccgt gatgcatgag gccctgcaca atcattacac ccagaagtct   1380
ctgagtctgt cacctgggaa cgaggacga aagaggagaa gcgggtccgg agccacaaac   1440
ttctcccctgc tgaagcaggc tggagatgtg gaggaaaatc ctgggccaat ggtcctgcag  1500
actcaggtgt ttattagtct gctgctgtgg atctcaggag cttacgggga cattcagatg   1560
acccagagcc ctagttcact gtctgccagt gtcggagatc gggtgacaat cacttgtcac   1620
gctagccagg gcatcaggat caacatcggc tggtaccagc agaagcctgg caaagctcca   1680
aagctgctga tctaccatgg aaccaatctg gaagacgggg tgccaagcag gttctcagga   1740
agcgggtccg gcaccgactt taccctgaca atcagctccc tgcagcctga ggatttcgca   1800
acatactatt gcgtgcagta cggccagttc ccatggacat tggacagggg gactaaactg   1860
agaattaaga ccgtcgcagc cccaacagtg agcatctttc caccctctag tgaacagctg   1920
acctctggag gggccagtgt ggtgtgcttc ctgaacaact ctacccccaa ggacattaac   1980
gtcaagtgga aaatcgatgg ctcagagcga cagaacggag tgctgaatag ctggactgac   2040
caggattcca aagactctac ctatagtatg tcaagcactc tgacccctgac aaaggatgag   2100
tacgaacgcc acaatagcta tacctgcgag gcaacccaca agacttccac atccccccatc   2160
gtgaaatcct ttaatagagg caggtgt                                      2187
```

<210> SEQ ID NO 6
<211> LENGTH: 729
<212> TYPE: PRT

<213> ORGANISM: Artificial Sequence
<220> FEATURE:
<223> OTHER INFORMATION: Human TIM-3

<400> SEQUENCE: 6

```
Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Trp Met His Trp Val Arg Gln Ala Pro Gly Gln Gly Leu
    50                  55                  60

Glu Trp Met Gly Glu Ile Asn Pro Ser Asn Gly Arg Thr Asn Tyr Asn
65                  70                  75                  80

Glu Lys Phe Lys Thr Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Tyr Tyr Leu Tyr Phe Asp Tyr Trp Gly Gln
        115                 120                 125

Leu Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
```

Trp Glu Ser Asn Gly Gln Pro Glu Asn Tyr Lys Thr Thr Pro Pro
385             390                 395                 400
                    405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
450                 455                 460

Pro Gly Lys Arg Gly Arg Lys Arg Ser Gly Ser Gly Ala Thr Asn
465                 470                 475                 480

Phe Ser Leu Leu Lys Gln Ala Gly Asp Val Glu Glu Asn Pro Gly Pro
                485                 490                 495

Met Val Leu Gln Thr Gln Val Phe Ile Ser Leu Leu Leu Trp Ile Ser
                500                 505                 510

Gly Ala Tyr Gly Asp Ile Gln Met Thr Gln Ser Pro Ser Ser Leu Ser
                515                 520                 525

Ala Ser Val Gly Asp Arg Val Thr Ile Thr Cys His Ala Ser Gln Gly
530                 535                 540

Ile Arg Ile Asn Ile Gly Trp Tyr Gln Gln Lys Pro Gly Lys Ala Pro
545                 550                 555                 560

Lys Leu Leu Ile Tyr His Gly Thr Asn Leu Glu Asp Gly Val Pro Ser
                565                 570                 575

Arg Phe Ser Gly Ser Gly Ser Gly Thr Asp Phe Thr Leu Thr Ile Ser
                580                 585                 590

Ser Leu Gln Pro Glu Asp Phe Ala Thr Tyr Tyr Cys Val Gln Tyr Gly
                595                 600                 605

Gln Phe Pro Trp Thr Phe Gly Gln Gly Thr Lys Leu Arg Ile Lys Thr
                610                 615                 620

Val Ala Ala Pro Thr Val Ser Ile Phe Pro Pro Ser Ser Glu Gln Leu
625                 630                 635                 640

Thr Ser Gly Gly Ala Ser Val Val Cys Phe Leu Asn Asn Phe Tyr Pro
                645                 650                 655

Lys Asp Ile Asn Val Lys Trp Lys Ile Asp Gly Ser Glu Arg Gln Asn
                660                 665                 670

Gly Val Leu Asn Ser Trp Thr Asp Gln Asp Ser Lys Asp Ser Thr Tyr
                675                 680                 685

Ser Met Ser Ser Thr Leu Thr Leu Thr Lys Asp Glu Tyr Glu Arg His
                690                 695                 700

Asn Ser Tyr Thr Cys Glu Ala Thr His Lys Thr Ser Thr Ser Pro Ile
705                 710                 715                 720

Val Lys Ser Phe Asn Arg Gly Arg Cys
                725

<210> SEQ ID NO 7
<211> LENGTH: 2292
<212> TYPE: DNA
<213> ORGANISM: Artificial Sequence
<220> FEATURE:
<223> OTHER INFORMATION: DMab Human PD-1 nucleic acid sequence

<400> SEQUENCE: 7
atggactgga cttggcgcat tctgtttctg gtggccgccg ctactggaac tcacgctcag      60
gtgcagctgc aggaatcagg acccggagtg gtcaagccca gtggaaccct gtcactgaca     120

```
tgcgccatct ccggcggatc tattgggagt gggggctcaa tccgaagcac caggtggtgg      180
tcatgggtga gacagagccc aggcaaggga ctggagtgga tcggagaaat ctaccactca      240
ggaagcacta actataatcc ttccctgaag tctcgggtga ccattagcct ggataaatcc      300
agaaaccatt tctccctgcg gctgaattct gtcactgccg ctgacaccgc cgtgtactat      360
tgtgctcggc aggactacgg agattccggg gactggtatt tcgatctgtg ggggaagggc      420
actatggtca ccgtgagctc cgctagtacc aaaggcccct cagtgtttcc cctggcacct      480
tgctcccgct ctacaagtga atcaactgca gccctgggat gtctggtgaa ggactacttc      540
cccgaacctg tcacagtgag ttggaactca ggagcactga cttctggggt ccacacctt     600 cctgccgtgc tgcagtctag tgggctgtac agcctgtcaa gcgtggtcac tgtgccttcc     660
tctagtctgg gcacaaagac ttatacctgc aacgtggatc ataaaccaag caataccaag     720
gtcgacaaaa gggtggagtc caagtacggc cctccctgcc caccctgtcc agcacccgaa     780
ttcctgggag gcctagcgt gttcctgttt cctccaaagc caaagatac cctgatgatc       840 tccagaaccc cagaggtcac atgcgtggtc gtggacgtga gccaggagga ccccgaagtc     900
cagttcaact ggtacgtgga cggcgtcgaa gtgcacaatg ctaagacaaa acctcgggag     960
gaacagttta cagcactta ccgcgtcgtg tccgtcctga ccgtgctgca tcaggactgg     1020
ctgaacggca aggagtataa gtgcaaagtg agcaataagg gactgccatc aagcatcgag    1080
aaaacaattt ccaaggctaa aggccagcca agggaacccc aggtgtacac tctgcccct    1140 tctcaggagg aaatgaccaa gaaccaggtc agcctgacat gtctggtgaa aggcttttat    1200
ccctccgata tcgcagtgga gtgggaatct aatggacagc tgagaacaa ttacaagacc     1260 acaccacccg tgctggacag cgatggcagc ttcttcctgt attcacgcct gaccgtggac    1320
aaaagccgat ggcaggaggg gaacgtcttc agctgctccg tgatgcacga agccctgcac    1380
aatcattaca cacagaagtc tctgagtctg tcactgggca agcggggacg caaaaggaga    1440
agcggcagcg gggcaactaa cttttccctg ctgaaacagg ccggggatgt ggaggaaaat    1500
cctggcccaa tggtcctgca gacacaggtg ttcatctctc tgctgctgtg gattagtggg    1560
gcatacggca acttatgct gacccagcca cattctgtca gtgagtcacc cgggaagaca    1620
gtgactatct cctgtacacg atcctctggc tctattgcca gcaattccgt gcagtggtac    1680
cagcagaggc ctggcagttc accaactacc gtgatctatg aggacaacca gaggccctcc    1740
ggagtgcctg atagattctc tgggagtatt gacagctcct ctaattcagc cagcctgaca    1800
gtgagcggac tgaagactga ggatgaagcc gactactatt gccagagttc agatagctcc    1860
gctgtcgtgt tcggctccgg aacaaaactg actgtcctgg actttggcgt gtactattgt    1920
cagcagtacg agttctttgg gcagggcacc aaggtccagg tggatatcaa acgcacagtc    1980
gctgcaccaa gcgtgttcat ctttcctcca gcgacgagc agctgaagtc tgggaccgct    2040
agtgtcgtgt gcctgctgaa caacttctac ccccgagaag ctaaggtcca gtggaaagtg    2100
gataacgcac tgcagtctgg caatagtcag gagtccgtga cagaacagga tagcaaggac    2160
tccacttatt ctctgtctag taccctgaca ctgagcaaag ccgactacga gaagcacaaa    2220
gtgtatgctt gtgaggtgac ccatcaggga ctgcggagcc cagtgacaaa atccttcaat    2280
aggggagaat gt                                                         2292
```

<210> SEQ ID NO 8
<211> LENGTH: 764
<212> TYPE: PRT
<213> ORGANISM: Artificial Sequence -continued

```
<220> FEATURE:
<223> OTHER INFORMATION: Human PD-1

<400> SEQUENCE: 8

Met Asp Trp Thr Trp Arg Ile Leu Phe Leu Val Ala Ala Thr Gly
1               5                   10                  15

Thr His Ala Gln Val Gln Leu Gln Glu Ser Gly Pro Gly Val Val Lys
            20                  25                  30

Pro Ser Gly Thr Leu Ser Leu Thr Cys Ala Ile Ser Gly Gly Ser Ile
            35                  40                  45

Gly Ser Gly Gly Ser Ile Arg Ser Thr Arg Trp Trp Ser Trp Val Arg
        50                  55                  60

Gln Ser Pro Gly Lys Gly Leu Glu Trp Ile Gly Glu Ile Tyr His Ser
65                  70                  75                  80

Gly Ser Thr Asn Tyr Asn Pro Ser Leu Lys Ser Arg Val Thr Ile Ser
                85                  90                  95

Leu Asp Lys Ser Arg Asn His Phe Ser Leu Arg Leu Asn Ser Val Thr
            100                 105                 110

Ala Ala Asp Thr Ala Val Tyr Tyr Cys Ala Arg Gln Asp Tyr Gly Asp
        115                 120                 125

Ser Gly Asp Trp Tyr Phe Asp Leu Trp Gly Lys Gly Thr Met Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Lys Thr Tyr Thr Cys Asn Val Asp His Lys Pro Ser Asn Thr Lys
225                 230                 235                 240

Val Asp Lys Arg Val Glu Ser Lys Tyr Gly Pro Pro Cys Pro Pro Cys
                245                 250                 255

Pro Ala Pro Glu Phe Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser Gln Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Gly Leu Pro Ser Ser Ile Glu Lys Thr Ile Ser Lys Ala Lys Gly
        355                 360                 365

Gln Pro Arg Glu Pro Gln Val Tyr Thr Leu Pro Pro Ser Gln Glu Glu
    370                 375                 380

Met Thr Lys Asn Gln Val Ser Leu Thr Cys Leu Val Lys Gly Phe Tyr
385                 390                 395                 400
```

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Arg Leu Thr Val Asp Lys Ser Arg Trp Gln Glu Gly Asn
        435                 440                 445

Val Phe Ser Cys Ser Val Met His Glu Ala Leu His Asn His Tyr Thr
450                 455                 460

Gln Lys Ser Leu Ser Leu Ser Leu Gly Lys Arg Gly Arg Lys Arg Arg
465                 470                 475                 480

Ser Gly Ser Gly Ala Thr Asn Phe Ser Leu Leu Lys Gln Ala Gly Asp
                485                 490                 495

Val Glu Glu Asn Pro Gly Pro Met Val Leu Gln Thr Gln Val Phe Ile
            500                 505                 510

Ser Leu Leu Leu Trp Ile Ser Gly Ala Tyr Gly Asn Phe Met Leu Thr
        515                 520                 525

Gln Pro His Ser Val Ser Glu Ser Pro Gly Lys Thr Val Thr Ile Ser
530                 535                 540

Cys Thr Arg Ser Ser Gly Ser Ile Ala Ser Asn Ser Val Gln Trp Tyr
545                 550                 555                 560

Gln Gln Arg Pro Gly Ser Ser Pro Thr Thr Val Ile Tyr Glu Asp Asn
                565                 570                 575

Gln Arg Pro Ser Gly Val Pro Asp Arg Phe Ser Gly Ser Ile Asp Ser
            580                 585                 590

Ser Ser Asn Ser Ala Ser Leu Thr Val Ser Gly Leu Lys Thr Glu Asp
        595                 600                 605

Glu Ala Asp Tyr Tyr Cys Gln Ser Ser Asp Ser Ser Ala Val Val Phe
610                 615                 620

Gly Ser Gly Thr Lys Leu Thr Val Leu Asp Phe Gly Val Tyr Tyr Cys
625                 630                 635                 640

Gln Gln Tyr Glu Phe Phe Gly Gln Gly Thr Lys Val Gln Val Asp Ile
                645                 650                 655

Lys Arg Thr Val Ala Ala Pro Ser Val Phe Ile Phe Pro Pro Ser Asp
            660                 665                 670

Glu Gln Leu Lys Ser Gly Thr Ala Ser Val Val Cys Leu Leu Asn Asn
        675                 680                 685

Phe Tyr Pro Arg Glu Ala Lys Val Gln Trp Lys Val Asp Asn Ala Leu
690                 695                 700

Gln Ser Gly Asn Ser Gln Glu Ser Val Thr Glu Gln Asp Ser Lys Asp
705                 710                 715                 720

Ser Thr Tyr Ser Leu Ser Ser Thr Leu Thr Leu Ser Lys Ala Asp Tyr
                725                 730                 735

Glu Lys His Lys Val Tyr Ala Cys Glu Val Thr His Gln Gly Leu Arg
            740                 745                 750

Ser Pro Val Thr Lys Ser Phe Asn Arg Gly Glu Cys
        755                 760

<210> SEQ ID NO 9
<211> LENGTH: 2166
<212> TYPE: DNA
<213> ORGANISM: Artificial Sequence
<220> FEATURE:
<223> OTHER INFORMATION: Mouse LAG3-IgG1

<400> SEQUENCE: 9

```
atgggctgga gctgcatcat cctgttcctg gtggcaaccg caacaggagt gcactcccag    60
gtgaagctgc tgcagtctgg agccgccctg gtgaagcctg agcatccgt gaagatgtct   120
tgtaaggcca gcggctacac ctttacagat tattgggtgt cctgggtgaa gcagtcccac   180
ggcaagtctc tggagtggat cggcgagatc tacccaaagt ctggcaccag caacttcaat   240
gagaagttta agggcaaggc caccctgaca gtggataagt ccacctctac agcctatatg   300
gagctgagcc ggctgacatc cgaggactct gccatctact attgcaccgg cggcgcctac   360
tggggacagg gcaccctggt gacagtgagc tccgccaaga ccacacccc ttccgtgtat   420
ccactggcac aggctctgc cgcacagacc aatagcatgg tgacactggg ctgtctggtg   480
aagggctact cccccgagcc tgtgaccgtg acatggaaca gcggctccct gtctagcgga   540
gtgcacacct tccagccgt gctgcagagc gacctgtata cactgtcctc tagcgtgacc   600
gtgccttcct ctccacggcc ctccgagacc gtgacatgca atgtggccca cccagccagc   660
tccacaaagg tggacaagaa gatcgtgccc cgcgattgcg gctgtaagcc atgcatctgt   720
accgtgcccg aggtgtctag cgtgttcatc tttccaccca gcccaaggaa tgtgctgacc   780
atcacactga cccctaaggt gacctgcgtg gtggtggaca tcagcaagga cgatcctgag   840
gtgcagttct cctggtttgt ggacgatgtg gaggtgcaca ccgcccagac acagcctagg   900
gaggagcagt tcaacagcac ctttagatct gtgagcgagc tgccaatcat gcaccaggat   960
tggctgaatg gcaaggagtt caagtgcagg gtgaacagcg ccgcatttcc tgcaccaatc  1020
gagaagacca tctccaagac aaagggccgc cctaaggccc cacaggtgta cacaatccct  1080
ccacccaagg agcagatggc caaggacaag gtgagcctga cctgtatgat cacagacttc  1140
tttcctgagg atatcaccgt ggagtggcag tggaatggcc agcctgccga gaactacaag  1200
aatacacagc caatcatgaa caccaatggc agctacttcg tgtattccaa gctgaacgtg  1260
cagaagtcca attgggaggc cggcaacacc ttcacctgct ctgtgctgca cgagggcctg  1320
cacaaccacc acacagagaa gtccctgtct cacagcccag gcaagagggg aaggaagagg  1380
agatccggct ctggcgccac caatttctct ctgctgaagc aggcaggcga tgtggaggag  1440
aacccaggac ctatgaggtg ctccctgcag ttcctgggcg tgctgatgtt ttggatcagc  1500
ggcgtgtccg gcgacgtggt gctgacacag accccctcta tcctgagcac cacaatcggc  1560
cagagcgtgt ccatctcttg tagatcctct cagagcctgc tggactccga tggcaacacc  1620
tacctgtatt ggttcctgca gaggccagga cagagccctc agcgcctgat ctacctggtg  1680
tctaatctga ggagcggcgt gcctaacaga ttcagcggct ccggctctgg caccgacttt  1740
acactgaaga tctccggagt ggaggcagag atctggcg tgtactattg catgcaggcc  1800
acccacgacc cactgacatt cggctctggc accaagctgg agatcaaggc agacgcagca  1860
ccaacagtga gcatctttcc tccaagctcc gagcagctga cctccggcgg cgcctctgtg  1920
gtgtgcttcc tgaacaactt ctaccccaaag gacatcaacg tgaagtggaa gatcgatggc  1980
tctgagcgcc agaacggcgt gctgaatagc tggacagacc aggattccaa ggattctacc  2040
tatagcatgt ctagcacact gacccctgaca aaggacgagt acgagaggca caattcctat  2100
acctgcgagg ccacacacaa gaccagcaca tcccccatcg tgaagtcttt caacagaggc  2160
gagtgt                                                             2166
```

<210> SEQ ID NO 10
<211> LENGTH: 722
<212> TYPE: PRT

<213> ORGANISM: Artificial Sequence
<220> FEATURE:
<223> OTHER INFORMATION: Mouse Lag3-IgG1

<400> SEQUENCE: 10

```
Met Gly Trp Ser Cys Ile Ile Leu Phe Leu Val Ala Thr Ala Thr Gly
1               5                   10                  15

Val His Ser Gln Val Lys Leu Leu Gln Ser Gly Ala Ala Leu Val Lys
                20                  25                  30

Pro Gly Ala Ser Val Lys Met Ser Cys Lys Ala Ser Gly Tyr Thr Phe
            35                  40                  45

Thr Asp Tyr Trp Val Ser Trp Val Lys Gln Ser His Gly Lys Ser Leu
        50                  55                  60

Glu Trp Ile Gly Glu Ile Tyr Pro Lys Ser Gly Thr Ser Asn Phe Asn
65                  70                  75                  80

Glu Lys Phe Lys Gly Lys Ala Thr Leu Thr Val Asp Lys Ser Thr Ser
                85                  90                  95

Thr Ala Tyr Met Glu Leu Ser Arg Leu Thr Ser Glu Asp Ser Ala Ile
            100                 105                 110

Tyr Tyr Cys Thr Gly Gly Ala Tyr Trp Gly Gln Gly Thr Leu Val Thr
        115                 120                 125

Val Ser Ser Ala Lys Thr Thr Pro Pro Ser Val Tyr Pro Leu Ala Pro
130                 135                 140

Gly Ser Ala Ala Gln Thr Asn Ser Met Val Thr Leu Gly Cys Leu Val
145                 150                 155                 160

Lys Gly Tyr Phe Pro Glu Pro Val Thr Val Thr Trp Asn Ser Gly Ser
                165                 170                 175

Leu Ser Ser Gly Val His Thr Phe Pro Ala Val Leu Gln Ser Asp Leu
            180                 185                 190

Tyr Thr Leu Ser Ser Ser Val Thr Val Pro Ser Ser Pro Arg Pro Ser
        195                 200                 205

Glu Thr Val Thr Cys Asn Val Ala His Pro Ala Ser Ser Thr Lys Val
210                 215                 220

Asp Lys Lys Ile Val Pro Arg Asp Cys Gly Cys Lys Pro Cys Ile Cys
225                 230                 235                 240

Thr Val Pro Glu Val Ser Ser Val Phe Ile Phe Pro Pro Lys Pro Lys
                245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Gln Pro Arg Glu Glu Gln Phe
290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Lys Glu Gln Met Ala Lys
        355                 360                 365

Asp Lys Val Ser Leu Thr Cys Met Ile Thr Asp Phe Phe Pro Glu Asp
370                 375                 380

Ile Thr Val Glu Trp Gln Trp Asn Gly Gln Pro Ala Glu Asn Tyr Lys
```

```
385                 390                 395                 400
Asn Thr Gln Pro Ile Met Asn Thr Asn Gly Ser Tyr Phe Val Tyr Ser
                405                 410                 415
Lys Leu Asn Val Gln Lys Ser Asn Trp Glu Ala Gly Asn Thr Phe Thr
                420                 425                 430
Cys Ser Val Leu His Glu Gly Leu His Asn His His Thr Glu Lys Ser
                435                 440                 445
Leu Ser His Ser Pro Gly Lys Arg Gly Arg Lys Arg Arg Ser Gly Ser
450                 455                 460
Gly Ala Thr Asn Phe Ser Leu Leu Lys Gln Ala Gly Asp Val Glu Glu
465                 470                 475                 480
Asn Pro Gly Pro Met Arg Cys Ser Leu Gln Phe Leu Gly Val Leu Met
                485                 490                 495
Phe Trp Ile Ser Gly Val Ser Gly Asp Val Val Leu Thr Gln Thr Pro
                500                 505                 510
Ser Ile Leu Ser Thr Thr Ile Gly Gln Ser Val Ser Ile Ser Cys Arg
                515                 520                 525
Ser Ser Gln Ser Leu Leu Asp Ser Asp Gly Asn Thr Tyr Leu Tyr Trp
                530                 535                 540
Phe Leu Gln Arg Pro Gly Gln Ser Pro Gln Arg Leu Ile Tyr Leu Val
545                 550                 555                 560
Ser Asn Leu Arg Ser Gly Val Pro Asn Arg Phe Ser Gly Ser Gly Ser
                565                 570                 575
Gly Thr Asp Phe Thr Leu Lys Ile Ser Gly Val Glu Ala Glu Asp Leu
                580                 585                 590
Gly Val Tyr Tyr Cys Met Gln Ala Thr His Asp Pro Leu Thr Phe Gly
                595                 600                 605
Ser Gly Thr Lys Leu Glu Ile Lys Ala Asp Ala Ala Pro Thr Val Ser
                610                 615                 620
Ile Phe Pro Pro Ser Ser Glu Gln Leu Thr Ser Gly Gly Ala Ser Val
625                 630                 635                 640
Val Cys Phe Leu Asn Asn Phe Tyr Pro Lys Asp Ile Asn Val Lys Trp
                645                 650                 655
Lys Ile Asp Gly Ser Glu Arg Gln Asn Gly Val Leu Asn Ser Trp Thr
                660                 665                 670
Asp Gln Asp Ser Lys Asp Ser Thr Tyr Ser Met Ser Ser Thr Leu Thr
                675                 680                 685
Leu Thr Lys Asp Glu Tyr Glu Arg His Asn Ser Tyr Thr Cys Glu Ala
                690                 695                 700
Thr His Lys Thr Ser Thr Ser Pro Ile Val Lys Ser Phe Asn Arg Gly
705                 710                 715                 720
Glu Cys
```

<210> SEQ ID NO 11
<211> LENGTH: 2193
<212> TYPE: DNA
<213> ORGANISM: Artificial Sequence
<220> FEATURE:
<223> OTHER INFORMATION: Human 4-1BB-IgG1

<400> SEQUENCE: 11

```
atggattgga cttggaggat tctgtttctg gtcgccgccg caaccgggac tcacgctcag     60
gtgcagctgc agcagtgggg cgcaggactg ctgaagcctt cagagactct gagcctgacc    120
tgcgccgtgt acggcggatc tttcagtggc tactattgga gctggatcag acagtccccc    180
```

```
gagaagggac tggaatggat cggggagatt aaccacggcg gatacgtgac ctataatcct    240
tctctggaga gtcgggtcac aatttccgtg gacacttcta agaaccagtt ttccctgaaa    300
ctgagctccg tcacagccgc tgacactgca gtgtactatt gtgcccggga ttacggccct    360
ggaaattacg actggtattt cgatctgtgg ggacgaggcc ccctggtcac agtgtctagt    420
gcttctacta aggggccaag cgtgttccca ctggcaccct gctcacggag cacctccgaa    480
tctacagcag ccctgggctg tctggtgaaa gattatttcc cagagcccgt cacagtgtca    540
tggaacagcg gcgcactgac ctccggagtc cacacatttc cgccgtgct gcagtcaagc     600 gggctgtact ctctgtcctc tgtggtcacc gtccctagtt caagcctggg cactaagacc    660
tatacatgca acgtggacca taaaccatcc aatacaaagg tcgataaacg cgtggaatct    720
aagtacggcc ctccctgccc accctgtcct gcaccagagt tcctgggagg cctagcgtg    780 ttcctgtttc ctccaaagcc aaaagacacc ctgatgatct cccgaactcc agaagtcacc    840
tgcgtggtcg tggacgtgtc tcaggaggac cccgaagtcc agttcaactg gtacgtggat    900
ggagtcgagg tgcacaatgc taagacaaaa ccaagggagg aacagtttaa ctcaacttac    960
agagtcgtga gcgtcctgac cgtgctgcat caggactggc tgaacggaaa ggagtataag   1020
tgcaaagtga gcaataaggg gctgccctcc tctatcgaaa aaactattag caaggctaaa   1080
ggccagcctc gcgagccaca ggtgtacacc ctgcccccta gccaggagga aatgaccaag   1140
aaccaggtca gcctgacatg tctggtgaaa ggcttctatc cctctgacat cgcagtggag   1200
tgggaaagta tggacagcc tgagaacaat tacaagacca caccaccgt gctggactcc    1260 gatggctctt tctttctgta tagtagactg accgtggata aatcacggtg gcaggaagga   1320
aacgtcttta gttgctcagt gatgcacgag gccctgcaca atcattacac tcagaagagc   1380
ctgtccctgt ctctgggcaa gcggggacgc aaaaggagaa gtggatcagg ggccaccaac   1440
ttcagcctgc tgaaacaggc tggggacgtg gaggaaaatc ccggcccta tggtcctgcag   1500 acacaggtgt ttatctccct gctgctgtgg atttctgggg cctacggcga aatcgtgctg   1560
actcagtccc cagctaccct gagcctgtcc ccaggagagc gagctaccct gtcttgtagg   1620
gcatctcaga gtgtgagttc atacctggca tggtatcagc agaagcccgg acaggccct    1680 aggctgctga tctatgatgc cagcaaccgc gctaccggga ttccagcacg attctcaggc   1740
agcggcagcg gaacagactt tactctgacc attagcctgg agcccgaaga tttcgcagtg   1800
tactattgcc agcagcgaag caattggcct ccagccctga catttggcgg agggactaag   1860
gtggaaatca aaaggacagt cgctgcaccc agcgtgttca ttttccccc ttccgacgag   1920 cagctgaaga gtggaactgc ttcagtggtg tgcctgctga acaatttcta ccctagagaa   1980
gctaaggtcc agtggaaagt ggataacgca ctgcagagtg ggaattcaca ggaaagcgtg   2040
acagagcagg actccaagga ttctacttat agtctgagct ccacactgac tctgagcaaa   2100
gccgactacg agaagcataa agtgtatgct tgcgaggtca ctcaccaggg gctgtcaagt   2160
ccagtcacta aatctttcaa tagaggcgaa tgt                                2193
```

<210> SEQ ID NO 12
<211> LENGTH: 731
<212> TYPE: PRT
<213> ORGANISM: Artificial Sequence
<220> FEATURE:
<223> OTHER INFORMATION: Human 4-1BB-IgG1 amino acid
<400> SEQUENCE: 12

-continued

```
Met Asp Trp Thr Trp Arg Ile Leu Phe Leu Val Ala Ala Thr Gly
1               5                   10                  15

Thr His Ala Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
            35                  40                  45

Ser Gly Tyr Tyr Trp Ser Trp Ile Arg Gln Ser Pro Glu Lys Gly Leu
    50                  55                  60

Glu Trp Ile Gly Glu Ile Asn His Gly Gly Tyr Val Thr Tyr Asn Pro
65                  70                  75                  80

Ser Leu Glu Ser Arg Val Thr Ile Ser Val Asp Thr Ser Lys Asn Gln
            85                  90                  95

Phe Ser Leu Lys Leu Ser Ser Val Thr Ala Ala Asp Thr Ala Val Tyr
            100                 105                 110

Tyr Cys Ala Arg Asp Tyr Gly Pro Gly Asn Tyr Asp Trp Tyr Phe Asp
            115                 120                 125

Leu Trp Gly Arg Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
            275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Arg Leu Thr Val
```

```
                420                 425                 430
Asp Lys Ser Arg Trp Gln Glu Gly Asn Val Phe Ser Cys Ser Val Met
            435                 440                 445

His Glu Ala Leu His Asn His Tyr Thr Gln Lys Ser Leu Ser Leu Ser
450                 455                 460

Leu Gly Lys Arg Gly Arg Lys Arg Arg Ser Gly Ser Gly Ala Thr Asn
465                 470                 475                 480

Phe Ser Leu Leu Lys Gln Ala Gly Asp Val Glu Glu Asn Pro Gly Pro
            485                 490                 495

Met Val Leu Gln Thr Gln Val Phe Ile Ser Leu Leu Leu Trp Ile Ser
            500                 505                 510

Gly Ala Tyr Gly Glu Ile Val Leu Thr Gln Ser Pro Ala Thr Leu Ser
            515                 520                 525

Leu Ser Pro Gly Glu Arg Ala Thr Leu Ser Cys Arg Ala Ser Gln Ser
            530                 535                 540

Val Ser Ser Tyr Leu Ala Trp Tyr Gln Gln Lys Pro Gly Gln Ala Pro
545                 550                 555                 560

Arg Leu Leu Ile Tyr Asp Ala Ser Asn Arg Ala Thr Gly Ile Pro Ala
                565                 570                 575

Arg Phe Ser Gly Ser Gly Ser Gly Thr Asp Phe Thr Leu Thr Ile Ser
            580                 585                 590

Leu Glu Pro Glu Asp Phe Ala Val Tyr Tyr Cys Gln Gln Arg Ser Asn
            595                 600                 605

Trp Pro Pro Ala Leu Thr Phe Gly Gly Gly Thr Lys Val Glu Ile Lys
            610                 615                 620

Arg Thr Val Ala Ala Pro Ser Val Phe Ile Phe Pro Pro Ser Asp Glu
625                 630                 635                 640

Gln Leu Lys Ser Gly Thr Ala Ser Val Val Cys Leu Leu Asn Asn Phe
                645                 650                 655

Tyr Pro Arg Glu Ala Lys Val Gln Trp Lys Val Asp Asn Ala Leu Gln
                660                 665                 670

Ser Gly Asn Ser Gln Glu Ser Val Thr Glu Gln Asp Ser Lys Asp Ser
            675                 680                 685

Thr Tyr Ser Leu Ser Ser Thr Leu Thr Leu Ser Lys Ala Asp Tyr Glu
690                 695                 700

Lys His Lys Val Tyr Ala Cys Glu Val Thr His Gln Gly Leu Ser Ser
705                 710                 715                 720

Pro Val Thr Lys Ser Phe Asn Arg Gly Glu Cys
                725                 730

<210> SEQ ID NO 13
<211> LENGTH: 2190
<212> TYPE: DNA
<213> ORGANISM: Artificial Sequence
<220> FEATURE:
<223> OTHER INFORMATION: Human OX40-IgG1-Agonist (Humanized from mouse
      anti-human OX-40)

<400> SEQUENCE: 13
atggattgga cttggaggat tctgtttctg gtcgccgccg caactggaac ccacgctcag      60
gtgcagctgg tgcagtcagg ctccgagctg aagaagccag gcgcctccgt gaaggtgtct     120
tgcaaggcca gcggctacac cttcacagac tatagcatgc actgggtgag gcaggcacca     180
ggacagggcc tgaagtggat gggctggatc aacaccgaga caggcgagcc cacatacgcc     240
gacgacttca aggcagatt cgtgtttagc ctggacacat ccgtgtctac cgcctatctg      300
```

```
cagatcagct ccctgaaggc cgaggatacc gccgtgtact attgtgccaa tccatactat    360
gactacgtgt cctactatgc catggattat tggggccagg gcaccacagt gacagtgtct    420
agcgcctcta ccaagggacc aagcgtgttc ccactggcac cttgcagcag gtccacatct    480
gagagcaccg ccgccctggg atgtctggtg aaggattact cccccgagcc tgtgaccgtg    540
agctggaact ccggcgccct gacatccgga gtgcacacct tcctgccgt gctgcagtcc     600
tctggcctgt actctctgag ctccgtggtg acagtgcctt ctagctccct gggcaccaag    660
acatatacct gcaacgtgga ccacaagcca tctaatacca aggtggataa gagggtggag    720
agcaagtacg gccctcctg cccacccgt ccagcaccag agtttctggg cggcccatcc      780
gtgttcctgt tcctccaaa gcctaaggac acactgatga tcagcagaac acctgaggtg    840
acctgcgtgt ggtggacgt gtcccaggag accccgagg tgcagttcaa ctggtacgtg     900
gatggcgtgg aggtgcacaa tgccaagacc aagcctcggg aggagcagtt taactccaca    960
taccgcgtgg tgtctgtgct gaccgtgctg caccaggact ggctgaacgg caaggagtat    1020
aagtgcaagg tgtctaataa gggcctgcca tctagcatcg agaagacaat cagcaaggca    1080
aagggacagc cacgggagcc acaggtgtac accctgcccc cttcccagga ggagatgaca    1140
aagaaccagg tgtctctgac ctgtctggtg aagggcttct atccaagcga catcgccgtg    1200
gagtgggagt ccaatggcca gcccgagaac aattacaaga ccacaccacc cgtgctggac    1260
tctgatggca gcttctttct gtattctagg ctgaccgtgg ataagagcag atggcaggag    1320
ggcaacgtgt tttcctgctc tgtgatgcac gaggccctgc acaatcacta cacacagaag    1380
agcctgtccc tgtctctggg caagagggga aggaagagga gagcggctc cggagcaacc    1440
aacttcagcc tgctgaagca ggcaggcgac gtggaggaga tcctggacc aatggtgctg    1500
cagacacagg tgtttatcag cctgctgctg tggatctccg gcgcctacgg cgatatccag    1560
atgacccagt cccctcctc tctgtctgcc agcgtgggcg acagggtgac aatcacctgt    1620
aaggcatccc aggacgtgag caccgcagtg gcctggtacc agcagaagcc tggcaaggcc    1680
ccaaagctgc tgatctattc cgcctcttac ctgtatacag gagtgcctag ccggttcagc    1740
ggctccggct ctggaaccga cttcaccttc accatcagct ccctgcagcc cgaggatatc    1800
gccacctact attgccagca gcactactcc acacctcgca cctttggcca gggcacaaag    1860
ctggagatca gaccgtggc cgcccctcc gtgttcatct ttcctccatc tgacgagcag     1920
ctgaagagcg gaaccgcatc cgtggtgtgc ctgctgaaca atttctaccc tcgcgaggcc    1980
aaggtgcagt ggaaggtgga taacgccctg cagtccggca attctcagga gagcgtgaca    2040
gagcaggact ccaaggattc tacctatagc ctgtctagca cactgaccct gagcaaggcc    2100
gactacgaga agcacaaggt gtatgcctgc gaggtcaccc accagggct gcggtcaccc     2160
gtcaccaagt ccttcaatag agggaatgc                                      2190
```

<210> SEQ ID NO 14
<211> LENGTH: 730
<212> TYPE: PRT
<213> ORGANISM: Artificial Sequence
<220> FEATURE:
<223> OTHER INFORMATION: Human OX-40-IgG1

<400> SEQUENCE: 14

Met Asp Trp Thr Trp Arg Ile Leu Phe Leu Val Ala Ala Ala Thr Gly
1               5                   10                  15

Thr His Ala Gln Val Gln Leu Val Gln Ser Gly Ser Glu Leu Lys Lys

```
                    20                  25                  30
Pro Gly Ala Ser Val Lys Val Ser Cys Lys Ala Ser Gly Tyr Thr Phe
                35                  40                  45
Thr Asp Tyr Ser Met His Trp Val Arg Gln Ala Pro Gly Gln Gly Leu
 50                  55                  60
Lys Trp Met Gly Trp Ile Asn Thr Glu Thr Gly Glu Pro Thr Tyr Ala
 65                  70                  75                  80
Asp Asp Phe Lys Gly Arg Phe Val Phe Ser Leu Asp Thr Ser Val Ser
                 85                  90                  95
Thr Ala Tyr Leu Gln Ile Ser Ser Leu Lys Ala Glu Asp Thr Ala Val
                100                 105                 110
Tyr Tyr Cys Ala Asn Pro Tyr Tyr Asp Tyr Val Ser Tyr Tyr Ala Met
                115                 120                 125
Asp Tyr Trp Gly Gln Gly Thr Thr Val Thr Val Ser Ser Ala Ser Thr
                130                 135                 140
Lys Gly Pro Ser Val Phe Pro Leu Ala Pro Cys Ser Arg Ser Thr Ser
145                 150                 155                 160
Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
                195                 200                 205
Val Val Thr Val Pro Ser Ser Ser Leu Gly Thr Lys Thr Tyr Thr Cys
                210                 215                 220
Asn Val Asp His Lys Pro Ser Asn Thr Lys Val Asp Lys Arg Val Glu
225                 230                 235                 240
Ser Lys Tyr Gly Pro Pro Cys Pro Pro Cys Pro Ala Pro Glu Phe Leu
                245                 250                 255
Gly Gly Pro Ser Val Phe Leu Phe Pro Pro Lys Pro Lys Asp Thr Leu
                260                 265                 270
Met Ile Ser Arg Thr Pro Glu Val Thr Cys Val Val Val Asp Val Ser
                275                 280                 285
Gln Glu Asp Pro Glu Val Gln Phe Asn Trp Tyr Val Asp Gly Val Glu
                290                 295                 300
Val His Asn Ala Lys Thr Lys Pro Arg Glu Glu Gln Phe Asn Ser Thr
305                 310                 315                 320
Tyr Arg Val Val Ser Val Leu Thr Val Leu His Gln Asp Trp Leu Asn
                325                 330                 335
Gly Lys Glu Tyr Lys Cys Lys Val Ser Asn Lys Gly Leu Pro Ser Ser
                340                 345                 350
Ile Glu Lys Thr Ile Ser Lys Ala Lys Gly Gln Pro Arg Glu Pro Gln
                355                 360                 365
Val Tyr Thr Leu Pro Pro Ser Gln Glu Glu Met Thr Lys Asn Gln Val
                370                 375                 380
Ser Leu Thr Cys Leu Val Lys Gly Phe Tyr Pro Ser Asp Ile Ala Val
385                 390                 395                 400
Glu Trp Glu Ser Asn Gly Gln Pro Glu Asn Asn Tyr Lys Thr Thr Pro
                405                 410                 415
Pro Val Leu Asp Ser Asp Gly Ser Phe Phe Leu Tyr Ser Arg Leu Thr
                420                 425                 430
Val Asp Lys Ser Arg Trp Gln Glu Gly Asn Val Phe Ser Cys Ser Val
                435                 440                 445
```

Met His Glu Ala Leu His Asn His Tyr Thr Gln Lys Ser Leu Ser Leu
    450                 455                 460
Ser Leu Gly Lys Arg Gly Arg Lys Arg Arg Ser Gly Ser Gly Ala Thr
465                 470                 475                 480
Asn Phe Ser Leu Leu Lys Gln Ala Gly Asp Val Glu Glu Asn Pro Gly
                485                 490                 495
Pro Met Val Leu Gln Thr Gln Val Phe Ile Ser Leu Leu Leu Trp Ile
            500                 505                 510
Ser Gly Ala Tyr Gly Asp Ile Gln Met Thr Gln Ser Pro Ser Ser Leu
        515                 520                 525
Ser Ala Ser Val Gly Asp Arg Val Thr Ile Thr Cys Lys Ala Ser Gln
    530                 535                 540
Asp Val Ser Thr Ala Val Ala Trp Tyr Gln Gln Lys Pro Gly Lys Ala
545                 550                 555                 560
Pro Lys Leu Leu Ile Tyr Ser Ala Ser Tyr Leu Tyr Thr Gly Val Pro
                565                 570                 575
Ser Arg Phe Ser Gly Ser Gly Ser Gly Thr Asp Phe Thr Phe Thr Ile
            580                 585                 590
Ser Ser Leu Gln Pro Glu Asp Ile Ala Thr Tyr Tyr Cys Gln Gln His
        595                 600                 605
Tyr Ser Thr Pro Arg Thr Phe Gly Gln Gly Thr Lys Leu Glu Ile Lys
    610                 615                 620
Thr Val Ala Ala Pro Ser Val Phe Ile Phe Pro Pro Ser Asp Glu Gln
625                 630                 635                 640
Leu Lys Ser Gly Thr Ala Ser Val Val Cys Leu Leu Asn Asn Phe Tyr
                645                 650                 655
Pro Arg Glu Ala Lys Val Gln Trp Lys Val Asp Asn Ala Leu Gln Ser
            660                 665                 670
Gly Asn Ser Gln Glu Ser Val Thr Glu Gln Asp Ser Lys Asp Ser Thr
        675                 680                 685
Tyr Ser Leu Ser Ser Thr Leu Thr Leu Ser Lys Ala Asp Tyr Glu Lys
    690                 695                 700
His Lys Val Tyr Ala Cys Glu Val Thr His Gln Gly Leu Arg Ser Pro
705                 710                 715                 720
Val Thr Lys Ser Phe Asn Arg Gly Glu Cys
                725                 730

<210> SEQ ID NO 15
<211> LENGTH: 2196
<212> TYPE: DNA
<213> ORGANISM: Artificial Sequence
<220> FEATURE:
<223> OTHER INFORMATION: Human GITR (Clone 36E5)

<400> SEQUENCE: 15
atggactgga catgaggat tctgtttctg gtcgccgctg ctactggaac ccacgccgag      60
gtcaatctgg tcgagtcagg gggaggactg gtcaagcccg gcggatctct gaaagtgagt    120
tgcgccgctt caggcttcac tttagctcc tacgccatgt cttgggtcag acagacccct    180
gagaagcggc tggaatgggt ggctagcatc tctagtgggg gcaccacata ctatccagac    240
tcagtgaaag gaaggttcac tatcagccga gataacgcca ggaatattct gtacctgcag    300
atgtcaagcc tgcgaagcga ggacaccgct atgtactatt gtgcaagggt gggagggtac    360
tatgactcta tggattattg ggggcagggc attagtgtca ctgattcctc tgcttcaacc    420

| | |
|---|---|
| aaggggccca gcgtgtttcc actggcaccc tgctcaagaa gcacttccga gtctaccgca | 480 |
| gccctgggct gtctggtgaa agactacttc cagaacccg tcaccgtgag ctggaactcc | 540 |
| ggcgcactga cctccggagt ccacacattt cctgccgtgc tgcagagttc aggactgtac | 600 |
| tctctgagct ccgtggtcac agtgccctct agttcactgg ggacaaagac ttatacctgc | 660 |
| aacgtggacc ataaacctag caatactaag gtcgataaac gcgtggagtc caagtacggc | 720 |
| cctccctgcc caccctgtcc tgcaccagaa ttcctgggcg gaccctccgt gttcctgttt | 780 |
| cctccaaagc ctaaagacac cctgatgatc tcccgaacac ctgaggtcac ttgcgtggtc | 840 |
| gtggacgtgt ctcaggagga ccccgaagtc cagttcaact ggtacgtgga tggcgtcgaa | 900 |
| gtgcacaatg ctaagacaaa acctcgggag gaacagttta actccaccta ccgcgtcgtg | 960 |
| tctgtcctga cagtgctgca tcaggattgg ctgaacggaa aggagtataa gtgcaaagtg | 1020 |
| agcaataagg ggctgccaag ctccatcgag aaaacaattt ccaaggccaa aggccagcct | 1080 |
| cgggaaccac aggtgtacac tctgccccct tctcaggagg aaatgacaaa gaaccaggtc | 1140 |
| agcctgactt gtctggtgaa agggttctat ccatccgaca tcgctgtgga gtgggaatct | 1200 |
| aatggccagc ccgagaacaa ttacaagact accccacccg tgctggactc tgatggcagt | 1260 |
| ttctttctgt atagcaggct gaccgtggat aaatccagat ggcaggaggg aaacgtcttt | 1320 |
| agttgctcag tgatgcacga agccctgcac aatcattaca cccagaagag cctgtccctg | 1380 |
| tctctgggga gcgaggacg caaaaggaga agtggatcag gggcaacaaa cttcagcctg | 1440 |
| ctgaagcagg caggggacgt ggaggaaaat ccaggaccta tggtcctgca gactcaggtg | 1500 |
| tttatcagtc tgctgctgtg gatttcagga gcctatgggg atatcgtcct gacccagtca | 1560 |
| ccagcaagcc tggccgtgag tctgggacag cgagcaacaa tttcatgtcg agctagcgag | 1620 |
| tccgtcgaca actacggcgt gagcttcatg aattggtttc agcagaagcc cggacagcct | 1680 |
| ccaaaactgc tgatctatgc tgcaagcaac cagggctccg gagtgccagc tcgcttctct | 1740 |
| gggagtggct caggaaccga ttttttccctg aatattcacc ccatggagga agacgatact | 1800 |
| gcaatgtact tctgccagca gaccaaggag gtgacatgga cttttggggg cggaacaaag | 1860 |
| ctggaaatca aaagagcaac tgtcgccgct cccagcgtgt tcatctttcc ccctagtgac | 1920 |
| gagcagctga gtctggaaca agccagtgtg gtgtgcctgc tgaacaattt ctaccctcgg | 1980 |
| gaagctaagg tccagtggaa agtggataac gcactgcagt ccgggaattc tcaggagagt | 2040 |
| gtgaccgaac aggactcaaa ggatagcaca tattccctgt ctagtaccct gacactgtcc | 2100 |
| aaagccgact acgagaagca taaagtgtat gcttgcgaag tcacccacca ggggctgtca | 2160 |
| agtccagtca ccaaatcctt taatcgggga gaatgt | 2196 |

<210> SEQ ID NO 16
<211> LENGTH: 732
<212> TYPE: PRT
<213> ORGANISM: Artificial Sequence
<220> FEATURE:
<223> OTHER INFORMATION: Human GITR

<400> SEQUENCE: 16

Met Asp Trp Thr Trp Arg Ile Leu Phe Leu Val Ala Ala Ala Thr Gly
1               5                   10                  15

Thr His Ala Glu Val Asn Leu Val Glu Ser Gly Gly Gly Leu Val Lys
            20                  25                  30

Pro Gly Gly Ser Leu Lys Val Ser Cys Ala Ala Ser Gly Phe Thr Phe
        35                  40                  45

```
Ser Ser Tyr Ala Met Ser Trp Val Arg Gln Thr Pro Glu Lys Arg Leu
    50                  55                  60

Glu Trp Val Ala Ser Ile Ser Ser Gly Gly Thr Thr Tyr Tyr Pro Asp
65                  70                  75                  80

Ser Val Lys Gly Arg Phe Thr Ile Ser Arg Asp Asn Ala Arg Asn Ile
                85                  90                  95

Leu Tyr Leu Gln Met Ser Ser Leu Arg Ser Glu Asp Thr Ala Met Tyr
                100                 105                 110

Tyr Cys Ala Arg Val Gly Gly Tyr Tyr Asp Ser Met Asp Tyr Trp Gly
            115                 120                 125

Gln Gly Ile Ser Val Thr Asp Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Lys Thr Tyr Thr Cys Asn Val Asp His
                210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Phe Leu Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Asp Val Ser Gln Glu Asp Pro
                275                 280                 285

Glu Val Gln Phe Asn Trp Tyr Val Asp Gly Val Glu Val His Asn Ala
                290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
                340                 345                 350

Ile Ser Lys Ala Lys Gly Gln Pro Arg Glu Pro Gln Val Tyr Thr Leu
            355                 360                 365

Pro Pro Ser Gln Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
                420                 425                 430

Arg Trp Gln Glu Gly Asn Val Phe Ser Cys Ser Val Met His Glu Ala
            435                 440                 445

Leu His Asn His Tyr Thr Gln Lys Ser Leu Ser Leu Ser Leu Gly Lys
            450                 455                 460

Arg Gly Arg Lys Arg Arg Ser Gly Ser Gly Ala Thr Asn Phe Ser Leu
```

```
                465                 470                 475                 480
Leu Lys Gln Ala Gly Asp Val Glu Glu Asn Pro Gly Pro Met Val Leu
                    485                 490                 495

Gln Thr Gln Val Phe Ile Ser Leu Leu Leu Trp Ile Ser Gly Ala Tyr
                500                 505                 510

Gly Asp Ile Val Leu Thr Gln Ser Pro Ala Ser Leu Ala Val Ser Leu
            515                 520                 525

Gly Gln Arg Ala Thr Ile Ser Cys Arg Ala Ser Glu Ser Val Asp Asn
        530                 535                 540

Tyr Gly Val Ser Phe Met Asn Trp Phe Gln Gln Lys Pro Gly Gln Pro
545                 550                 555                 560

Pro Lys Leu Leu Ile Tyr Ala Ala Ser Asn Gln Gly Ser Gly Val Pro
                565                 570                 575

Ala Arg Phe Ser Gly Ser Gly Ser Gly Thr Asp Phe Ser Leu Asn Ile
                580                 585                 590

His Pro Met Glu Glu Asp Asp Thr Ala Met Tyr Phe Cys Gln Gln Thr
            595                 600                 605

Lys Glu Val Thr Trp Thr Phe Gly Gly Gly Thr Lys Leu Glu Ile Lys
        610                 615                 620

Arg Ala Thr Val Ala Ala Pro Ser Val Phe Ile Phe Pro Pro Ser Asp
625                 630                 635                 640

Glu Gln Leu Lys Ser Gly Thr Ala Ser Val Val Cys Leu Leu Asn Asn
                645                 650                 655

Phe Tyr Pro Arg Glu Ala Lys Val Gln Trp Lys Val Asp Asn Ala Leu
                660                 665                 670

Gln Ser Gly Asn Ser Gln Glu Ser Val Thr Glu Gln Asp Ser Lys Asp
            675                 680                 685

Ser Thr Tyr Ser Leu Ser Ser Thr Leu Thr Leu Ser Lys Ala Asp Tyr
        690                 695                 700

Glu Lys His Lys Val Tyr Ala Cys Glu Val Thr His Gln Gly Leu Ser
705                 710                 715                 720

Ser Pro Val Thr Lys Ser Phe Asn Arg Gly Glu Cys
                725                 730

<210> SEQ ID NO 17
<211> LENGTH: 2205
<212> TYPE: DNA
<213> ORGANISM: Artificial Sequence
<220> FEATURE:
<223> OTHER INFORMATION: Human CD40(Clone #G12)

<400> SEQUENCE: 17
atggattgga catggaggat tctgtttctg gtcgccgccg ctactggaac tcacgccgaa      60
gtgcagctgc tggagtcagg aggaggcctg gtgcagcccg gcggaagcct gaggctgtcc     120
tgcgccgctt ctggattcac ctttagcaca tacgggatgc actgggtgag acaggcccct     180 ggaaagggc tggagtggct gtcttatatc agtgggggca gctcctacat tttctatgca     240
gactccgtgc ggggccgctt taccatcagt cgagataact cagaaaatgc tctgtacctg     300
cagatgaatt ctctgcgcgc cgaggacaca gccgtgtact attgcgccag aattctgcgg     360
ggagggagcg gaatggatct gtggggccag ggaactctgg tcaccgtgtc tagtgcctct     420
accaagggac caagcgtgtt cccactggct ccctcaagca atctaccag tggcggaaca     480 gcagccctgg gctgtctggt gaaggactac ttccccgagc ctgtcacagt gtcatggaat     540
agcggggctc tgaccagcgg cgtccataca tttcctgcag tgctgcagtc ctctgggctg     600
```

-continued

```
tactccctga gttcagtggt cactgtccca agctcctctc tgggcactca gacctatatc    660
tgcaacgtga atcacaagcc tagcaacacc aaagtcgaca agaaagtgga accaaagtcc    720
tgtgataaaa cacatacttg ccctccctgt ccagcaccag agctgctggg cggcccaagc    780
gtgttcctgt tccacccaa gcctaaagac accctgatga tttctcggac tccagaagtc    840
acctgcgtgg tcgtggacgt gagccacgag gaccccgaag tcaagttcaa cgtcgtgtac    900
gtggatggcg tcgaggtgca taatgccaag acaaaaccta ggaggaaca gtacaactca     960
acatatagag tcgtgagcgt cctgactgtg ctgcaccagg actggctgaa cggaaaggag   1020
tataagtgca aagtgtccaa taaggctctg cctgcaccaa tcgagaaaac aatttctaag   1080
gccaaaggcc agcctcggga accacaggtg tacactctgc ctccatctcg cgacgagctg   1140
actaagaatc aggtcagtct gacctgtctg gtgaaaggct tttatccctc cgatatcgct   1200
gtggagtggg aatctaacgg acagcctgaa aacaattaca gaccacacc cctgtcctg    1260
gactccgatg gctctttctt tctgtattca aagctgaccg tggataaaag caggtggcag   1320
cagggaaatg tcttctcatg cagcgtgatg catgaggccc tgcacaacca ttacacacag   1380
aagtccctgt ctctgagtcc tggcaagcga ggaaggaaaa ggagatcagg gagcggcgca   1440
actaattttt ccctgctgaa acaggcaggc gacgtggagg aaaacccagg acctatggtc   1500
ctgcagaccc aggtgttcat ctccctgctg ctgtggattt ctgggcata cggccagagt    1560
gtgctgaccc agccaccctc cgcctctgga acaccaggac agcgagtgac aatcagctgt   1620
actgaagtt caagcaacat ggagctgggg tacaacgtgt actggtatca gcagctgccc    1680
gggacagcac ctaagctgct gatctatggg aacattaatc gcccatccgg cgtgcccgat   1740
cgattcagtg gctcaaaaag cggaacttcc gcctctctgg ctatcagcgg actgcgctcc   1800
gaggacgaag cagattacta ttgcgctgca tgggacaaga tatttcagg actggtcttc   1860
ggaggggca caaagctgac tgtgctgggg cagcctaaag ccgctccatc cgtgaccctg   1920
tttcctccat cctctgagga actgcaggca aacaaagcca cctggtgtg cctgatctct   1980
gacttctacc caggagccgt caccgtggct tggaaggcag atagttcacc agtcaaagct   2040
ggggtggaaa ctaccacacc cagtaagcag tcaaacaaca agtacgcagc cagctcctat   2100
ctgagtctga ccccgagca gtggaagtca cacagaagct attcctgcca ggtcacccat   2160
gaaggaagca cagtggaaaa gacagtcgcc ccaaccgaat gtagc                   2205
```

<210> SEQ ID NO 18
<211> LENGTH: 735
<212> TYPE: PRT
<213> ORGANISM: Artificial Sequence
<220> FEATURE:
<223> OTHER INFORMATION: Human CD40

<400> SEQUENCE: 18

```
Met Asp Trp Thr Trp Arg Ile Leu Phe Leu Val Ala Ala Ala Thr Gly
1               5                   10                  15

Thr His Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Thr Tyr Gly Met His Trp Val Arg Gln Ala Pro Gly Lys Gly Leu
    50                  55                  60

Glu Trp Leu Ser Tyr Ile Ser Gly Gly Ser Ser Tyr Ile Phe Tyr Ala
65                  70                  75                  80
```

```
Asp Ser Val Arg Gly Arg Phe Thr Ile Ser Arg Asp Asn Ser Glu Asn
                85                  90                  95

Ala Leu Tyr Leu Gln Met Asn Ser Leu Arg Ala Glu Asp Thr Ala Val
            100                 105                 110

Tyr Tyr Cys Ala Arg Ile Leu Arg Gly Gly Ser Gly Met Asp Leu Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Val Val Tyr Val Asp Gly Val
    290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys Arg Gly Arg Lys Arg Arg Ser Gly Ser Gly Ala
465                 470                 475                 480

Thr Asn Phe Ser Leu Leu Lys Gln Ala Gly Asp Val Glu Glu Asn Pro
                485                 490                 495
```

```
Gly Pro Met Val Leu Gln Thr Gln Val Phe Ile Ser Leu Leu Leu Trp
                500                 505                 510
Ile Ser Gly Ala Tyr Gly Gln Ser Val Leu Thr Gln Pro Pro Ser Ala
            515                 520                 525
Ser Gly Thr Pro Gly Gln Arg Val Thr Ile Ser Cys Thr Gly Ser Ser
        530                 535                 540
Ser Asn Ile Gly Ala Gly Tyr Asn Val Tyr Trp Tyr Gln Gln Leu Pro
545                 550                 555                 560
Gly Thr Ala Pro Lys Leu Leu Ile Tyr Gly Asn Ile Asn Arg Pro Ser
                565                 570                 575
Gly Val Pro Asp Arg Phe Ser Gly Ser Lys Ser Gly Thr Ser Ala Ser
            580                 585                 590
Leu Ala Ile Ser Gly Leu Arg Ser Glu Asp Glu Ala Asp Tyr Tyr Cys
        595                 600                 605
Ala Ala Trp Asp Lys Ser Ile Ser Gly Leu Val Phe Gly Gly Gly Thr
    610                 615                 620
Lys Leu Thr Val Leu Gly Gln Pro Lys Ala Ala Pro Ser Val Thr Leu
625                 630                 635                 640
Phe Pro Pro Ser Ser Glu Glu Leu Gln Ala Asn Lys Ala Thr Leu Val
                645                 650                 655
Cys Leu Ile Ser Asp Phe Tyr Pro Gly Ala Val Thr Val Ala Trp Lys
            660                 665                 670
Ala Asp Ser Ser Pro Val Lys Ala Gly Val Glu Thr Thr Thr Pro Ser
        675                 680                 685
Lys Gln Ser Asn Asn Lys Tyr Ala Ala Ser Ser Tyr Leu Ser Leu Thr
    690                 695                 700
Pro Glu Gln Trp Lys Ser His Arg Ser Tyr Ser Cys Gln Val Thr His
705                 710                 715                 720
Glu Gly Ser Thr Val Glu Lys Thr Val Ala Pro Thr Glu Cys Ser
                725                 730                 735

<210> SEQ ID NO 19
<211> LENGTH: 2010
<212> TYPE: DNA
<213> ORGANISM: Artificial Sequence
<220> FEATURE:
<223> OTHER INFORMATION: Human CD27 (Agonistic)

<400> SEQUENCE: 19
atggattgga catggattct gtttctggtc gccgctgcta caagagtgca tagtcaggtg     60
cagctggtgg agtcaggagg agggtcgtg cagcccgggc gatctctgag gctgagttgc    120
gccgcttcag gcttcacctt tagctcctac gatatgcact gggtgcggca ggcacctgga    180
aaaggactgg aatgggtcgc tgtgatctgg tatgacggat ctaacaaata ctatgcagat    240
agtgtgaagg ggagattcac tattagccgg gacaactcca agaatacccct gtacctgcag    300 atgaactccc tgcgggctga ggataccgca gtgtactatt gcgcccgcgg ctctggaaat    360
tgggggttct ttgactattg gggcagggc acactggtca ccgtgagcag cgccagtaca    420 aaggcccct cagtgtttcc cctggctcct tcaagcaagt caaccagcgg cggaacagca    480
gccctgggat gtctggtgaa ggactacttc cctgagccag tcaccgtgag ttggaactca    540
ggagctctga ccagcggggt ccatacattt cctgcagtgc tgcagtcctc tggactgtac    600
tccctgagtt cagtggtcac cgtcccaagc tcctctctgg ggactcagac ctatatctgc    660
aacgtgaatc acaaaccatc caatacaaag gtcgacaaga agtggaaacc caaatcttgt    720
```

```
gataagacac atacttgccc tccctgtcca gcacctgagc tgctgggcgg cccaagcgtg    780
ttcctgtttc cacccaagcc taaagatacc ctgatgatta gccgcactcc cgaagtcacc    840
tgcgtggtcg tggacgtgtc ccacgaggac cccgaagtca agttcaactg gtacgtggac    900
ggcgtcgagg tgcataatgc taagacaaaa cctagggagg aacagtacaa tagcacctat    960
agagtcgtgt ccgtcctgac agtgctgcac caggattggc tgaacggaaa ggagtataag   1020
tgcaaagtgt ctaacaaggc cctgccagcc cccatcgaga agaccattag caaggctaaa   1080
gggcagccac gagaaacccca ggtgtacaca ctgcctccat ctagggatga gctgactaaa   1140
aaccaggtca gtctgacctg tctggtgaag gggttctatc ctagcgacat cgcagtggag   1200
tgggaatcca atggccagcc agaaaacaat tacaagacca cccccctgt gctggacagc   1260 gatggctcct tctttctgta ttcaaaactg actgtggaca gagcaggtg gcagcaggga   1320 aacgtctttt cctgctctgt gatgcacgag gccctgcaca atcattacac acagaaaagt   1380
ctgtcactga gcccagggaa acggggccgc aagaggagat ccggatctgg ggcaacaaac   1440
ttcagcctgc tgaagcaggc aggcgacgtg gaggaaaatc ctggaccaat ggattggact   1500
tggattctgt tcctggtcgc tgcagccaca agagtgcatt ccgacattca gatgactcag   1560
tctccaagtt cactgagtgc ctcagtcggc gatcgcgtga ccatcacatg tcgagcttct   1620
cagggaatta gtcgctggct ggcatggtac cagcagaagc tgaaaaagc cccaaagtcc   1680 ctgatctatg ctgcaagctc cctgcagtca ggagtgccca gccgattcag cggctccgga   1740
tctgggactg acttttactct gaccatttct agtctgcagc cagaggattt cgccacctac   1800
tattgccagc agtacaacac atatcccaga acttttggcc agggaacaaa agtggaaatc   1860
aagcggactg tcgccgctcc tagcgtgttc atctttccac cctcagacga gcagctgaag   1920
tccggcaccg cttctgtggt gtgcctgctg aacaatttct accccagaga ggcaaaagtc   1980
cagtggaagg tggataacgc cctgcagtca                                    2010
```

<210> SEQ ID NO 20
<211> LENGTH: 670
<212> TYPE: PRT
<213> ORGANISM: Artificial Sequence
<220> FEATURE:
<223> OTHER INFORMATION: Human CD27 Amino Acid Sequence

<400> SEQUENCE: 20

```
Met Asp Trp Thr Trp Ile Leu Phe Leu Val Ala Ala Thr Arg Val
1               5                   10                  15

His Ser Gln Val Gln Leu Val Glu Ser Gly Gly Gly Val Val Gln Pro
            20                  25                  30

Gly Arg Ser Leu Arg Leu Ser Cys Ala Ala Ser Gly Phe Thr Phe Ser
        35                  40                  45

Ser Tyr Asp Met His Trp Val Arg Gln Ala Pro Gly Lys Gly Leu Glu
    50                  55                  60

Trp Val Ala Val Ile Trp Tyr Asp Gly Ser Asn Lys Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Gly Ser Gly Asn Trp Gly Phe Phe Asp Tyr Trp Gly
        115                 120                 125

Gln Gly Thr Leu Val Thr Val Ser Ser Ala Ser Thr Lys Gly Pro Ser
```

```
            130                 135                 140
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Arg Gly Arg Lys Arg Arg Ser Gly Ser Gly Ala Thr Asn
465                 470                 475                 480

Phe Ser Leu Leu Lys Gln Ala Gly Asp Val Glu Glu Asn Pro Gly Pro
                485                 490                 495

Met Asp Trp Thr Trp Ile Leu Phe Leu Val Ala Ala Ala Thr Arg Val
            500                 505                 510

His Ser Asp Ile Gln Met Thr Gln Ser Pro Ser Ser Leu Ser Ala Ser
        515                 520                 525

Val Gly Asp Arg Val Thr Ile Thr Cys Arg Ala Ser Gln Gly Ile Ser
    530                 535                 540

Arg Trp Leu Ala Trp Tyr Gln Gln Lys Pro Glu Lys Ala Pro Lys Ser
545                 550                 555                 560
```

```
Leu Ile Tyr Ala Ala Ser Ser Leu Gln Ser Gly Val Pro Ser Arg Phe
                565                 570                 575
Ser Gly Ser Gly Ser Gly Thr Asp Phe Thr Leu Thr Ile Ser Ser Leu
            580                 585                 590
Gln Pro Glu Asp Phe Ala Thr Tyr Tyr Cys Gln Gln Tyr Asn Thr Tyr
        595                 600                 605
Pro Arg Thr Phe Gly Gln Gly Thr Lys Val Glu Ile Lys Arg Thr Val
    610                 615                 620
Ala Ala Pro Ser Val Phe Ile Phe Pro Pro Ser Asp Glu Gln Leu Lys
625                 630                 635                 640
Ser Gly Thr Ala Ser Val Val Cys Leu Leu Asn Asn Phe Tyr Pro Arg
                645                 650                 655
Glu Ala Lys Val Gln Trp Lys Val Asp Asn Ala Leu Gln Ser
            660                 665                 670

<210> SEQ ID NO 21
<211> LENGTH: 2223
<212> TYPE: DNA
<213> ORGANISM: Artificial Sequence
<220> FEATURE:
<223> OTHER INFORMATION: Tremelimumab (full-length)

<400> SEQUENCE: 21
```

| | | | | |
|---|---|---|---|---|
| ggatccgcca ccatggactg gacctggaga atcctgttcc tggtggcagc agcaaccgga | 60 |
| acacacgcac aggtgcagct ggtggagagc ggcggcggcg tggtgcagcc aggcaggagc | 120 |
| ctgagactga gctgcgcagc atccggcttc acctttagct cctatggaat gcactgggtg | 180 |
| aggcaggcac caggcaaggg cctggagtgg gtggccgtga tctggtacga cggctctaac | 240 |
| aagtactatg ccgatagcgt gaagggcagg ttcacaatct ctagagacaa cagcaagaat | 300 |
| accctgtacc tgcagatgaa ttccctgaga gccgaggaca cagccgtgta ctattgtgcc | 360 |
| agggacccca ggggcgccac cctgtactat tactattacg gaatggacgt gtggggccag | 420 |
| ggaaccacag tgacagtgtc tagcgcctct accaagggcc ctagcgtgtt ccccctggcc | 480 |
| ccttgcagca gatccacatc tgagagcacc gccgcctgg atgtctggt gaaggactac | 540 |
| ttccccgagc ctgtgacagt gtcttggaac agcggcgccc tgacatccgg agtgcacacc | 600 |
| tttcctgccg tgctgcagtc ctctggcctg tattctctga gctccgtggt gaccgtgcca | 660 |
| tctagcaatt tcggcaccca gacatacacc tgcaacgtgg accacaagcc cagcaataca | 720 |
| aaggtggata gaccgtgga gaggaagtgc tgcgtggagt gccctccctg tccagcccca | 780 |
| cccgtggcag gaccatccgt gttcctgttt cctccaaagc taaggacac actgatgatc | 840 |
| agcagaacac cagaggtgac ctgcgtggtg gtggacgtgt cccacgagga ccccgaggtg | 900 |
| cagtttaact ggtacgtgga tggcgtggag gtgcacaatg ccaagaccaa gccaagggag | 960 |
| gagcagttca acagcacctt cagggtggtg tctgtgctga ccgtggtgca ccaggattgg | 1020 |
| ctgaacggca aggagtacaa gtgcaaggtg tctaataagg cctgccagc ccccatcgag | 1080 |
| aagacaatca gcaagaccaa gggacagcca cgggagccac aggtgtatac cctgccccct | 1140 |
| tcccgcgagg agatgacaaa gaaccaggtg tctctgacct gtctggtgaa gggcttctac | 1200 |
| ccctctgaca tcgccgtgga gtgggagagc aatggccagc ctgagaacaa ttataagacc | 1260 |
| acaccaccca tgctggactc cgatggctct ttctttctgt actccaagct gaccgtggat | 1320 |
| aagtctcggt ggcagcaggg caacgtgttt cctgctctg tgatgcacga ggccctgcac | 1380 |
| aatcactaca cacagaagag cctgtccctg tctccaggca gagggaag gaagagga | 1440 |

-continued

```
agcggctccg gagcaaccaa cttcagcctg ctgaagcagg caggcgacgt ggaggagaat    1500
cctggaccaa tggtgctgca gacacaggtg tttatcagcc tgctgctgtg gatctccggc    1560
gcctatggcg acatccagat gacccagagc ccctcctctc tgtctgccag cgtgggcgat    1620
cgggtgacaa tcacctgtcg cgcctcccag tctatcaact cctatctgga ttggtaccag    1680
cagaagcctg gcaaggcccc aaagctgctg atctacgcag ccagctccct gcagtccgga    1740
gtgccctctc gcttcagcgg ctccggctct ggcacagact ttacactgac catctctagc    1800
ctgcagcctg aggatttcgc cacctattac tgccagcagt attacagcac cccttcacc    1860 tttggccctg gcacaaaggt ggagatcaag aggaccgtgg cagcacctag cgtgttcatc    1920
tttcctccat ccgacgagca gctgaagagc ggaaccgcat ccgtggtgtg cctgctgaac    1980
aacttctacc cacgcgaggc caaggtgcag tggaaggtgg ataacgccct gcagagcggc    2040
aattcccagg agtctgtgac agagcaggac agcaaggatt ccacctacag cctgtccaac    2100
acactgaccc tgagcaaggc cgactatgag aagcacaagg tgtacgcctg cgaggtgaca    2160
caccagggcc tgtcctctcc cgtgaccaag tccttcaatc ggggcgagtg ttgataactc    2220
gag                                                                  2223
```

<210> SEQ ID NO 22
<211> LENGTH: 733
<212> TYPE: PRT
<213> ORGANISM: Artificial Sequence
<220> FEATURE:
<223> OTHER INFORMATION: Tremelimumab (full-length) Amino Acid Sequence

<400> SEQUENCE: 22

```
Met Asp Trp Thr Trp Arg Ile Leu Phe Leu Val Ala Ala Thr Gly
1               5                   10                  15

Thr His Ala Gln Val Gln Leu Val Glu Ser Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Pro Arg Gly Ala Thr Leu Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
```

```
                    210                 215                 220
Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                    245                 250                 255

Pro Val Ala Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Gln Phe Asn Trp Tyr Val Asp Gly
        290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                    325                 330                 335

Leu Asn Gly Lys Glu Tyr Lys Cys Lys Val Ser Asn Lys Gly Leu Pro
                340                 345                 350

Ala Pro Ile Glu Lys Thr Ile Ser Lys Thr Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys Arg Gly Arg Lys Arg Arg Ser Gly Ser Gly
465                 470                 475                 480

Ala Thr Asn Phe Ser Leu Leu Lys Gln Ala Gly Asp Val Glu Glu Asn
                485                 490                 495

Pro Gly Pro Met Val Leu Gln Thr Gln Val Phe Ile Ser Leu Leu Leu
                500                 505                 510

Trp Ile Ser Gly Ala Tyr Gly Asp Ile Gln Met Thr Gln Ser Pro Ser
            515                 520                 525

Ser Leu Ser Ala Ser Val Gly Asp Arg Val Thr Ile Thr Cys Arg Ala
        530                 535                 540

Ser Gln Ser Ile Asn Ser Tyr Leu Asp Trp Tyr Gln Gln Lys Pro Gly
545                 550                 555                 560

Lys Ala Pro Lys Leu Leu Ile Tyr Ala Ala Ser Ser Leu Gln Ser Gly
                565                 570                 575

Val Pro Ser Arg Phe Ser Gly Ser Gly Ser Gly Thr Asp Phe Thr Leu
                580                 585                 590

Thr Ile Ser Ser Leu Gln Pro Glu Asp Phe Ala Thr Tyr Tyr Cys Gln
            595                 600                 605

Gln Tyr Tyr Ser Thr Pro Phe Thr Phe Gly Pro Gly Thr Lys Val Glu
        610                 615                 620

Ile Lys Arg Thr Val Ala Ala Pro Ser Val Phe Ile Phe Pro Pro Ser
625                 630                 635                 640
```

```
Asp Glu Gln Leu Lys Ser Gly Thr Ala Ser Val Cys Leu Leu Asn
                645                 650                 655

Asn Phe Tyr Pro Arg Glu Ala Lys Val Gln Trp Lys Val Asp Asn Ala
            660                 665                 670

Leu Gln Ser Gly Asn Ser Gln Glu Ser Val Thr Glu Gln Asp Ser Lys
        675                 680                 685

Asp Ser Thr Tyr Ser Leu Ser Asn Thr Leu Thr Leu Ser Lys Ala Asp
    690                 695                 700

Tyr Glu Lys His Lys Val Tyr Ala Cys Glu Val Thr His Gln Gly Leu
705                 710                 715                 720

Ser Ser Pro Val Thr Lys Ser Phe Asn Arg Gly Glu Cys
                725                 730

<210> SEQ ID NO 23
<211> LENGTH: 2199
<212> TYPE: DNA
<213> ORGANISM: Artificial Sequence
<220> FEATURE:
<223> OTHER INFORMATION: Tremelimumab (frame)

<400> SEQUENCE: 23
atggactgga cctggagaat cctgttcctg gtggcagcag caaccggaac acacgcacag      60
gtgcagctgg tggagagcgg cggcggcgtg gtgcagccag gcaggagcct gagactgagc     120
tgcgcagcat ccggcttcac ctttagctcc tatggaatgc actgggtgag gcaggcacca     180
ggcaagggcc tggagtgggt ggccgtgatc tggtacgacg gctctaacaa gtactatgcc     240
gatagcgtga agggcaggtt cacaatctct agagacaaca gcaagaatac cctgtacctg     300
cagatgaatt ccctgagagc cgaggacaca gccgtgtact attgtgccag ggaccccagg     360
ggcgccaccc tgtactatta ctattacgga atggacgtgt ggggccaggg aaccacagtg     420
acagtgtcta gcgcctctac caagggccct agcgtgtttc ccctggcccc ttgcagcaga     480
tccacatctg agagcaccgc cgccctggga tgtctggtga aggactactt ccccgagcct     540
gtgacagtgt cttggaacag cggcgccctg acatccggag tgcacacctt tcctgccgtg     600
ctgcagtcct ctggcctgta ttctctgagc tccgtggtga ccgtgccatc tagcaatttc     660
ggcacccaga catacacctg caacgtggac cacaagccca gcaatacaaa ggtggataag     720
accgtggaga ggaagtgctg cgtggagtgc cctccctgtc cagccccacc cgtggcagga     780
ccatccgtgt tcctgtttcc tccaaagcct aaggacacac tgatgatcag cagaacacca     840
gaggtgacct gcgtggtggt ggacgtgtcc cacgaggacc ccgaggtgca gtttaactgg     900
tacgtggatg gcgtggaggt gcacaatgcc aagaccaagc caagggagga gcagttcaac     960
agcaccttca gggtggtgtc tgtgctgacc gtggtgcacc aggattggct gaacggcaag    1020
gagtacaagt gcaaggtgtc taataagggc ctgccagccc catcgagaa gacaatcagc    1080 aagaccaagg acagccacg ggagccacag gtgtataccc tgccccttc ccgcgaggag    1140 atgacaaaga accaggtgtc tctgacctgt ctggtgaagg gcttctaccc ctctgacatc    1200
gccgtggagt gggagagcaa tggccagcct gagaacaatt ataagaccac accacccatg    1260
ctggactccg atggctcttt cttctctgta tccaagctga ccgtggataa gtctcggtgg    1320
cagcagggca acgtgttttc ctgctctgtg atgcacgagg ccctgcacaa tcactacaca    1380
cagaagagcc tgtccctgtc tccaggcaag aggggaagga gaggagaag cggctccgga    1440 gcaaccaact tcagcctgct gaagcaggca ggcgacgtgg aggagaatcc tggaccaatg    1500
```

-continued

```
gtgctgcaga cacaggtgtt tatcagcctg ctgctgtgga tctccggcgc ctatggcgac    1560
atccagatga cccagagccc ctcctctctg tctgccagcg tgggcgatcg ggtgacaatc    1620
acctgtcgcg cctcccagtc tatcaactcc tatctggatt ggtaccagca gaagcctggc    1680
aaggccccaa agctgctgat ctacgcagcc agctccctgc agtccggagt gccctctcgc    1740
ttcagcggct ccggctctgg cacagacttt acactgacca tctctagcct gcagcctgag    1800
gatttcgcca ctattactg ccagcagtat tacagcacac ccttcacctt tggccctggc    1860
acaaaggtgg agatcaagag gaccgtggca gcacctagcg tgttcatctt tcctccatcc    1920
gacgagcagc tgaagagcgg aaccgcatcc gtggtgtgcc tgctgaacaa cttctaccca    1980
cgcgaggcca aggtgcagtg gaaggtggat aacgccctgc agagcggcaa ttcccaggag    2040
tctgtgacag agcaggacag caaggattcc acctacagcc tgtccaacac actgaccctg    2100
agcaaggccg actatgagaa gcacaaggtg tacgcctgcg aggtgacaca ccagggcctg    2160
tcctctcccg tgaccaagtc cttcaatcgg ggcgagtgt                           2199
```

<210> SEQ ID NO 24
<211> LENGTH: 733
<212> TYPE: PRT
<213> ORGANISM: Artificial Sequence
<220> FEATURE:
<223> OTHER INFORMATION: Tremelimumab (frame) Amino Acid Sequence

<400> SEQUENCE: 24

```
Met Asp Trp Thr Trp Arg Ile Leu Phe Leu Val Ala Ala Thr Gly
1               5                   10                  15

Thr His Ala Gln Val Gln Leu Val Glu Ser Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
        50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Pro Arg Gly Ala Thr Leu Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240
```

-continued

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys Arg Gly Arg Lys Arg Arg Ser Gly Ser Gly
465                 470                 475                 480

Ala Thr Asn Phe Ser Leu Leu Lys Gln Ala Gly Asp Val Glu Glu Asn
                485                 490                 495

Pro Gly Pro Met Val Leu Gln Thr Gln Val Phe Ile Ser Leu Leu Leu
            500                 505                 510

Trp Ile Ser Gly Ala Tyr Gly Asp Ile Gln Met Thr Gln Ser Pro Ser
        515                 520                 525

Ser Leu Ser Ala Ser Val Gly Asp Arg Val Thr Ile Thr Cys Arg Ala
    530                 535                 540

Ser Gln Ser Ile Asn Ser Tyr Leu Asp Trp Tyr Gln Gln Lys Pro Gly
545                 550                 555                 560

Lys Ala Pro Lys Leu Leu Ile Tyr Ala Ala Ser Ser Leu Gln Ser Gly
                565                 570                 575

Val Pro Ser Arg Phe Ser Gly Ser Gly Ser Gly Thr Asp Phe Thr Leu
            580                 585                 590

Thr Ile Ser Ser Leu Gln Pro Glu Asp Phe Ala Thr Tyr Tyr Cys Gln
        595                 600                 605

Gln Tyr Tyr Ser Thr Pro Phe Thr Phe Gly Pro Gly Thr Lys Val Glu
    610                 615                 620

Ile Lys Arg Thr Val Ala Ala Pro Ser Val Phe Ile Phe Pro Pro Ser
625                 630                 635                 640

Asp Glu Gln Leu Lys Ser Gly Thr Ala Ser Val Val Cys Leu Leu Asn
                645                 650                 655

Asn Phe Tyr Pro Arg Glu Ala Lys Val Gln Trp Lys Val Asp Asn Ala

```
                660               665               670
Leu Gln Ser Gly Asn Ser Gln Glu Ser Val Thr Glu Gln Asp Ser Lys
            675               680               685

Asp Ser Thr Tyr Ser Leu Ser Asn Thr Leu Thr Leu Ser Lys Ala Asp
        690               695               700

Tyr Glu Lys His Lys Val Tyr Ala Cys Glu Val Thr His Gln Gly Leu
705               710               715               720

Ser Ser Pro Val Thr Lys Ser Phe Asn Arg Gly Glu Cys
                725               730

<210> SEQ ID NO 25
<211> LENGTH: 2217
<212> TYPE: DNA
<213> ORGANISM: Artificial Sequence
<220> FEATURE:
<223> OTHER INFORMATION: Ipilimumab (full-length)

<400> SEQUENCE: 25
```

| | | | | | |
|---|---|---|---|---|---|
| ggatccgcca | ccatggactg | gacctggaga | atcctgttcc | tggtggcagc | agcaaccgga | 60 |
| acacacgcac | aggtgcagct | ggtggagagc | ggcggcggcg | tggtgcagcc | tggcaggagc | 120 |
| ctgagactga | gctgcgcagc | atccggcttc | acctttagct | cctacacaat | gcactgggtg | 180 |
| agacaggcac | caggcaaggg | cctggagtgg | gtgaccttca | tctcttatga | cggcaacaat | 240 |
| aagtactatg | ccgatagcgt | gaagggccgg | tttaccatct | ctcgcgacaa | cagcaagaat | 300 |
| acactgtacc | tgcagatgaa | ctccctgcgg | gccgaggaca | ccgccatcta | ctattgcgca | 360 |
| aggacaggat | ggctgggacc | attcgattat | tggggccagg | gcaccctggt | gacagtgtct | 420 |
| agcgccagca | caaagggacc | atccgtgttt | ccactggcac | cttcctctaa | gagcacctcc | 480 |
| ggcggcacag | ccgccctggg | ctgtctggtg | aaggattact | ccctgagcc | agtgaccgtg | 540 |
| tcctggaact | ctggcgccct | gaccagcgga | gtgcacacat | tccagccgt | gctgcagagc | 600 |
| tccggcctgt | actccctgtc | tagcgtggtg | accgtgcctt | cctctagcct | gggcacccag | 660 |
| acatatatct | gcaacgtgaa | tcacaagcct | tccaatacaa | aggtggacaa | gaaggtggag | 720 |
| ccaaagtctt | gtgataagac | ccacacatgc | cctccctgtc | cagcacctga | gctgctgggc | 780 |
| ggcccaagcg | tgttcctgtt | tccacccaag | cccaaggaca | cactgatgat | cagccggacc | 840 |
| ccagaggtga | catgcgtggt | ggtggacgtg | tcccacgagg | accccgaggt | gaagttcaac | 900 |
| tggtacgtgg | atggcgtgga | ggtgcacaat | gccaagacca | agcctaggga | ggagcagtac | 960 |
| aattctacct | atagagtggt | gagcgtgctg | acagtgctgc | accaggactg | gctgaacggc | 1020 |
| aaggagtata | agtgcaaggt | gtctaataag | gccctgccag | cccccatcga | gaagaccatc | 1080 |
| agcaaggcaa | agggacagcc | aagggagcca | caggtgtaca | cactgcctcc | aagcagagac | 1140 |
| gagctgacca | agaaccaggt | gtccctgaca | tgtctggtga | agggcttcta | tcccctcgat | 1200 |
| atcgccgtgg | agtgggagtc | taatggccag | cctgagaaca | attacaagac | cacaccccct | 1260 |
| gtgctggaca | gcgatggctc | cttctttctg | tatagcaagc | tgaccgtgga | caagtccagg | 1320 |
| tggcagcagg | gcaacgtgtt | ttcttgcagc | gtgatgcacg | aggccctgca | caatcactac | 1380 |
| acccagaagt | ccctgtctct | gagcccaggc | aagaggggaa | ggaagaggag | atccggctct | 1440 |
| ggcgccacaa | acttcagcct | gctgaagcag | gccggcgatg | tggaggagaa | tcctggccca | 1500 |
| atggtgctgc | agacccaggt | gtttatctcc | ctgctgctgt | ggatctctgg | cgcctacgga | 1560 |
| gagatcgtgc | tgacccagtc | cccaggcaca | ctgagcctgt | ccctggagac | agggccacc | 1620 |
| ctgtcttgta | gagcctctca | gagcgtgggc | tcctcttacc | tggcctggta | tcagcagaag | 1680 |

-continued

```
cctggccagg ccccaagact gctgatctac ggagccttca gccgggccac cggcatcccc    1740
gaccgcttct ccggctctgg cagcggcaca gacttcaccc tgacaatctc ccggctggag    1800
cctgaggact tcgccgtgta ctattgccag cagtatggca gctccccatg gacctttggc    1860
cagggcacaa aggtggagat caagaggacc gtggcagcac caagcgtgtt catctttcca    1920
cccagcgacg agcagctgaa gtccggcaca gcctctgtgg tgtgcctgct gaacaatttc    1980
taccctcggg aggccaaggt gcagtggaag gtggataacg ccctgcagtc tggcaatagc    2040
caggagtccg tgaccgagca ggactctaag gatagcacat attccctgtc tagcaccctg    2100
acactgagca aggccgatta cgagaagcac aaggtgtatg catgcgaggt gacccaccag    2160
ggcctgtcct ctcccgtgac aaagtccttt aaccgcggcg agtgttgata actcgag      2217
```

<210> SEQ ID NO 26
<211> LENGTH: 731
<212> TYPE: PRT
<213> ORGANISM: Artificial Sequence
<220> FEATURE:
<223> OTHER INFORMATION: Ipilimumab (full-length) Amino Acid Sequence

<400> SEQUENCE: 26

```
Met Asp Trp Thr Trp Arg Ile Leu Phe Leu Val Ala Ala Thr Gly
1               5                   10                  15

Thr His Ala Gln Val Gln Leu Val Glu Ser Gly Gly Gly Val Gln
                20                  25                  30

Pro Gly Arg Ser Leu Arg Leu Ser Cys Ala Ala Ser Gly Phe Thr Phe
            35                  40                  45

Ser Ser Tyr Thr Met His Trp Val Arg Gln Ala Pro Gly Lys Gly Leu
        50                  55                  60

Glu Trp Val Thr Phe Ile Ser Tyr Asp Gly Asn Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Ile
            100                 105                 110

Tyr Tyr Cys Ala Arg Thr Gly Trp Leu Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270
```

```
Ile Ser Arg Thr Pro Glu Val Thr Cys Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys Arg Gly Arg Lys Arg Arg Ser Gly Ser Gly Ala Thr Asn
465                 470                 475                 480

Phe Ser Leu Leu Lys Gln Ala Gly Asp Val Glu Glu Asn Pro Gly Pro
                485                 490                 495

Met Val Leu Gln Thr Gln Val Phe Ile Ser Leu Leu Leu Trp Ile Ser
                500                 505                 510

Gly Ala Tyr Gly Glu Ile Val Leu Thr Gln Ser Pro Gly Thr Leu Ser
            515                 520                 525

Leu Ser Pro Gly Glu Arg Ala Thr Leu Ser Cys Arg Ala Ser Gln Ser
        530                 535                 540

Val Gly Ser Ser Tyr Leu Ala Trp Tyr Gln Gln Lys Pro Gly Gln Ala
545                 550                 555                 560

Pro Arg Leu Leu Ile Tyr Gly Ala Phe Ser Arg Ala Thr Gly Ile Pro
                565                 570                 575

Asp Arg Phe Ser Gly Ser Gly Ser Gly Thr Asp Phe Thr Leu Thr Ile
                580                 585                 590

Ser Arg Leu Glu Pro Glu Asp Phe Ala Val Tyr Tyr Cys Gln Gln Tyr
            595                 600                 605

Gly Ser Ser Pro Trp Thr Phe Gly Gln Gly Thr Lys Val Glu Ile Lys
        610                 615                 620

Arg Thr Val Ala Ala Pro Ser Val Phe Ile Phe Pro Pro Ser Asp Glu
625                 630                 635                 640

Gln Leu Lys Ser Gly Thr Ala Ser Val Val Cys Leu Leu Asn Asn Phe
                645                 650                 655

Tyr Pro Arg Glu Ala Lys Val Gln Trp Lys Val Asp Asn Ala Leu Gln
                660                 665                 670

Ser Gly Asn Ser Gln Glu Ser Val Thr Glu Gln Asp Ser Lys Asp Ser
            675                 680                 685
```

Thr Tyr Ser Leu Ser Ser Thr Leu Thr Leu Ser Lys Ala Asp Tyr Glu
    690             695             700

Lys His Lys Val Tyr Ala Cys Glu Val Thr His Gln Gly Leu Ser Ser
705             710             715             720

Pro Val Thr Lys Ser Phe Asn Arg Gly Glu Cys
            725             730

<210> SEQ ID NO 27
<211> LENGTH: 2193
<212> TYPE: DNA
<213> ORGANISM: Artificial Sequence
<220> FEATURE:
<223> OTHER INFORMATION: Ipilimumab (frame)

<400> SEQUENCE: 27

| | | | | | |
|---|---|---|---|---|---|
| atggactgga | cctggagaat | cctgttcctg | gtggcagcag | caaccggaac | acacgcacag | 60 |
| gtgcagctgg | tggagagcgg | cggcggcgtg | gtgcagcctg | gcaggagcct | gagactgagc | 120 |
| tgcgcagcat | ccggcttcac | ctttagctcc | tacacaatgc | actgggtgag | acaggcacca | 180 |
| ggcaagggcc | tggagtgggt | gaccttcatc | tcttatgacg | gcaacaataa | gtactatgcc | 240 |
| gatagcgtga | agggccggtt | taccatctct | cgcgacaaca | gcaagaatac | actgtacctg | 300 |
| cagatgaact | ccctgcgggc | cgaggacacc | gccatctact | attgcgcaag | gacaggatgg | 360 |
| ctgggaccat | tcgattattg | gggccagggc | accctggtga | cagtgtctag | cgccagcaca | 420 |
| aagggaccat | ccgtgtttcc | actggcacct | tcctctaaga | gcacctccgg | cggcacagcc | 480 |
| gccctgggct | gtctggtgaa | ggattacttc | cctgagccag | tgaccgtgtc | ctggaactct | 540 |
| ggcgccctga | ccagcggagt | gcacacattt | ccagccgtgc | tgcagagctc | cggcctgtac | 600 |
| tccctgtcta | gcgtggtgac | cgtgccttcc | tctagcctgg | gcacccagac | atatatctgc | 660 |
| aacgtgaatc | acaagccttc | caatacaaag | gtggacaaga | aggtggagcc | aaagtcttgt | 720 |
| gataagaccc | acacatgccc | ctcctgtcca | gcacctgagc | tgctgggcgg | cccaagcgtg | 780 |
| ttcctgtttc | cacccaagcc | caaggacaca | ctgatgatca | gccggacccc | agaggtgaca | 840 |
| tgcgtggtgg | tggacgtgtc | ccacgaggac | cccgaggtga | agttcaactg | gtacgtggat | 900 |
| ggcgtggagg | tgcacaatgc | caagaccaag | cctagggagg | agcagtacaa | ttctacctat | 960 |
| agagtggtga | gcgtgctgac | agtgctgcac | caggactggc | tgaacggcaa | ggagtataag | 1020 |
| tgcaaggtgt | ctaataaggc | cctgccagcc | cccatcgaga | agaccatcag | caaggcaaag | 1080 |
| ggacagccaa | gggagccaca | ggtgtacaca | ctgcctccaa | gcagagacga | gctgaccaag | 1140 |
| aaccaggtgt | ccctgacatg | tctggtgaag | ggcttctatc | cctccgatat | cgccgtggag | 1200 |
| tgggagtcta | atggccagcc | tgagaacaat | tacaagacca | cccccctgt | gctggacagc | 1260 |
| gatggctcct | tctttctgta | tagcaagctg | accgtggaca | agtccaggtg | gcagcagggc | 1320 |
| aacgtgtttt | cttgcagcgt | gatgcacgag | gccctgcaca | atcactacac | ccagaagtcc | 1380 |
| ctgtctctga | gcccaggcaa | gagggggaagg | aagaggagat | ccggctctgg | cgccacaaac | 1440 |
| ttcagcctgc | tgaagcaggc | cggcgatgtg | gaggagaatc | ctggcccaat | ggtgctgcag | 1500 |
| acccaggtgt | ttatctccct | gctgctgtgg | atctctggcg | cctacggaga | gatcgtgctg | 1560 |
| acccagtccc | caggcacact | gagcctgtcc | cctggagaga | gggccaccct | gtcttgtaga | 1620 |
| gcctctcaga | gcgtgggctc | ctcttacctg | gcctggtatc | agcagaagcc | tggccaggcc | 1680 |
| ccaagactgc | tgatctacgg | agccttcagc | cgggccaccg | gcatccccga | ccgcttctcc | 1740 |
| ggctctggca | gcggcacaga | cttcaccctg | acaatctccc | ggctggagcc | tgaggacttc | 1800 |

-continued

```
gccgtgtact attgccagca gtatggcagc tccccatgga cctttggcca gggcacaaag    1860
gtggagatca agaggaccgt ggcagcacca agcgtgttca tctttccacc cagcgacgag    1920
cagctgaagt ccggcacagc ctctgtggtg tgcctgctga acaatttcta ccctcgggag    1980
gccaaggtgc agtggaaggt ggataacgcc ctgcagtctg gcaatagcca ggagtccgtg    2040
accgagcagg actctaagga tagcacatat tccctgtcta gcaccctgac actgagcaag    2100
gccgattacg agaagcacaa ggtgtatgca tgcgaggtga cccaccaggg cctgtcctct    2160
cccgtgacaa agtcctttaa ccgcggcgag tgt                                 2193
```

<210> SEQ ID NO 28
<211> LENGTH: 731
<212> TYPE: PRT
<213> ORGANISM: Artificial Sequence
<220> FEATURE:
<223> OTHER INFORMATION: Ipilimumab (frame) Amino Acid Sequence

<400> SEQUENCE: 28

```
Met Asp Trp Thr Trp Arg Ile Leu Phe Leu Val Ala Ala Thr Gly
1               5                   10                  15

Thr His Ala Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
        35                  40                  45

Ser Ser Tyr Thr Met His Trp Val Arg Gln Ala Pro Gly Lys Gly Leu
    50                  55                  60

Glu Trp Val Thr Phe Ile Ser Tyr Asp Gly Asn Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Ile
            100                 105                 110

Tyr Tyr Cys Ala Arg Thr Gly Trp Leu Gly Pro Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
```

```
            290                 295                 300
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Arg Gly Arg Lys Arg Arg Ser Gly Ser Gly Ala Thr Asn
465                 470                 475                 480

Phe Ser Leu Leu Lys Gln Ala Gly Asp Val Glu Glu Asn Pro Gly Pro
                485                 490                 495

Met Val Leu Gln Thr Gln Val Phe Ile Ser Leu Leu Leu Trp Ile Ser
            500                 505                 510

Gly Ala Tyr Gly Glu Ile Val Leu Thr Gln Ser Pro Gly Thr Leu Ser
        515                 520                 525

Leu Ser Pro Gly Glu Arg Ala Thr Leu Ser Cys Arg Ala Ser Gln Ser
    530                 535                 540

Val Gly Ser Ser Tyr Leu Ala Trp Tyr Gln Gln Lys Pro Gly Gln Ala
545                 550                 555                 560

Pro Arg Leu Leu Ile Tyr Gly Ala Phe Ser Arg Ala Thr Gly Ile Pro
                565                 570                 575

Asp Arg Phe Ser Gly Ser Gly Ser Gly Thr Asp Phe Thr Leu Thr Ile
            580                 585                 590

Ser Arg Leu Glu Pro Glu Asp Phe Ala Val Tyr Tyr Cys Gln Gln Tyr
        595                 600                 605

Gly Ser Ser Pro Trp Thr Phe Gly Gln Gly Thr Lys Val Glu Ile Lys
    610                 615                 620

Arg Thr Val Ala Ala Pro Ser Val Phe Ile Phe Pro Pro Ser Asp Glu
625                 630                 635                 640

Gln Leu Lys Ser Gly Thr Ala Ser Val Val Cys Leu Leu Asn Asn Phe
                645                 650                 655

Tyr Pro Arg Glu Ala Lys Val Gln Trp Lys Val Asp Asn Ala Leu Gln
            660                 665                 670

Ser Gly Asn Ser Gln Glu Ser Val Thr Glu Gln Asp Ser Lys Asp Ser
        675                 680                 685
```

```
Thr Tyr Ser Leu Ser Ser Thr Leu Thr Leu Ser Lys Ala Asp Tyr Glu
    690             695             700
Lys His Lys Val Tyr Ala Cys Glu Val Thr His Gln Gly Leu Ser Ser
705             710             715             720
Pro Val Thr Lys Ser Phe Asn Arg Gly Glu Cys
                725             730
```